(12) United States Patent
Iyer et al.

(10) Patent No.: US 11,701,423 B2
(45) Date of Patent: Jul. 18, 2023

(54) HYPERIMMUNIZED EGG PRODUCT FOR TREATMENT OR PREVENTION OF CORONAVIRUS INFECTION

(71) Applicant: LAY SCIENCES INC., Jupiter, FL (US)

(72) Inventors: Subramanian V. Iyer, Royal Palm Beach, FL (US); Satishchandran Chandrasekhar, Jupiter, FL (US); Uday Saxena, Bengaluru (IN); Gopi Kadiyala, Karnataka (IN)

(73) Assignee: LAY SCIENCES, INC., Jupiter, FL (US)

( * ) Notice: Subject to any disclaimer, the term of this patent is extended or adjusted under 35 U.S.C. 154(b) by 0 days.

(21) Appl. No.: 17/693,280

(22) Filed: Mar. 11, 2022

(65) Prior Publication Data
US 2022/0288193 A1    Sep. 15, 2022

Related U.S. Application Data

(60) Provisional application No. 63/160,155, filed on Mar. 12, 2021.

(51) Int. Cl.
| | |
|---|---|
| *A61K 39/215* | (2006.01) |
| *A23B 5/00* | (2006.01) |
| *A61K 39/00* | (2006.01) |

(52) U.S. Cl.
CPC .............. *A61K 39/215* (2013.01); *A23B 5/00* (2013.01); *A61K 2039/552* (2013.01)

(58) Field of Classification Search
None
See application file for complete search history.

(56) References Cited

U.S. PATENT DOCUMENTS

| | | | |
|---|---|---|---|
| 4,748,018 | A | 5/1988 | Stolle et al. |
| 5,772,999 | A | 6/1998 | Greenblatt et al. |
| 6,803,035 | B2 | 10/2004 | Greenblatt et al. |
| 7,105,158 | B1 | 9/2006 | D'Souza et al. |
| 10,434,116 | B2 | 10/2019 | Frieman et al. |
| 2004/0156857 | A1 | 8/2004 | Adalsteinsson et al. |
| 2021/0347858 | A1* | 11/2021 | Starzl ................. C07K 14/165 |

OTHER PUBLICATIONS

CDC's Interim Clinical Considerations, Jul. 20, 2022, from https://www.cdc.gov/vaccines/covid-19/clinical-considerations/interim-considerations-us.html, accessed Aug. 9, 2022, 30 page printout. (Year: 2022).*

Elzoghby et al., Journal of Controlled Release, 2012, 157:168-182. (Year: 2012).*

Fertel et al., "Formation of Antibodies to Prostaglandins in the Yolk of Chicken Eggs," Biochemical and Biophysical Research Communications, 102: 1028-1033 (1981).

Gallaher et al., "Analysis of Wuhan Coronavirus: Deja Vu," Virological.org 63, (2020), 88 pages.

Gallaher et al., "Analysis of Wuhan Coronavirus: Deja Vu Update Feb. 7, 2020," Virological.org 63, (2020), 97 pages.

Jensenius et al., "Eggs: Conveniently Packaged Antibodies. Methods for Purification of Yolk IgG," Journal of Immunological Methods, 46: 63-68 (1981).

Lebacq-Verheyden et al., "Quantification and Distribution of Chicken Immunoglobulins IgA, IgM and IgG in Serum and Secretions," Immunology, 27: 683-692 (1974).

Leslie et al., "Phylogeny of Immunoglobulin Structure and Function: III. Immunoglobulins of the Chicken," Journal of Experimental Medicine, 130: 1337-1352 (1969).

Longping et al., "A Novel Activation Mechanism of Avian Influenza Virus H9N2 by Furin," Journal of Virology, 88:1673-1683 (2014).

Mathiowitz et al., "Microencapsulation," in Encyclopedia of Controlled Drug Delivery, vol. 2, pp. 495-546, 1999, John Wiley & Sons, Inc. New Yowk, N.Y.

Matsuyama et al., "Middle East Respiratory Syndrome Coronavirus Spike Protein Is Not Activated Directly by Cellular Furin During Viral Entry into Target Cells," Journal of Virology, vol. 92, Issue 19, 2018 (e00683-18), 12 pages.

Polson et al., "Antibodies to Proteins From Yolk of Immunized Hens," Immunological Communications, 9: 495-514 (1980).

Wan et al., "Receptor Recognition by the Novel Coronavirus from Wuhan: an Analysis based on Decade-Long Structural Studies of SARS Coronavirus," Journal of Virology, vol. 94, Issue 7, 2020 (e00127-20), 9 pages.

Wrapp et al., "Cryo-EM structure of the 2019-nCoV spike in the prefusion conformation," Science, 367: 1260-1263 (2020).

Bonnin et al., "HCov-229E spike protein fusion activation by trypsin-like serine proteases is mediated by proteolytic processing in the S2' region," Journal of General Virology 99:908-912 (2018).

Carlander et al., "Chicken Antibodies: A Clinical Chemistry Perspective," Upsala Journal of Medical Sciences 104(3):179-189 (1999).

(Continued)

*Primary Examiner* — Stacy B Chen
(74) *Attorney, Agent, or Firm* — Dentons US LLP

(57) ABSTRACT

In one aspect, the present disclosure is directed to a method for preventing or treating a coronavirus infection in a subject in need thereof, comprising administering to the subject a therapeutically effective amount of a hyperimmunized egg product obtained from an egg-producing animal, thereby preventing or treating coronavirus infection in the subject, wherein the hyperimmunized egg product comprises a therapeutically effective amount of one or more antibodies to the coronavirus. The present disclosure is also directed to hyperimmunized eggs and egg products produced by an animal that has been hyperimmunized with an antigen selected from i) a spike (S) protein, an S1 subunit protein, an S2 subunit protein, a receptor binding domain (RBD), and an immunogenic fragment thereof; ii) a nucleocapsid (N) protein, and an immunogenic fragment thereof; iii) a human ACE2 receptor protein, and an immunogenic fragment thereof; and iv) a human coronavirus selected from the group consisting of SARS-CoV, MERS-CoV, SARS-CoV-2, HCoV-HKU1, HCoV-NL63, HCoV-OC43 and HCoV-229E. Methods of preparing the hyperimmunized eggs and egg products are also disclosed.

7 Claims, 7 Drawing Sheets
Specification includes a Sequence Listing.

(56) References Cited

OTHER PUBLICATIONS

De Haan et al., "Cleavage of Group 1 Coronavirus Spike Proteins: How Furin Cleavage Is Traded Off against Heparan Sulfate Binding upon Cell Culture Adaptation," Journal of Virology 82(12):6078-6083 (2008).

Gralinski et al., "Return of the Coronavirus: 2019-nCoV," Viruses 12:135 (2020), doi:10.3390/v12020135, 8 pages.

Hoffmann et al., "SARS-CoV-2 Cell Entry Depends on ACE2 and TMPRSS2 and Is Blocked by a Clinically Proven Protease Inhibitor," Cell 181:271-280.e1-e5 (2020).

Jia et al., "ACE2 Receptor Expression and Severe Acute Respiratory Syndrome Coronavirus Infection Depend on Differentiation of Human Airway Epithelia," Journal of Virology 79(23):14614-14621 (2005).

Lin et al., "Identification of residues in the receptor-binding domain (RBD) of the spike protein of human coronavirus NL63 that are critical for the RBD-ACE2 receptor interaction," Journal of General Virology 89:1015-1024 (2008).

Lucchese, "Epitopes for a 2019-nCoV vaccine," Cellular & Molecular Immunology 17:539-540 (2020).

Meulenaer et al., "Isolation and Purification of Chicken Egg yolk Immunoglobulins: A Review," Food and Agricultural Immunology 13:275-288 (2001).

Millet et al., "Host cell entry of Middle East respiratory syndrome coronavirus after two-step, furin-mediated activation of the spike protein," Proceedings of the National Academy of Sciences of the U.S.A. 111(42):15214-15219 (2014).

Yang et al., "A novel and convenient method to immunize animals: Inclusion bodies from recombinant bacteria as antigen to directly immunize animals," African Journal Biotechnology 10(41):8146-8150 (2011).

\* cited by examiner

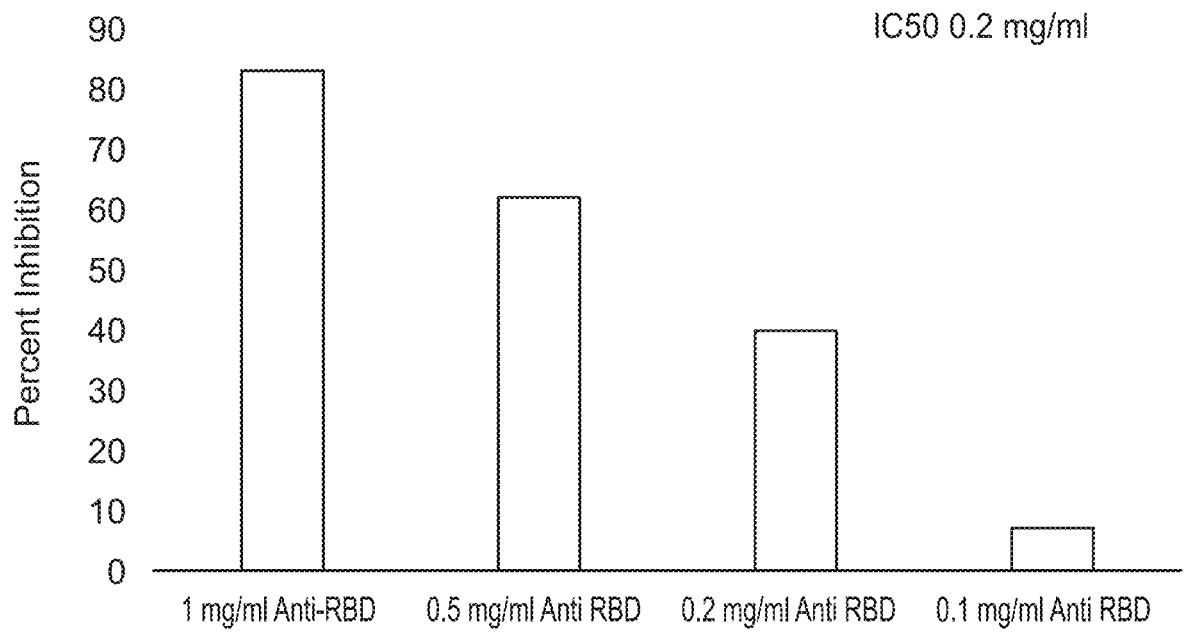
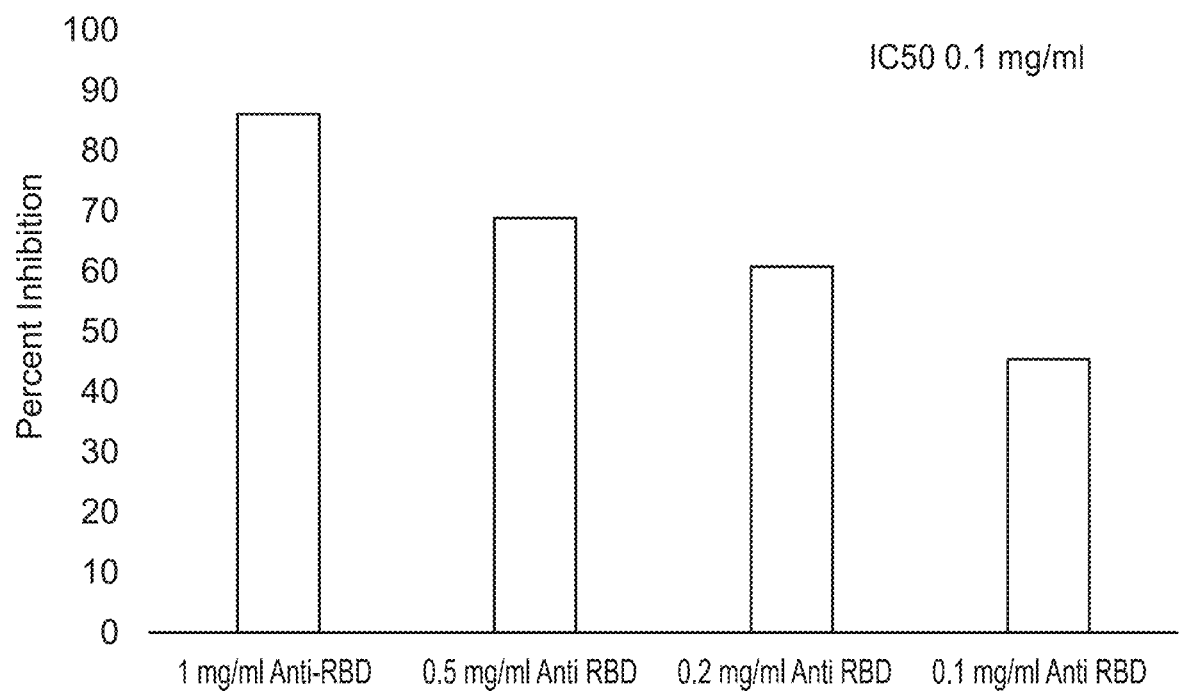
FIG. 3

Neutralization of SARS CoV-2 Virus - Wuhan Strain
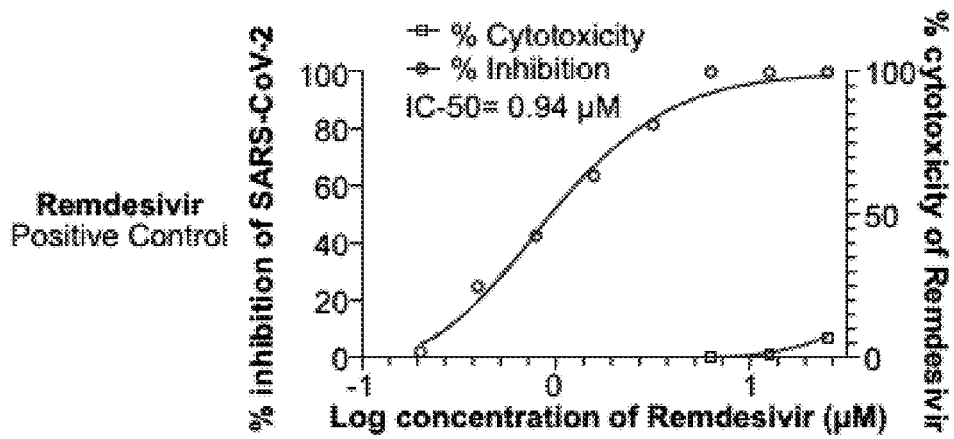
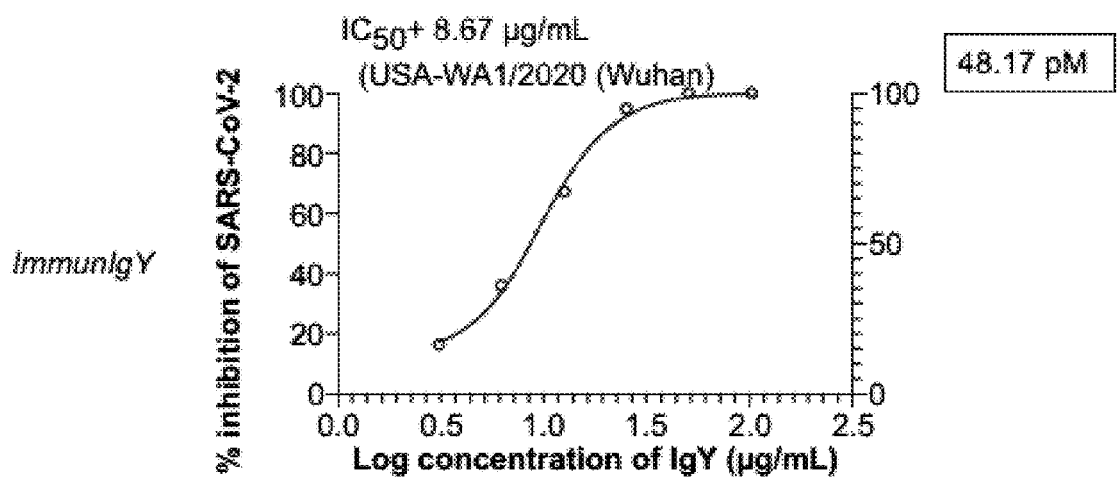
| ug IgY | uM | nM | pM |

SEQUENCE LISTING

```
<160> NUMBER OF SEQ ID NOS: 19

<210> SEQ ID NO 1
<211> LENGTH: 1273
<212> TYPE: PRT
<213> ORGANISM: SarsCoV2 virus
```

<400> SEQUENCE: 1

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
```

```
                    405                 410                 415
Lys Ile Ala Asp Tyr Asn Tyr Lys Leu Pro Asp Asp Phe Thr Gly Cys
                420                 425                 430

Val Ile Ala Trp Asn Ser Asn Asn Leu Asp Ser Lys Val Gly Gly Asn
                435                 440                 445

Tyr Asn Tyr Leu Tyr Arg Leu Phe Arg Lys Ser Asn Leu Lys Pro Phe
            450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
            515                 520                 525

Lys Ser Thr Asn Leu Val Lys Asn Lys Cys Val Asn Phe Asn Phe Asn
530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
            595                 600                 605

Ala Val Leu Tyr Gln Asp Val Asn Cys Thr Glu Val Pro Val Ala Ile
            610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
            675                 680                 685

Ser Gln Ser Ile Ile Ala Tyr Thr Met Ser Leu Gly Ala Glu Asn Ser
            690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
            755                 760                 765

Gly Ile Ala Val Glu Gln Asp Lys Asn Thr Gln Glu Val Phe Ala Gln
            770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830
```

```
Phe Ile Lys Gln Tyr Gly Asp Cys Leu Gly Asp Ile Ala Ala Arg Asp
    835                 840                 845

Leu Ile Cys Ala Gln Lys Phe Asn Gly Leu Thr Val Leu Pro Pro Leu
850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
                900                 905                 910

Gln Asn Val Leu Tyr Glu Asn Gln Lys Leu Ile Ala Asn Gln Phe Asn
                915                 920                 925

Ser Ala Ile Gly Lys Ile Gln Asp Ser Leu Ser Ser Thr Ala Ser Ala
                930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
                980                 985                 990

Ile Asp Arg Leu Ile Thr Gly Arg Leu Gln Ser Leu Gln Thr Tyr Val
                995                 1000                1005

Thr Gln Gln Leu Ile Arg Ala Ala Glu Ile Arg Ala Ser Ala Asn
    1010            1015                1020

Leu Ala Ala Thr Lys Met Ser Glu Cys Val Leu Gly Gln Ser Lys
    1025            1030                1035

Arg Val Asp Phe Cys Gly Lys Gly Tyr His Leu Met Ser Phe Pro
    1040            1045                1050

Gln Ser Ala Pro His Gly Val Phe Leu His Val Thr Tyr Val
    1055            1060                1065

Pro Ala Gln Glu Lys Asn Phe Thr Thr Ala Pro Ala Ile Cys His
    1070            1075                1080

Asp Gly Lys Ala His Phe Pro Arg Glu Gly Val Phe Val Ser Asn
    1085            1090                1095

Gly Thr His Trp Phe Val Thr Gln Arg Asn Phe Tyr Glu Pro Gln
    1100            1105                1110

Ile Ile Thr Thr Asp Asn Thr Phe Val Ser Gly Asn Cys Asp Val
    1115            1120                1125

Val Ile Gly Ile Val Asn Asn Thr Val Tyr Asp Pro Leu Gln Pro
    1130            1135                1140

Glu Leu Asp Ser Phe Lys Glu Glu Leu Asp Lys Tyr Phe Lys Asn
    1145            1150                1155

His Thr Ser Pro Asp Val Asp Leu Gly Asp Ile Ser Gly Ile Asn
    1160            1165                1170

Ala Ser Val Val Asn Ile Gln Lys Glu Ile Asp Arg Leu Asn Glu
    1175            1180                1185

Val Ala Lys Asn Leu Asn Glu Ser Leu Ile Asp Leu Gln Glu Leu
    1190            1195                1200

Gly Lys Tyr Glu Gln Tyr Ile Lys Trp Pro Trp Tyr Ile Trp Leu
    1205            1210                1215

Gly Phe Ile Ala Gly Leu Ile Ala Ile Val Met Val Thr Ile Met
    1220            1225                1230
```

```
Leu Cys Cys Met Thr Ser Cys Cys Ser Cys Leu Lys Gly Cys Cys
    1235                1240                1245

Ser Cys Gly Ser Cys Cys Lys Phe Asp Glu Asp Ser Glu Pro
    1250                1255                1260

Val Leu Lys Gly Val Lys Leu His Tyr Thr
    1265                1270

<210> SEQ ID NO 2
<211> LENGTH: 960
<212> TYPE: PRT
<213> ORGANISM: SarsCoV virus

<400> SEQUENCE: 2

Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
            20                  25                  30

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
    50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
    130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
        195                 200                 205

Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Ala Tyr Phe Val Gly Tyr
                245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
        275                 280                 285

Ser Val Lys Ser Phe Glu Ile Asp Lys Gly Ile Tyr Gln Thr Ser Asn
    290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335
```

```
Val Tyr Ala Trp Glu Arg Lys Lys Ile Ser Asn Cys Val Ala Asp Tyr
            340                 345                 350

Ser Val Leu Tyr Asn Ser Thr Phe Ser Thr Phe Lys Cys Tyr Gly
        355                 360                 365

Val Ser Ala Thr Lys Leu Asn Asp Leu Cys Phe Ser Asn Val Tyr Ala
        370                 375                 380

Asp Ser Phe Val Val Lys Gly Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
            420                 425                 430

Thr Gly Asn Tyr Asn Tyr Lys Tyr Arg Tyr Leu Arg His Gly Lys Leu
        435                 440                 445

Arg Pro Phe Glu Arg Asp Ile Ser Asn Val Pro Phe Ser Pro Asp Gly
    450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
            515                 520                 525

Phe Asn Gly Leu Thr Gly Thr Gly Val Leu Thr Pro Ser Ser Lys Arg
            530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ser Phe Gly Gly Val Ser Val Ile Thr Pro Gly Thr Asn Ala Ser Ser
            580                 585                 590

Glu Val Ala Val Leu Tyr Gln Asp Val Asn Cys Thr Asp Val Ser Thr
            595                 600                 605

Ala Ile His Ala Asp Gln Leu Thr Pro Ala Trp Arg Ile Tyr Ser Thr
            610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
            660                 665                 670

Ser Ile Val Ala Tyr Thr Met Ser Leu Gly Ala Asp Ser Ser Ile Ala
            675                 680                 685

Tyr Ser Asn Asn Thr Ile Ala Ile Pro Thr Asn Phe Ser Ile Ser Ile
            690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
            740                 745                 750
```

Ala Ala Glu Gln Asp Arg Asn Thr Arg Glu Val Phe Ala Gln Val Lys
            755                 760                 765

Gln Met Tyr Lys Thr Pro Thr Leu Lys Tyr Phe Gly Gly Phe Asn Phe
    770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
                820                 825                 830

Cys Ala Gln Lys Phe Asn Gly Leu Thr Val Leu Pro Pro Leu Leu Thr
            835                 840                 845

Asp Asp Met Ile Ala Ala Tyr Thr Ala Ala Leu Val Ser Gly Thr Ala
850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
            900                 905                 910

Ile Ser Gln Ile Gln Glu Ser Leu Thr Thr Thr Ser Thr Ala Leu Gly
        915                 920                 925

Lys Leu Gln Asp Val Val Asn Gln Asn Ala Gln Ala Leu Asn Thr Leu
            930                 935                 940

Val Lys Gln Leu Ser Ser Asn Phe Gly Ala Ile Ser Ser Val Leu Asn
945                 950                 955                 960

<210> SEQ ID NO 3
<211> LENGTH: 1353
<212> TYPE: PRT
<213> ORGANISM: MERS virus

<400> SEQUENCE: 3

Met Ile His Ser Val Phe Leu Leu Met Phe Leu Leu Thr Pro Thr Glu
1               5                   10                  15

Ser Tyr Val Asp Val Gly Pro Asp Ser Val Lys Ser Ala Cys Ile Glu
                20                  25                  30

Val Asp Ile Gln Gln Thr Phe Phe Asp Lys Thr Trp Pro Arg Pro Ile
            35                  40                  45

Asp Val Ser Lys Ala Asp Gly Ile Ile Tyr Pro Gln Gly Arg Thr Tyr
        50                  55                  60

Ser Asn Ile Thr Ile Thr Tyr Gln Gly Leu Phe Pro Tyr Gln Gly Asp
65                  70                  75                  80

His Gly Asp Met Tyr Val Tyr Ser Ala Gly His Ala Thr Gly Thr Thr
                85                  90                  95

Pro Gln Lys Leu Phe Val Ala Asn Tyr Ser Gln Asp Val Lys Gln Phe
            100                 105                 110

Ala Asn Gly Phe Val Val Arg Ile Gly Ala Ala Ala Asn Ser Thr Gly
        115                 120                 125

Thr Val Ile Ile Ser Pro Ser Thr Ser Ala Thr Ile Arg Lys Ile Tyr
    130                 135                 140

Pro Ala Phe Met Leu Gly Ser Ser Val Gly Asn Phe Ser Asp Gly Lys
145                 150                 155                 160

Met Gly Arg Phe Phe Asn His Thr Leu Val Leu Leu Pro Asp Gly Cys
                165                 170                 175

```
Gly Thr Leu Leu Arg Ala Phe Tyr Cys Ile Leu Glu Pro Arg Ser Gly
            180                 185                 190

Asn His Cys Pro Ala Gly Asn Ser Tyr Thr Ser Phe Ala Thr Tyr His
            195                 200                 205

Thr Pro Ala Thr Asp Cys Ser Asp Gly Asn Tyr Asn Arg Asn Ala Ser
210                 215                 220

Leu Asn Ser Phe Lys Glu Tyr Phe Asn Leu Arg Asn Cys Thr Phe Met
225                 230                 235                 240

Tyr Thr Tyr Asn Ile Thr Glu Asp Glu Ile Leu Glu Trp Phe Gly Ile
            245                 250                 255

Thr Gln Thr Ala Gln Gly Val His Leu Phe Ser Ser Arg Tyr Val Asp
            260                 265                 270

Leu Tyr Gly Gly Asn Met Phe Gln Phe Ala Thr Leu Pro Val Tyr Asp
            275                 280                 285

Thr Ile Lys Tyr Tyr Ser Ile Ile Pro His Ser Ile Arg Ser Ile Gln
            290                 295                 300

Ser Asp Arg Lys Ala Trp Ala Ala Phe Tyr Val Tyr Lys Leu Gln Pro
305                 310                 315                 320

Leu Thr Phe Leu Leu Asp Phe Ser Val Asp Gly Tyr Ile Arg Arg Ala
            325                 330                 335

Ile Asp Cys Gly Phe Asn Asp Leu Ser Gln Leu His Cys Ser Tyr Glu
            340                 345                 350

Ser Phe Asp Val Glu Ser Gly Val Tyr Ser Val Ser Ser Phe Glu Ala
            355                 360                 365

Lys Pro Ser Gly Ser Val Val Glu Gln Ala Glu Gly Val Glu Cys Asp
            370                 375                 380

Phe Ser Pro Leu Leu Ser Gly Thr Pro Pro Gln Val Tyr Asn Phe Lys
385                 390                 395                 400

Arg Leu Val Phe Thr Asn Cys Asn Tyr Asn Leu Thr Lys Leu Leu Ser
            405                 410                 415

Leu Phe Ser Val Asn Asp Phe Thr Cys Ser Gln Ile Ser Pro Ala Ala
            420                 425                 430

Ile Ala Ser Asn Cys Tyr Ser Ser Leu Ile Leu Asp Tyr Phe Ser Tyr
            435                 440                 445

Pro Leu Ser Met Lys Ser Asp Leu Ser Val Ser Ser Ala Gly Pro Ile
450                 455                 460

Ser Gln Phe Asn Tyr Lys Gln Ser Phe Ser Asn Pro Thr Cys Leu Ile
465                 470                 475                 480

Leu Ala Thr Val Pro His Asn Leu Thr Thr Ile Thr Lys Pro Leu Lys
            485                 490                 495

Tyr Ser Tyr Ile Asn Lys Cys Ser Arg Phe Leu Ser Asp Asp Arg Thr
            500                 505                 510

Glu Val Pro Gln Leu Val Asn Ala Asn Gln Tyr Ser Pro Cys Val Ser
            515                 520                 525

Ile Val Pro Ser Thr Val Trp Glu Asp Gly Asp Tyr Tyr Arg Lys Gln
            530                 535                 540

Leu Ser Pro Leu Glu Gly Gly Gly Trp Leu Val Ala Ser Gly Ser Thr
545                 550                 555                 560

Val Ala Met Thr Glu Gln Leu Gln Met Gly Phe Gly Ile Thr Val Gln
            565                 570                 575

Tyr Gly Thr Asp Thr Asn Ser Val Cys Pro Lys Leu Glu Phe Ala Asn
            580                 585                 590
```

```
Asp Thr Lys Ile Ala Ser Gln Leu Gly Asn Cys Val Glu Tyr Ser Leu
            595                 600                 605

Tyr Gly Val Ser Gly Arg Gly Val Phe Gln Asn Cys Thr Ala Val Gly
        610                 615                 620

Val Arg Gln Gln Arg Phe Val Tyr Asp Ala Tyr Gln Asn Leu Val Gly
625                 630                 635                 640

Tyr Tyr Ser Asp Asp Gly Asn Tyr Tyr Cys Leu Arg Ala Cys Val Ser
                645                 650                 655

Val Pro Val Ser Val Ile Tyr Asp Lys Glu Thr Lys Thr His Ala Thr
            660                 665                 670

Leu Phe Gly Ser Val Ala Cys Glu His Ile Ser Ser Thr Met Ser Gln
        675                 680                 685

Tyr Ser Arg Ser Thr Arg Ser Met Leu Lys Arg Arg Asp Ser Thr Tyr
    690                 695                 700

Gly Pro Leu Gln Thr Pro Val Gly Cys Val Leu Gly Leu Val Asn Ser
705                 710                 715                 720

Ser Leu Phe Val Glu Asp Cys Lys Leu Pro Leu Gly Gln Ser Leu Cys
                725                 730                 735

Ala Leu Pro Asp Thr Pro Ser Thr Leu Thr Pro Arg Ser Val Arg Ser
            740                 745                 750

Val Pro Gly Glu Met Arg Leu Ala Ser Ile Ala Phe Asn His Pro Ile
        755                 760                 765

Gln Val Asp Gln Leu Asn Ser Ser Tyr Phe Lys Leu Ser Ile Pro Thr
    770                 775                 780

Asn Phe Ser Phe Gly Val Thr Gln Glu Tyr Ile Gln Thr Thr Ile Gln
785                 790                 795                 800

Lys Val Thr Val Asp Cys Lys Gln Tyr Val Cys Asn Gly Phe Gln Lys
                805                 810                 815

Cys Glu Gln Leu Leu Arg Glu Tyr Gly Gln Phe Cys Ser Lys Ile Asn
            820                 825                 830

Gln Ala Leu His Gly Ala Asn Leu Arg Gln Asp Asp Ser Val Arg Asn
        835                 840                 845

Leu Phe Ala Ser Val Lys Ser Ser Gln Ser Ser Pro Ile Ile Pro Gly
    850                 855                 860

Phe Gly Gly Asp Phe Asn Leu Thr Leu Leu Glu Pro Val Ser Ile Ser
865                 870                 875                 880

Thr Gly Ser Arg Ser Ala Arg Ser Ala Ile Glu Asp Leu Leu Phe Asp
                885                 890                 895

Lys Val Thr Ile Ala Asp Pro Gly Tyr Met Gln Gly Tyr Asp Asp Cys
            900                 905                 910

Met Gln Gln Gly Pro Ala Ser Ala Arg Asp Leu Ile Cys Ala Gln Tyr
        915                 920                 925

Val Ala Gly Tyr Lys Val Leu Pro Pro Leu Met Asp Val Asn Met Glu
    930                 935                 940

Ala Ala Tyr Thr Ser Ser Leu Leu Gly Ser Ile Ala Gly Val Gly Trp
945                 950                 955                 960

Thr Ala Gly Leu Ser Ser Phe Ala Ala Ile Pro Phe Ala Gln Ser Ile
                965                 970                 975

Phe Tyr Arg Leu Asn Gly Val Gly Ile Thr Gln Gln Val Leu Ser Glu
            980                 985                 990

Asn Gln Lys Leu Ile Ala Asn Lys Phe Asn Gln Ala Leu Gly Ala Met
        995                 1000                1005

Gln Thr  Gly Phe Thr Thr Thr  Asn Glu Ala Phe His  Lys Val Gln
```

```
              1010                1015                1020

Asp Ala Val Asn Asn Ala Gln Ala Leu Ser Lys Leu Ala Ser
        1025                1030                1035

Glu Leu Ser Asn Thr Phe Gly Ala Ile Ser Ala Ser Ile Gly Asp
    1040                1045                1050

Ile Ile Gln Arg Leu Asp Val Leu Glu Gln Asp Ala Gln Ile Asp
    1055                1060                1065

Arg Leu Ile Asn Gly Arg Leu Thr Thr Leu Asn Ala Phe Val Ala
    1070                1075                1080

Gln Gln Leu Val Arg Ser Glu Ser Ala Ala Leu Ser Ala Gln Leu
    1085                1090                1095

Ala Lys Asp Lys Val Asn Glu Cys Val Lys Ala Gln Ser Lys Arg
    1100                1105                1110

Ser Gly Phe Cys Gly Gln Gly Thr His Ile Val Ser Phe Val Val
    1115                1120                1125

Asn Ala Pro Asn Gly Leu Tyr Phe Met His Val Gly Tyr Tyr Pro
    1130                1135                1140

Ser Asn His Ile Glu Val Val Ser Ala Tyr Gly Leu Cys Asp Ala
    1145                1150                1155

Ala Asn Pro Thr Asn Cys Ile Ala Pro Val Asn Gly Tyr Phe Ile
    1160                1165                1170

Lys Thr Asn Asn Thr Arg Ile Val Asp Glu Trp Ser Tyr Thr Gly
    1175                1180                1185

Ser Ser Phe Tyr Ala Pro Glu Pro Ile Thr Ser Leu Asn Thr Lys
    1190                1195                1200

Tyr Val Ala Pro Gln Val Thr Tyr Gln Asn Ile Ser Thr Asn Leu
    1205                1210                1215

Pro Pro Pro Leu Leu Gly Asn Ser Thr Gly Ile Asp Phe Gln Asp
    1220                1225                1230

Glu Leu Asp Glu Phe Phe Lys Asn Val Ser Thr Ser Ile Pro Asn
    1235                1240                1245

Phe Gly Ser Leu Thr Gln Ile Asn Thr Thr Leu Leu Asp Leu Thr
    1250                1255                1260

Tyr Glu Met Leu Ser Leu Gln Gln Val Val Lys Ala Leu Asn Glu
    1265                1270                1275

Ser Tyr Ile Asp Leu Lys Glu Leu Gly Asn Tyr Thr Tyr Tyr Asn
    1280                1285                1290

Lys Trp Pro Trp Tyr Ile Trp Leu Gly Phe Ile Ala Gly Leu Val
    1295                1300                1305

Ala Leu Ala Leu Cys Val Phe Phe Ile Leu Cys Cys Thr Gly Cys
    1310                1315                1320

Gly Thr Asn Cys Met Gly Lys Leu Lys Cys Asn Arg Cys Cys Asp
    1325                1330                1335

Arg Tyr Glu Glu Tyr Asp Leu Glu Pro His Lys Val His Val His
    1340                1345                1350
```

<210> SEQ ID NO 4
<211> LENGTH: 1351
<212> TYPE: PRT
<213> ORGANISM: HKU1 virus

<400> SEQUENCE: 4

```
Met Phe Leu Ile Ile Phe Ile Leu Pro Thr Thr Leu Ala Val Ile Gly
1               5                   10                  15
```

-continued

```
Asp Phe Asn Cys Thr Asn Ser Phe Ile Asn Asp Tyr Asn Lys Thr Ile
             20                  25                  30

Pro Arg Ile Ser Glu Asp Val Val Asp Val Ser Leu Gly Leu Gly Thr
         35                  40                  45

Tyr Tyr Val Leu Asn Arg Val Tyr Leu Asn Thr Thr Leu Leu Phe Thr
     50                  55                  60

Gly Tyr Phe Pro Lys Ser Gly Ala Asn Phe Arg Asp Leu Ala Leu Lys
65                  70                  75                  80

Gly Ser Ile Tyr Leu Ser Thr Leu Trp Tyr Lys Pro Pro Phe Leu Ser
                 85                  90                  95

Asp Phe Asn Asn Gly Ile Phe Ser Lys Val Lys Asn Thr Lys Leu Tyr
             100                 105                 110

Val Asn Asn Thr Leu Tyr Ser Glu Phe Ser Thr Ile Val Ile Gly Ser
         115                 120                 125

Val Phe Val Asn Thr Ser Tyr Thr Ile Val Val Gln Pro His Asn Gly
     130                 135                 140

Ile Leu Glu Ile Thr Ala Cys Gln Tyr Thr Met Cys Glu Tyr Pro His
145                 150                 155                 160

Thr Val Cys Lys Ser Lys Gly Ser Ile Arg Asn Glu Ser Trp His Ile
                 165                 170                 175

Asp Ser Ser Glu Pro Leu Cys Leu Phe Lys Lys Asn Phe Thr Tyr Asn
             180                 185                 190

Val Ser Ala Asp Trp Leu Tyr Phe His Phe Tyr Gln Glu Arg Gly Val
         195                 200                 205

Phe Tyr Ala Tyr Tyr Ala Asp Val Gly Met Pro Thr Thr Phe Leu Phe
     210                 215                 220

Ser Leu Tyr Leu Gly Thr Ile Leu Ser His Tyr Tyr Val Met Pro Leu
225                 230                 235                 240

Thr Cys Asn Ala Ile Ser Ser Asn Thr Asp Asn Glu Thr Leu Glu Tyr
                 245                 250                 255

Trp Val Thr Pro Leu Ser Arg Arg Gln Tyr Leu Leu Asn Phe Asp Glu
             260                 265                 270

His Gly Val Ile Thr Asn Ala Val Asp Cys Ser Ser Ser Phe Leu Ser
         275                 280                 285

Glu Ile Gln Cys Lys Thr Gln Ser Phe Ala Pro Asn Thr Gly Val Tyr
     290                 295                 300

Asp Leu Ser Gly Phe Thr Val Lys Pro Val Ala Thr Val Tyr Arg Arg
305                 310                 315                 320

Ile Pro Asn Leu Pro Asp Cys Asp Ile Asp Asn Trp Leu Asn Asn Val
                 325                 330                 335

Ser Val Pro Ser Pro Leu Asn Trp Glu Arg Arg Ile Phe Ser Asn Cys
             340                 345                 350

Asn Phe Asn Leu Ser Thr Leu Leu Arg Leu Val His Val Asp Ser Phe
         355                 360                 365

Ser Cys Asn Asn Leu Asp Lys Ser Lys Ile Phe Gly Ser Cys Phe Asn
     370                 375                 380

Ser Ile Thr Val Asp Lys Phe Ala Ile Pro Asn Arg Arg Arg Asp Asp
385                 390                 395                 400

Leu Gln Leu Gly Ser Ser Gly Phe Leu Gln Ser Ser Asn Tyr Lys Ile
                 405                 410                 415

Asp Ile Ser Ser Ser Ser Cys Gln Leu Tyr Tyr Ser Leu Pro Leu Val
             420                 425                 430

Asn Val Thr Ile Asn Asn Phe Asn Pro Ser Ser Trp Asn Arg Arg Tyr
```

```
            435                 440                 445
Gly Phe Gly Ser Phe Asn Val Ser Ser Tyr Asp Val Val Tyr Ser Asp
    450                 455                 460

His Cys Phe Ser Val Asn Ser Asp Phe Cys Pro Cys Ala Asp Arg Ser
465                 470                 475                 480

Val Val Asn Ser Cys Val Lys Ser Lys Pro Pro Ser Ala Ile Cys Pro
                485                 490                 495

Ala Gly Thr Lys Tyr Arg His Cys Asp Leu Asp Thr Thr Leu Tyr Val
            500                 505                 510

Lys Asn Trp Cys Arg Cys Ser Cys Leu Pro Asp Pro Ile Ser Thr Tyr
        515                 520                 525

Ser Pro Asn Thr Cys Pro Gln Lys Lys Val Val Gly Ile Gly Glu
    530                 535                 540

His Cys Pro Gly Leu Gly Ile Asn Glu Glu Lys Cys Gly Thr Gln Leu
545                 550                 555                 560

Asn His Ser Ser Cys Ser Cys Ser Pro Asp Ala Phe Leu Gly Trp Ser
                565                 570                 575

Phe Asp Ser Cys Ile Ser Asn Asn Arg Cys Asn Ile Phe Ser Asn Phe
            580                 585                 590

Ile Phe Asn Gly Ile Asn Ser Gly Thr Thr Cys Ser Asn Asp Leu Leu
        595                 600                 605

Tyr Ser Asn Thr Glu Val Ser Thr Gly Val Cys Val Asn Tyr Asp Leu
    610                 615                 620

Tyr Gly Ile Thr Gly Gln Gly Ile Phe Lys Glu Val Ser Ala Ala Tyr
625                 630                 635                 640

Tyr Asn Asn Trp Gln Asn Leu Leu Tyr Asp Ser Asn Gly Asn Ile Ile
                645                 650                 655

Gly Phe Lys Asp Phe Leu Thr Asn Lys Thr Tyr Thr Ile Leu Pro Cys
            660                 665                 670

Tyr Ser Gly Arg Val Ser Ala Ala Phe Tyr Gln Asn Ser Ser Pro
        675                 680                 685

Ala Leu Leu Tyr Arg Asn Leu Lys Cys Ser Tyr Val Leu Asn Asn Ile
    690                 695                 700

Ser Phe Ile Ser Gln Pro Phe Tyr Phe Asp Ser Tyr Leu Gly Cys Val
705                 710                 715                 720

Leu Asn Ala Val Asn Leu Thr Ser Tyr Ser Val Ser Ser Cys Asp Leu
                725                 730                 735

Arg Met Gly Ser Gly Phe Cys Ile Asp Tyr Ala Leu Pro Ser Ser Arg
            740                 745                 750

Arg Lys Arg Arg Gly Ile Ser Ser Pro Tyr Arg Phe Val Thr Phe Glu
        755                 760                 765

Pro Phe Asn Val Ser Phe Val Asn Asp Ser Val Glu Thr Val Gly Gly
    770                 775                 780

Leu Phe Glu Ile Gln Ile Pro Thr Asn Phe Thr Ile Ala Gly His Glu
785                 790                 795                 800

Glu Phe Ile Gln Thr Ser Ser Pro Lys Val Thr Ile Asp Cys Ser Ala
                805                 810                 815

Phe Val Cys Ser Asn Tyr Ala Ala Cys His Asp Leu Leu Ser Glu Tyr
            820                 825                 830

Gly Thr Phe Cys Asp Asn Ile Asn Ser Ile Leu Asn Glu Val Asn Asp
        835                 840                 845

Leu Leu Asp Ile Thr Gln Leu Gln Val Ala Asn Ala Leu Met Gln Gly
    850                 855                 860
```

```
Val Thr Leu Ser Ser Asn Leu Asn Thr Asn Leu His Ser Asp Val Asp
865                 870                 875                 880

Asn Ile Asp Phe Lys Ser Leu Leu Gly Cys Leu Gly Ser Gln Cys Gly
                885                 890                 895

Ser Ser Ser Arg Ser Leu Leu Glu Asp Leu Leu Phe Asn Lys Val Lys
            900                 905                 910

Leu Ser Asp Val Gly Phe Val Glu Ala Tyr Asn Asn Cys Thr Gly Gly
        915                 920                 925

Ser Glu Ile Arg Asp Leu Leu Cys Val Gln Ser Phe Asn Gly Ile Lys
    930                 935                 940

Val Leu Pro Pro Ile Leu Ser Glu Thr Gln Ile Ser Gly Tyr Thr Thr
945                 950                 955                 960

Ala Ala Thr Val Ala Ala Met Phe Pro Pro Trp Ser Ala Ala Ala Gly
                965                 970                 975

Val Pro Phe Ser Leu Asn Val Gln Tyr Arg Ile Asn Gly Leu Gly Val
            980                 985                 990

Thr Met Asp Val Leu Asn Lys Asn Gln Lys Leu Ile Ala Asn Ala Phe
        995                 1000                1005

Asn Lys Ala Leu Leu Ser Ile Gln Asn Gly Phe Thr Ala Thr Asn
    1010                1015                1020

Ser Ala Leu Ala Lys Ile Gln Ser Val Val Asn Ala Asn Ala Gln
    1025                1030                1035

Ala Leu Asn Ser Leu Leu Gln Gln Leu Phe Asn Lys Phe Gly Ala
    1040                1045                1050

Ile Ser Ser Ser Leu Gln Glu Ile Leu Ser Arg Leu Asp Asn Leu
    1055                1060                1065

Glu Ala Gln Val Gln Ile Asp Arg Leu Ile Asn Gly Arg Leu Thr
    1070                1075                1080

Ala Leu Asn Ala Tyr Val Ser Gln Gln Leu Ser Asp Ile Thr Leu
    1085                1090                1095

Ile Lys Ala Gly Ala Ser Arg Ala Ile Glu Lys Val Asn Glu Cys
    1100                1105                1110

Val Lys Ser Gln Ser Pro Arg Ile Asn Phe Cys Gly Asn Gly Asn
    1115                1120                1125

His Ile Leu Ser Leu Val Gln Asn Ala Pro Tyr Gly Leu Leu Phe
    1130                1135                1140

Ile His Phe Ser Tyr Lys Pro Thr Ser Phe Lys Thr Val Leu Val
    1145                1150                1155

Ser Pro Gly Leu Cys Leu Ser Gly Asp Arg Gly Ile Ala Pro Lys
    1160                1165                1170

Gln Gly Tyr Phe Ile Lys Gln Asn Asp Ser Trp Met Phe Thr Gly
    1175                1180                1185

Ser Ser Tyr Tyr Tyr Pro Glu Pro Ile Ser Asp Lys Asn Val Val
    1190                1195                1200

Phe Met Asn Ser Cys Ser Val Asn Phe Thr Lys Ala Pro Phe Ile
    1205                1210                1215

Tyr Leu Asn Asn Ser Ile Pro Asn Leu Ser Asp Phe Glu Ala Glu
    1220                1225                1230

Phe Ser Leu Trp Phe Lys Asn His Thr Ser Ile Ala Pro Asn Leu
    1235                1240                1245

Thr Phe Asn Ser His Ile Asn Ala Thr Phe Leu Asp Leu Tyr Tyr
    1250                1255                1260
```

```
Glu Met Asn Val Ile Gln Glu Ser Ile Lys Ser Leu Asn Ser Ser
    1265                1270                1275

Phe Ile Asn Leu Lys Glu Ile Gly Thr Tyr Glu Met Tyr Val Lys
    1280                1285                1290

Trp Pro Trp Tyr Ile Trp Leu Leu Ile Val Ile Leu Phe Ile Ile
    1295                1300                1305

Phe Leu Met Ile Leu Phe Phe Ile Cys Cys Cys Thr Gly Cys Gly
    1310                1315                1320

Ser Ala Cys Phe Ser Lys Cys His Asn Cys Cys Asp Glu Tyr Gly
    1325                1330                1335

Gly His Asn Asp Phe Val Ile Lys Ala Ser His Asp Asp
    1340                1345                1350

<210> SEQ ID NO 5
<211> LENGTH: 1356
<212> TYPE: PRT
<213> ORGANISM: NL63 virus

<400> SEQUENCE: 5

Met Lys Leu Phe Leu Ile Leu Val Leu Pro Leu Ala Ser Cys Phe
1               5                   10                  15

Phe Thr Cys Asn Ser Asn Ala Asn Leu Ser Met Leu Gln Leu Gly Val
                20                  25                  30

Pro Asp Asn Ser Ser Thr Ile Val Thr Gly Leu Leu Pro Thr His Trp
                35                  40                  45

Phe Cys Ala Asn Gln Ser Thr Ser Val Tyr Ser Ala Asn Gly Phe Phe
        50                  55                  60

Tyr Ile Asp Val Gly Asn His Arg Ser Ala Phe Ala Leu His Thr Gly
65                  70                  75                  80

Tyr Tyr Asp Ala Asn Gln Tyr Tyr Ile Tyr Val Thr Asn Glu Ile Gly
                85                  90                  95

Leu Asn Ala Ser Val Thr Leu Lys Ile Cys Lys Phe Ser Arg Asn Thr
                100                 105                 110

Thr Phe Asp Phe Leu Ser Asn Ala Ser Ser Ser Phe Asp Cys Ile Val
            115                 120                 125

Asn Leu Leu Phe Thr Glu Gln Leu Gly Ala Pro Leu Gly Ile Thr Ile
        130                 135                 140

Ser Gly Glu Thr Val Arg Leu His Leu Tyr Asn Val Thr Arg Thr Phe
145                 150                 155                 160

Tyr Val Pro Ala Ala Tyr Lys Leu Thr Lys Leu Ser Val Lys Cys Tyr
                165                 170                 175

Phe Asn Tyr Ser Cys Val Phe Ser Val Val Asn Ala Thr Val Thr Val
                180                 185                 190

Asn Val Thr Thr His Asn Gly Arg Val Val Asn Tyr Thr Val Cys Asp
            195                 200                 205

Asp Cys Asn Gly Tyr Thr Asp Asn Ile Phe Ser Val Gln Gln Asp Gly
        210                 215                 220

Arg Ile Pro Asn Gly Phe Pro Phe Asn Asn Trp Phe Leu Leu Thr Asn
225                 230                 235                 240

Gly Ser Thr Leu Val Asp Gly Val Ser Arg Leu Tyr Gln Pro Leu Arg
                245                 250                 255

Leu Thr Cys Leu Trp Pro Val Pro Gly Leu Lys Ser Ser Thr Gly Phe
                260                 265                 270

Val Tyr Phe Asn Ala Thr Gly Ser Asp Val Asn Cys Asn Gly Tyr Gln
            275                 280                 285
```

```
His Asn Ser Val Val Asp Val Met Arg Tyr Asn Leu Asn Phe Ser Ala
    290                 295                 300
Asn Ser Leu Asp Asn Leu Lys Ser Gly Val Ile Val Phe Lys Thr Leu
305                 310                 315                 320
Gln Tyr Asp Val Leu Phe Tyr Cys Ser Asn Ser Ser Ser Gly Val Leu
                325                 330                 335
Asp Thr Thr Ile Pro Phe Gly Pro Ser Ser Gln Pro Tyr Tyr Cys Phe
            340                 345                 350
Ile Asn Ser Thr Ile Asn Thr Thr His Val Ser Thr Phe Val Gly Ile
        355                 360                 365
Leu Pro Pro Thr Val Arg Glu Ile Val Val Ala Arg Thr Gly Gln Phe
    370                 375                 380
Tyr Ile Asn Gly Phe Lys Tyr Phe Asp Leu Gly Phe Ile Glu Ala Val
385                 390                 395                 400
Asn Phe Asn Val Thr Thr Ala Ser Ala Thr Asp Phe Trp Thr Val Ala
                405                 410                 415
Phe Ala Thr Phe Val Asp Val Leu Val Asn Val Ser Ala Thr Asn Ile
            420                 425                 430
Gln Asn Leu Leu Tyr Cys Asp Ser Pro Phe Glu Lys Leu Gln Cys Glu
        435                 440                 445
His Leu Gln Phe Gly Leu Gln Asp Gly Phe Tyr Ser Ala Asn Phe Leu
    450                 455                 460
Asp Asp Asn Val Leu Pro Glu Thr Tyr Val Ala Leu Pro Ile Tyr Tyr
465                 470                 475                 480
Gln His Thr Asp Ile Asn Phe Thr Ala Thr Ala Ser Phe Gly Gly Ser
                485                 490                 495
Cys Tyr Val Cys Lys Pro His Gln Val Asn Ile Ser Leu Asn Gly Asn
            500                 505                 510
Thr Ser Val Cys Val Arg Thr Ser His Phe Ser Ile Arg Tyr Ile Tyr
        515                 520                 525
Asn Arg Val Lys Ser Gly Ser Pro Gly Asp Ser Ser Trp His Ile Tyr
    530                 535                 540
Leu Lys Ser Gly Thr Cys Pro Phe Ser Phe Ser Lys Leu Asn Asn Phe
545                 550                 555                 560
Gln Lys Phe Lys Thr Ile Cys Phe Ser Thr Val Glu Val Pro Gly Ser
                565                 570                 575
Cys Asn Phe Pro Leu Glu Ala Thr Trp His Tyr Thr Ser Tyr Thr Ile
            580                 585                 590
Val Gly Ala Leu Tyr Val Thr Trp Ser Glu Gly Asn Ser Ile Thr Gly
        595                 600                 605
Val Pro Tyr Pro Val Ser Gly Ile Arg Glu Phe Ser Asn Leu Val Leu
    610                 615                 620
Asn Asn Cys Thr Lys Tyr Asn Ile Tyr Asp Tyr Val Gly Thr Gly Ile
625                 630                 635                 640
Ile Arg Ser Ser Asn Gln Ser Leu Ala Gly Gly Ile Thr Tyr Val Ser
                645                 650                 655
Asn Ser Gly Asn Leu Leu Gly Phe Lys Asn Val Ser Thr Gly Asn Ile
            660                 665                 670
Phe Ile Val Thr Pro Cys Asn Gln Pro Asp Gln Val Ala Val Tyr Gln
        675                 680                 685
Gln Ser Ile Ile Gly Ala Met Thr Ala Val Asn Glu Ser Arg Tyr Gly
    690                 695                 700
```

-continued

Leu Gln Asn Leu Leu Gln Leu Pro Asn Phe Tyr Tyr Val Ser Asn Gly
705                 710                 715                 720

Gly Asn Asn Cys Thr Thr Ala Val Met Thr Tyr Ser Asn Phe Gly Ile
        725                 730                 735

Cys Ala Asp Gly Ser Leu Ile Pro Val Arg Pro Arg Asn Ser Ser Asp
            740                 745                 750

Asn Gly Ile Ser Ala Ile Ile Thr Ala Asn Leu Ser Ile Pro Ser Asn
        755                 760                 765

Trp Thr Thr Ser Val Gln Val Glu Tyr Leu Gln Ile Thr Ser Thr Pro
    770                 775                 780

Ile Val Val Asp Cys Ala Thr Tyr Val Cys Asn Gly Asn Pro Arg Cys
785                 790                 795                 800

Lys Asn Leu Leu Lys Gln Tyr Thr Ser Ala Cys Lys Thr Ile Glu Asp
            805                 810                 815

Ala Leu Arg Leu Ser Ala His Leu Glu Thr Asn Asp Val Ser Ser Met
        820                 825                 830

Leu Thr Phe Asp Ser Asn Ala Phe Ser Leu Ala Asn Val Thr Ser Phe
    835                 840                 845

Gly Asp Tyr Asn Leu Ser Ser Val Leu Pro Gln Arg Asn Ile Arg Ser
850                 855                 860

Ser Arg Ile Ala Gly Arg Ser Ala Leu Glu Asp Leu Leu Phe Ser Lys
865                 870                 875                 880

Val Val Thr Ser Gly Leu Gly Thr Val Asp Val Asp Tyr Lys Ser Cys
            885                 890                 895

Thr Lys Gly Leu Ser Ile Ala Asp Leu Ala Cys Ala Gln Tyr Tyr Asn
        900                 905                 910

Gly Ile Met Val Leu Pro Gly Val Ala Asp Ala Glu Arg Met Ala Met
    915                 920                 925

Tyr Thr Gly Ser Leu Ile Gly Gly Met Val Leu Gly Gly Leu Thr Ser
930                 935                 940

Ala Ala Ala Ile Pro Phe Ser Leu Ala Leu Gln Ala Arg Leu Asn Tyr
945                 950                 955                 960

Val Ala Leu Gln Thr Asp Val Leu Gln Glu Asn Gln Lys Ile Leu Ala
            965                 970                 975

Ala Ser Phe Asn Lys Ala Ile Asn Asn Ile Val Ala Ser Phe Ser Ser
        980                 985                 990

Val Asn Asp Ala Ile Thr Gln Thr Ala Glu Ala Ile His Thr Val Thr
    995                 1000                1005

Ile Ala Leu Asn Lys Ile Gln Asp Val Val Asn Gln Gln Gly Ser
    1010                1015                1020

Ala Leu Asn His Leu Thr Ser Gln Leu Arg His Asn Phe Gln Ala
    1025                1030                1035

Ile Ser Asn Ser Ile Gln Ala Ile Tyr Asp Arg Leu Asp Ser Ile
    1040                1045                1050

Gln Ala Asp Gln Gln Val Asp Arg Leu Ile Thr Gly Arg Leu Ala
    1055                1060                1065

Ala Leu Asn Ala Phe Val Ser Gln Val Leu Asn Lys Tyr Thr Glu
    1070                1075                1080

Val Arg Gly Ser Arg Arg Leu Ala Gln Gln Lys Ile Asn Glu Cys
    1085                1090                1095

Val Lys Ser Gln Ser Asn Arg Tyr Gly Phe Cys Gly Asn Gly Thr
    1100                1105                1110

His Ile Phe Ser Ile Val Asn Ser Ala Pro Asp Gly Leu Leu Phe

```
                    1115                 1120                1125

Leu His  Thr Val Leu Leu Pro  Thr Asp Tyr Lys Asn  Val Lys Ala
    1130                 1135                1140

Trp Ser  Gly Ile Cys Val Asp  Gly Ile Tyr Gly Tyr  Val Leu Arg
    1145                 1150                1155

Gln Pro  Asn Leu Val Leu Tyr  Ser Asp Asn Gly Val  Phe Arg Val
    1160                 1165                1170

Thr Ser  Arg Val Met Phe Gln  Pro Arg Leu Pro Val  Leu Ser Asp
    1175                 1180                1185

Phe Val  Gln Ile Tyr Asn Cys  Asn Val Thr Phe Val  Asn Ile Ser
    1190                 1195                1200

Arg Val  Glu Leu His Thr Val  Ile Pro Asp Tyr Val  Asp Val Asn
    1205                 1210                1215

Lys Thr  Leu Gln Glu Phe Ala  Gln Asn Leu Pro Lys  Tyr Val Lys
    1220                 1225                1230

Pro Asn  Phe Asp Leu Thr Pro  Phe Asn Leu Thr Tyr  Leu Asn Leu
    1235                 1240                1245

Ser Ser  Glu Leu Lys Gln Leu  Glu Ala Lys Thr Ala  Ser Leu Phe
    1250                 1255                1260

Gln Thr  Thr Val Glu Leu Gln  Gly Leu Ile Asp Gln  Ile Asn Ser
    1265                 1270                1275

Thr Tyr  Val Asp Leu Lys Leu  Leu Asn Arg Phe Glu  Asn Tyr Ile
    1280                 1285                1290

Lys Trp  Pro Trp Trp Val Trp  Leu Ile Ile Ser Val  Val Phe Val
    1295                 1300                1305

Val Leu  Leu Ser Leu Leu Val  Phe Cys Cys Leu Ser  Thr Gly Cys
    1310                 1315                1320

Cys Gly  Cys Cys Asn Cys Leu  Thr Ser Ser Met Arg  Gly Cys Cys
    1325                 1330                1335

Asp Cys  Gly Ser Thr Lys Leu  Pro Tyr Tyr Glu Phe  Glu Lys Val
    1340                 1345                1350

His Val  Gln
    1355

<210> SEQ ID NO 6
<211> LENGTH: 1353
<212> TYPE: PRT
<213> ORGANISM: OC43 virus

<400> SEQUENCE: 6

Met Phe Leu Ile Leu Leu Ile Ser Leu Pro Thr Ala Phe Ala Val Ile
1               5                   10                  15

Gly Asp Leu Lys Cys Thr Ser Asp Asn Ile Asn Asp Lys Asp Thr Gly
            20                  25                  30

Pro Pro Pro Ile Ser Thr Asp Thr Val Asp Val Thr Asn Gly Leu Gly
        35                  40                  45

Thr Tyr Tyr Val Leu Asp Arg Val Tyr Leu Asn Thr Thr Leu Phe Leu
    50                  55                  60

Asn Gly Tyr Tyr Pro Thr Ser Gly Ser Thr Tyr Arg Asn Met Ala Leu
65                  70                  75                  80

Lys Gly Ser Val Leu Leu Ser Arg Leu Trp Phe Lys Pro Pro Phe Leu
                85                  90                  95

Ser Asp Phe Ile Asn Gly Ile Phe Ala Lys Val Lys Asn Thr Lys Val
            100                 105                 110
```

```
Ile Lys Asp Arg Val Met Tyr Ser Glu Phe Pro Ala Ile Thr Ile Gly
            115                 120                 125

Ser Thr Phe Val Asn Thr Ser Tyr Ser Val Val Gln Pro Arg Thr
        130                 135                 140

Ile Asn Ser Thr Gln Asp Gly Asn Lys Leu Gln Gly Leu Leu Glu
145                 150                 155                 160

Val Ser Val Cys Gln Tyr Asn Met Cys Glu Tyr Pro Gln Thr Ile Cys
                165                 170                 175

His Pro Asn Leu Gly Asn His Arg Lys Glu Leu Trp His Leu Asp Thr
                180                 185                 190

Gly Val Val Ser Cys Leu Tyr Lys Arg Asn Phe Thr Tyr Asp Val Asn
            195                 200                 205

Ala Asp Tyr Leu Tyr Phe His Phe Tyr Gln Glu Gly Thr Phe Tyr
        210                 215                 220

Ala Tyr Phe Thr Asp Thr Gly Val Val Thr Lys Phe Leu Phe Asn Val
225                 230                 235                 240

Tyr Leu Gly Met Ala Leu Ser His Tyr Val Met Pro Leu Thr Cys
                245                 250                 255

Asn Ser Lys Leu Thr Leu Glu Tyr Trp Val Thr Pro Leu Thr Ser Arg
                260                 265                 270

Gln Tyr Leu Leu Ala Phe Asn Gln Asp Gly Ile Ile Phe Asn Ala Glu
        275                 280                 285

Asp Cys Met Ser Asp Phe Met Ser Glu Ile Lys Cys Lys Thr Gln Ser
        290                 295                 300

Ile Ala Pro Pro Thr Gly Val Tyr Glu Leu Asn Gly Tyr Thr Val Gln
305                 310                 315                 320

Pro Ile Ala Asp Val Tyr Arg Arg Lys Pro Asn Leu Pro Asn Cys Asn
                325                 330                 335

Ile Glu Ala Trp Leu Asn Asp Lys Ser Val Pro Ser Pro Leu Asn Trp
                340                 345                 350

Glu Arg Lys Thr Phe Ser Asn Cys Asn Phe Asn Met Ser Ser Leu Met
        355                 360                 365

Ser Phe Ile Gln Ala Asp Ser Phe Thr Cys Asn Asn Ile Asp Ala Ala
370                 375                 380

Lys Ile Tyr Gly Met Cys Phe Ser Ser Ile Thr Ile Asp Lys Phe Ala
385                 390                 395                 400

Ile Pro Asn Gly Arg Lys Val Asp Leu Gln Leu Gly Asn Leu Gly Tyr
                405                 410                 415

Leu Gln Ser Phe Asn Tyr Arg Ile Asp Thr Thr Ala Thr Ser Cys Gln
                420                 425                 430

Leu Tyr Tyr Asn Leu Pro Ala Ala Asn Val Ser Val Ser Arg Phe Asn
        435                 440                 445

Pro Ser Thr Trp Asn Lys Arg Phe Gly Phe Ile Glu Asp Ser Val Phe
        450                 455                 460

Lys Pro Arg Pro Ala Gly Val Leu Thr Asn His Asp Val Val Tyr Ala
465                 470                 475                 480

Gln His Cys Phe Lys Ala Pro Lys Asn Phe Cys Pro Cys Lys Leu Asn
                485                 490                 495

Gly Ser Cys Val Gly Ser Gly Pro Gly Lys Asn Asn Gly Ile Gly Thr
                500                 505                 510

Cys Pro Ala Gly Thr Asn Tyr Leu Thr Cys Asp Asn Leu Cys Thr Pro
                515                 520                 525

Asp Pro Ile Thr Phe Thr Gly Thr Tyr Lys Cys Pro Gln Thr Lys Ser
```

```
                    530                 535                 540
Leu Val Gly Ile Gly Glu His Cys Ser Gly Leu Ala Val Lys Ser Asp
545                 550                 555                 560

Tyr Cys Gly Asn Ser Cys Thr Cys Arg Pro Gln Ala Phe Leu Gly
                565                 570                 575

Trp Ser Ala Asp Ser Cys Leu Gln Asp Lys Cys Asn Ile Phe Ala
                580                 585                 590

Asn Phe Ile Leu His Asp Val Asn Ser Gly Leu Thr Cys Ser Thr Asp
                595                 600                 605

Leu Gln Lys Ala Asn Thr Asp Ile Ile Leu Gly Val Cys Val Asn Tyr
610                 615                 620

Asp Leu Tyr Gly Ile Leu Gly Gln Gly Ile Phe Val Glu Val Asn Ala
625                 630                 635                 640

Thr Tyr Tyr Asn Ser Trp Gln Asn Leu Leu Tyr Asp Ser Asn Gly Asn
                645                 650                 655

Leu Tyr Gly Phe Arg Asp Tyr Ile Ile Asn Arg Thr Phe Met Ile Arg
                660                 665                 670

Ser Cys Tyr Ser Gly Arg Val Ser Ala Ala Phe His Ala Asn Ser Ser
                675                 680                 685

Glu Pro Ala Leu Leu Phe Arg Asn Ile Lys Cys Asn Tyr Val Phe Asn
690                 695                 700

Asn Ser Leu Thr Arg Gln Leu Gln Pro Ile Asn Tyr Phe Asp Ser Tyr
705                 710                 715                 720

Leu Gly Cys Val Val Asn Ala Tyr Asn Ser Thr Ala Ile Ser Val Gln
                725                 730                 735

Thr Cys Asp Leu Thr Val Gly Ser Gly Tyr Cys Val Asp Tyr Ser Lys
                740                 745                 750

Asn Arg Arg Ser Arg Gly Ala Ile Thr Thr Gly Tyr Arg Phe Thr Asn
                755                 760                 765

Phe Glu Pro Phe Thr Val Asn Ser Val Asn Asp Ser Leu Glu Pro Val
770                 775                 780

Gly Gly Leu Tyr Glu Ile Gln Ile Pro Ser Glu Phe Thr Ile Gly Asn
785                 790                 795                 800

Met Val Glu Phe Ile Gln Thr Ser Ser Pro Lys Val Thr Ile Asp Cys
                805                 810                 815

Ala Ala Phe Val Cys Gly Asp Tyr Ala Ala Cys Lys Ser Gln Leu Val
                820                 825                 830

Glu Tyr Gly Ser Phe Cys Asp Asn Ile Asn Ala Ile Leu Thr Glu Val
                835                 840                 845

Asn Glu Leu Leu Asp Thr Thr Gln Leu Gln Val Ala Asn Ser Leu Met
850                 855                 860

Asn Gly Val Thr Leu Ser Thr Lys Leu Lys Asp Gly Val Asn Phe Asn
865                 870                 875                 880

Val Asp Asp Ile Asn Phe Ser Pro Val Leu Gly Cys Leu Gly Ser Glu
                885                 890                 895

Cys Ser Lys Ala Ser Ser Arg Ser Ala Ile Glu Asp Leu Leu Phe Asp
                900                 905                 910

Lys Val Lys Leu Ser Asp Val Gly Phe Val Glu Ala Tyr Asn Asn Cys
                915                 920                 925

Thr Gly Gly Ala Glu Ile Arg Asp Leu Ile Cys Val Gln Ser Tyr Lys
930                 935                 940

Gly Ile Lys Val Leu Pro Pro Leu Leu Ser Glu Asn Gln Ile Ser Gly
945                 950                 955                 960
```

```
Tyr Thr Leu Ala Ala Thr Ser Ala Ser Leu Phe Pro Pro Trp Thr Ala
            965                 970                 975
Ala Ala Gly Val Pro Phe Tyr Leu Asn Val Gln Tyr Arg Ile Asn Gly
            980                 985                 990
Leu Gly Val Thr Met Asp Val Leu Ser Gln Asn Gln Lys Leu Ile Ala
            995                 1000                1005
Asn Ala Phe Asn Asn Ala Leu Tyr Ala Ile Gln Glu Gly Phe Asp
        1010                1015            1020
Ala Thr Asn Ser Ala Leu Val Lys Ile Gln Ala Val Val Asn Ala
        1025                1030            1035
Asn Ala Glu Ala Leu Asn Asn Leu Leu Gln Gln Leu Ser Asn Arg
        1040                1045            1050
Phe Gly Ala Ile Ser Ala Ser Leu Gln Glu Ile Leu Ser Arg Leu
        1055                1060            1065
Asp Ala Leu Glu Ala Glu Ala Gln Ile Asp Arg Leu Ile Asn Gly
        1070                1075            1080
Arg Leu Thr Ala Leu Asn Ala Tyr Val Ser Gln Gln Leu Ser Asp
        1085                1090            1095
Ser Thr Leu Val Lys Phe Ser Ala Ala Gln Ala Met Glu Lys Val
        1100                1105            1110
Asn Glu Cys Val Lys Ser Gln Ser Ser Arg Ile Asn Phe Cys Gly
        1115                1120            1125
Asn Gly Asn His Ile Ile Ser Leu Val Gln Asn Ala Pro Tyr Gly
        1130                1135            1140
Leu Tyr Phe Ile His Phe Ser Tyr Val Pro Thr Lys Tyr Val Thr
        1145                1150            1155
Ala Arg Val Ser Pro Gly Leu Cys Ile Ala Gly Asp Arg Gly Ile
        1160                1165            1170
Ala Pro Lys Ser Gly Tyr Phe Val Asn Val Asn Asn Thr Trp Met
        1175                1180            1185
Tyr Thr Gly Ser Gly Tyr Tyr Tyr Pro Glu Pro Ile Thr Glu Asn
        1190                1195            1200
Asn Val Val Val Met Ser Thr Cys Ala Val Asn Tyr Thr Lys Ala
        1205                1210            1215
Pro Tyr Val Met Leu Asn Thr Ser Ile Pro Asn Leu Pro Asp Phe
        1220                1225            1230
Lys Glu Glu Leu Asp Gln Trp Phe Lys Asn Gln Thr Ser Val Ala
        1235                1240            1245
Pro Asp Leu Ser Leu Asp Tyr Ile Asn Val Thr Phe Leu Asp Leu
        1250                1255            1260
Gln Val Glu Met Asn Arg Leu Gln Glu Ala Ile Lys Val Leu Asn
        1265                1270            1275
Gln Ser Tyr Ile Asn Leu Lys Asp Ile Gly Thr Tyr Glu Tyr Tyr
        1280                1285            1290
Val Lys Trp Pro Trp Tyr Val Trp Leu Leu Ile Cys Leu Ala Gly
        1295                1300            1305
Val Ala Met Leu Val Leu Leu Phe Phe Ile Cys Cys Thr Gly
        1310                1315            1320
Cys Gly Thr Ser Cys Phe Lys Lys Cys Gly Gly Cys Cys Asp Asp
        1325                1330            1335
Tyr Thr Gly Tyr Gln Glu Leu Val Ile Lys Thr Ser His Asp Asp
        1340                1345            1350
```

<210> SEQ ID NO 7
<211> LENGTH: 1173
<212> TYPE: PRT
<213> ORGANISM: 229E virus

<400> SEQUENCE: 7

```
Met Phe Val Leu Leu Val Ala Tyr Ala Leu Leu His Ile Ala Gly Cys
1               5                   10                  15

Gln Thr Thr Asn Gly Leu Asn Thr Ser Tyr Ser Val Cys Asn Gly Cys
            20                  25                  30

Val Gly Tyr Ser Glu Asn Val Phe Ala Val Glu Ser Gly Gly Tyr Ile
        35                  40                  45

Pro Ser Asp Phe Ala Phe Asn Asn Trp Phe Leu Leu Thr Asn Thr Ser
    50                  55                  60

Ser Val Val Asp Gly Val Val Arg Ser Phe Gln Pro Leu Leu Leu Asn
65                  70                  75                  80

Cys Leu Trp Ser Val Ser Gly Leu Arg Phe Thr Thr Gly Phe Val Tyr
                85                  90                  95

Phe Asn Gly Thr Gly Arg Gly Asp Cys Lys Gly Phe Ser Ser Asp Val
            100                 105                 110

Leu Ser Asp Val Ile Arg Tyr Asn Leu Asn Phe Glu Glu Asn Leu Arg
        115                 120                 125

Arg Gly Thr Ile Leu Phe Lys Thr Ser Tyr Gly Val Val Val Phe Tyr
    130                 135                 140

Cys Thr Asn Asn Thr Leu Val Ser Gly Asp Ala His Ile Pro Phe Gly
145                 150                 155                 160

Thr Val Leu Gly Asn Phe Tyr Cys Phe Val Asn Thr Thr Ile Gly Asn
                165                 170                 175

Glu Thr Thr Ser Ala Phe Val Gly Ala Leu Pro Lys Thr Val Arg Glu
            180                 185                 190

Phe Val Ile Ser Arg Thr Gly His Phe Tyr Ile Asn Gly Tyr Arg Tyr
        195                 200                 205

Phe Thr Leu Gly Asn Val Glu Ala Val Asn Phe Asn Val Thr Thr Ala
    210                 215                 220

Glu Thr Thr Asp Phe Cys Thr Val Ala Leu Ala Ser Tyr Ala Asp Val
225                 230                 235                 240

Leu Val Asn Val Ser Gln Thr Ser Ile Ala Asn Ile Ile Tyr Cys Asn
                245                 250                 255

Ser Val Ile Asn Arg Leu Arg Cys Asp Gln Leu Ser Phe Asp Val Pro
            260                 265                 270

Asp Gly Phe Tyr Ser Thr Ser Pro Ile Gln Ser Val Glu Leu Pro Val
        275                 280                 285

Ser Ile Val Ser Leu Pro Val Tyr His Lys His Thr Phe Ile Val Leu
    290                 295                 300

Tyr Val Asp Phe Lys Pro Gln Ser Gly Gly Gly Lys Cys Phe Asn Cys
305                 310                 315                 320

Tyr Pro Ala Gly Val Asn Ile Thr Leu Ala Asn Phe Asn Glu Thr Lys
                325                 330                 335

Gly Pro Leu Cys Val Asp Thr Ser His Phe Thr Thr Lys Tyr Val Ala
            340                 345                 350

Val Tyr Ala Asn Val Gly Arg Trp Ser Ala Ser Ile Asn Thr Gly Asn
        355                 360                 365

Cys Pro Phe Ser Phe Gly Lys Val Asn Asn Phe Val Lys Phe Gly Ser
    370                 375                 380
```

```
Val Cys Phe Ser Leu Lys Asp Ile Pro Gly Gly Cys Ala Met Pro Ile
385                 390                 395                 400

Val Ala Asn Trp Ala Tyr Ser Lys Tyr Tyr Thr Ile Gly Ser Leu Tyr
                405                 410                 415

Val Ser Trp Ser Asp Gly Asp Gly Ile Thr Gly Val Pro Gln Pro Val
            420                 425                 430

Glu Gly Val Ser Ser Phe Met Asn Val Thr Leu Asp Lys Cys Thr Lys
        435                 440                 445

Tyr Asn Ile Tyr Asp Val Ser Gly Val Gly Val Ile Arg Val Ser Asn
    450                 455                 460

Asp Thr Phe Leu Asn Gly Ile Thr Tyr Thr Ser Thr Gly Asn Leu
465                 470                 475                 480

Leu Gly Phe Lys Asp Val Thr Lys Gly Thr Ile Tyr Ser Ile Thr Pro
                485                 490                 495

Cys Asn Pro Pro Asp Gln Leu Val Val Tyr Gln Gln Ala Val Val Gly
            500                 505                 510

Ala Met Leu Ser Glu Asn Phe Thr Ser Tyr Gly Phe Ser Asn Val Val
        515                 520                 525

Glu Leu Pro Lys Phe Phe Tyr Ala Ser Asn Gly Thr Tyr Asn Cys Thr
530                 535                 540

Asp Ala Val Leu Thr Tyr Ser Ser Phe Gly Val Cys Ala Asp Gly Ser
545                 550                 555                 560

Ile Ile Ala Val Gln Pro Arg Asn Val Ser Tyr Asp Ser Val Ser Ala
                565                 570                 575

Ile Val Thr Ala Asn Leu Ser Ile Pro Ser Asn Trp Thr Thr Ser Val
            580                 585                 590

Gln Val Glu Tyr Leu Gln Ile Thr Ser Thr Pro Ile Val Val Asp Cys
        595                 600                 605

Ser Thr Tyr Val Cys Asn Gly Asn Val Arg Cys Val Glu Leu Leu Lys
    610                 615                 620

Gln Tyr Thr Ser Ala Cys Lys Thr Ile Glu Asp Ala Leu Arg Asn Ser
625                 630                 635                 640

Ala Arg Leu Glu Ser Ala Asp Val Ser Glu Met Leu Thr Phe Asp Lys
                645                 650                 655

Lys Ala Phe Thr Leu Ala Asn Val Ser Ser Phe Gly Asp Tyr Asn Leu
            660                 665                 670

Ser Ser Val Ile Pro Ser Leu Pro Thr Ser Gly Ser Arg Val Ala Gly
        675                 680                 685

Arg Ser Ala Ile Glu Asp Ile Leu Phe Ser Lys Leu Val Thr Ser Gly
    690                 695                 700

Leu Gly Thr Val Asp Ala Asp Tyr Lys Lys Cys Thr Lys Gly Leu Ser
705                 710                 715                 720

Ile Ala Asp Leu Ala Cys Ala Gln Tyr Tyr Asn Gly Ile Met Val Leu
                725                 730                 735

Pro Gly Val Ala Asp Ala Glu Arg Met Ala Met Tyr Thr Gly Ser Leu
            740                 745                 750

Ile Gly Gly Ile Ala Leu Gly Gly Leu Thr Ser Ala Val Ser Ile Pro
        755                 760                 765

Phe Ser Leu Ala Ile Gln Ala Arg Leu Asn Tyr Val Ala Leu Gln Thr
    770                 775                 780

Asp Val Leu Gln Glu Asn Gln Lys Ile Leu Ala Ala Ser Phe Asn Lys
785                 790                 795                 800
```

```
Ala Met Thr Asn Ile Val Asp Ala Phe Thr Gly Val Asn Asp Ala Ile
                805                 810                 815

Thr Gln Thr Ser Gln Ala Leu Gln Thr Val Ala Thr Ala Leu Asn Lys
        820                 825                 830

Ile Gln Asp Val Val Asn Gln Gln Gly Asn Ser Leu Asn His Leu Thr
            835                 840                 845

Ser Gln Leu Arg Gln Asn Phe Gln Ala Ile Ser Ser Ser Ile Gln Ala
850                 855                 860

Ile Tyr Asp Arg Leu Asp Thr Ile Gln Ala Asp Gln Gln Val Asp Arg
865                 870                 875                 880

Leu Ile Thr Gly Arg Leu Ala Ala Leu Asn Val Phe Val Ser His Thr
                885                 890                 895

Leu Thr Lys Tyr Thr Glu Val Arg Ala Ser Arg Gln Leu Ala Gln Gln
                900                 905                 910

Lys Val Asn Glu Cys Val Lys Ser Gln Ser Lys Arg Tyr Gly Phe Cys
            915                 920                 925

Gly Asn Gly Thr His Ile Phe Ser Ile Val Asn Ala Ala Pro Glu Gly
        930                 935                 940

Leu Val Phe Leu His Thr Val Leu Leu Pro Thr Gln Tyr Lys Asp Val
945                 950                 955                 960

Glu Ala Trp Ser Gly Leu Cys Val Asp Gly Thr Asn Gly Tyr Val Leu
                965                 970                 975

Arg Gln Pro Asn Leu Ala Leu Tyr Lys Glu Gly Asn Tyr Tyr Arg Ile
                980                 985                 990

Thr Ser Arg Ile Met Phe Glu Pro Arg Ile Pro Thr Met Ala Asp Phe
            995                 1000                1005

Val Gln Ile Glu Asn Cys Asn Val Thr Phe Val Asn Ile Ser Arg
        1010                1015                1020

Ser Glu Leu Gln Thr Ile Val Pro Glu Tyr Ile Asp Val Asn Lys
        1025                1030                1035

Thr Leu Gln Glu Leu Ser Tyr Lys Leu Pro Asn Tyr Thr Val Pro
        1040                1045                1050

Asp Leu Val Val Glu Gln Tyr Asn Gln Thr Ile Leu Asn Leu Thr
        1055                1060                1065

Ser Glu Ile Ser Thr Leu Glu Asn Lys Ser Ala Glu Leu Asn Tyr
        1070                1075                1080

Thr Val Gln Lys Leu Gln Thr Leu Ile Asp Asn Ile Asn Ser Thr
        1085                1090                1095

Leu Val Asp Leu Lys Trp Leu Asn Arg Val Glu Thr Tyr Ile Lys
        1100                1105                1110

Trp Pro Trp Trp Val Trp Leu Cys Ile Ser Val Val Leu Ile Phe
        1115                1120                1125

Val Val Ser Met Leu Leu Leu Cys Cys Cys Ser Thr Gly Cys Cys
        1130                1135                1140

Gly Phe Phe Ser Cys Phe Ala Ser Ser Ile Arg Gly Cys Cys Glu
        1145                1150                1155

Ser Thr Lys Leu Pro Tyr Tyr Asp Val Glu Lys Ile His Ile Gln
        1160                1165                1170

<210> SEQ ID NO 8
<211> LENGTH: 419
<212> TYPE: PRT
<213> ORGANISM: SARSCoV2 virus

<400> SEQUENCE: 8
```

```
Met Ser Asp Asn Gly Pro Gln Asn Gln Arg Asn Ala Pro Arg Ile Thr
1               5                   10                  15

Phe Gly Gly Pro Ser Asp Ser Thr Gly Ser Asn Gln Asn Gly Glu Arg
            20                  25                  30

Ser Gly Ala Arg Ser Lys Gln Arg Pro Gln Gly Leu Pro Asn Asn
        35                  40                  45

Thr Ala Ser Trp Phe Thr Ala Leu Thr Gln His Gly Lys Glu Asp Leu
    50                  55                  60

Lys Phe Pro Arg Gly Gln Gly Val Pro Ile Asn Thr Asn Ser Ser Pro
65                  70                  75                  80

Asp Asp Gln Ile Gly Tyr Tyr Arg Arg Ala Thr Arg Arg Ile Arg Gly
                85                  90                  95

Gly Asp Gly Lys Met Lys Asp Leu Ser Pro Arg Trp Tyr Phe Tyr Tyr
            100                 105                 110

Leu Gly Thr Gly Pro Glu Ala Gly Leu Pro Tyr Gly Ala Asn Lys Asp
        115                 120                 125

Gly Ile Ile Trp Val Ala Thr Glu Gly Ala Leu Asn Thr Pro Lys Asp
    130                 135                 140

His Ile Gly Thr Arg Asn Pro Ala Asn Asn Ala Ala Ile Val Leu Gln
145                 150                 155                 160

Leu Pro Gln Gly Thr Thr Leu Pro Lys Gly Phe Tyr Ala Glu Gly Ser
                165                 170                 175

Arg Gly Gly Ser Gln Ala Ser Ser Arg Ser Ser Ser Arg Ser Arg Asn
            180                 185                 190

Ser Ser Arg Asn Ser Thr Pro Gly Ser Ser Arg Gly Thr Ser Pro Ala
        195                 200                 205

Arg Met Ala Gly Asn Gly Gly Asp Ala Ala Leu Ala Leu Leu Leu Leu
210                 215                 220

Asp Arg Leu Asn Gln Leu Glu Ser Lys Met Ser Gly Lys Gly Gln Gln
225                 230                 235                 240

Gln Gln Gly Gln Thr Val Thr Lys Lys Ser Ala Ala Glu Ala Ser Lys
                245                 250                 255

Lys Pro Arg Gln Lys Arg Thr Ala Thr Lys Ala Tyr Asn Val Thr Gln
            260                 265                 270

Ala Phe Gly Arg Arg Gly Pro Glu Gln Thr Gln Gly Asn Phe Gly Asp
        275                 280                 285

Gln Glu Leu Ile Arg Gln Gly Thr Asp Tyr Lys His Trp Pro Gln Ile
    290                 295                 300

Ala Gln Phe Ala Pro Ser Ala Ser Ala Phe Phe Gly Met Ser Arg Ile
305                 310                 315                 320

Gly Met Glu Val Thr Pro Ser Gly Thr Trp Leu Thr Tyr Thr Gly Ala
                325                 330                 335

Ile Lys Leu Asp Asp Lys Asp Pro Asn Phe Lys Asp Gln Val Ile Leu
            340                 345                 350

Leu Asn Lys His Ile Asp Ala Tyr Lys Thr Phe Pro Pro Thr Glu Pro
        355                 360                 365

Lys Lys Asp Lys Lys Lys Ala Asp Glu Thr Gln Ala Leu Pro Gln
    370                 375                 380

Arg Gln Lys Lys Gln Gln Thr Val Thr Leu Leu Pro Ala Ala Asp Leu
385                 390                 395                 400

Asp Asp Phe Ser Lys Gln Leu Gln Gln Ser Met Ser Ser Ala Asp Ser
                405                 410                 415
```

Thr Gln Ala

<210> SEQ ID NO 9
<211> LENGTH: 422
<212> TYPE: PRT
<213> ORGANISM: SARSCoV virus

<400> SEQUENCE: 9

Met Ser Asp Asn Gly Pro Gln Ser Asn Gln Arg Ser Ala Pro Arg Ile
1               5                   10                  15

Thr Phe Gly Gly Pro Thr Asp Ser Thr Asp Asn Asn Gln Asn Gly Gly
            20                  25                  30

Arg Asn Gly Ala Arg Pro Lys Gln Arg Arg Pro Gln Gly Leu Pro Asn
        35                  40                  45

Asn Thr Ala Ser Trp Phe Thr Ala Leu Thr Gln His Gly Lys Glu Glu
50                  55                  60

Leu Arg Phe Pro Arg Gly Gln Gly Val Pro Ile Asn Thr Asn Ser Gly
65                  70                  75                  80

Pro Asp Asp Gln Ile Gly Tyr Tyr Arg Arg Ala Thr Arg Arg Val Arg
                85                  90                  95

Gly Gly Asp Gly Lys Met Lys Glu Leu Ser Pro Arg Trp Tyr Phe Tyr
            100                 105                 110

Tyr Leu Gly Thr Gly Pro Glu Ala Ser Leu Pro Tyr Gly Ala Asn Lys
        115                 120                 125

Glu Gly Ile Val Trp Val Ala Thr Glu Gly Ala Leu Asn Thr Pro Lys
130                 135                 140

Asp His Ile Gly Thr Arg Asn Pro Asn Asn Asn Ala Ala Thr Val Leu
145                 150                 155                 160

Gln Leu Pro Gln Gly Thr Thr Leu Pro Lys Gly Phe Tyr Ala Glu Gly
                165                 170                 175

Ser Arg Gly Gly Ser Gln Ala Ser Ser Arg Ser Ser Ser Arg Ser Arg
            180                 185                 190

Gly Asn Ser Arg Asn Ser Thr Pro Gly Ser Ser Arg Gly Asn Ser Pro
        195                 200                 205

Ala Arg Met Ala Ser Gly Gly Glu Thr Ala Leu Ala Leu Leu Leu
210                 215                 220

Leu Asp Arg Leu Asn Gln Leu Glu Ser Lys Val Ser Gly Lys Gly Gln
225                 230                 235                 240

Gln Gln Gln Gly Gln Thr Val Thr Lys Lys Ser Ala Ala Glu Ala Ser
                245                 250                 255

Lys Lys Pro Arg Gln Lys Arg Thr Ala Thr Lys Gln Tyr Asn Val Thr
            260                 265                 270

Gln Ala Phe Gly Arg Arg Gly Pro Glu Gln Thr Gln Gly Asn Phe Gly
        275                 280                 285

Asp Gln Asp Leu Ile Arg Gln Gly Thr Asp Tyr Lys His Trp Pro Gln
290                 295                 300

Ile Ala Gln Phe Ala Pro Ser Ala Ser Ala Phe Phe Gly Met Ser Arg
305                 310                 315                 320

Ile Gly Met Glu Val Thr Pro Ser Gly Thr Trp Leu Thr Tyr His Gly
                325                 330                 335

Ala Ile Lys Leu Asp Asp Lys Asp Pro Gln Phe Lys Asp Asn Val Ile
            340                 345                 350

Leu Leu Asn Lys His Ile Asp Ala Tyr Lys Thr Phe Pro Pro Thr Glu
        355                 360                 365

```
Pro Lys Lys Asp Lys Lys Lys Thr Asp Glu Ala Gln Pro Leu Pro
    370             375             380

Gln Arg Gln Lys Lys Gln Pro Thr Val Thr Leu Leu Pro Ala Ala Asp
385             390             395             400

Met Asp Asp Phe Ser Arg Gln Leu Gln Asn Ser Met Ser Gly Ala Ser
                405             410             415

Ala Asp Ser Thr Gln Ala
            420

<210> SEQ ID NO 10
<211> LENGTH: 413
<212> TYPE: PRT
<213> ORGANISM: MERS virus

<400> SEQUENCE: 10

Met Ala Ser Pro Ala Ala Pro Arg Ala Val Ser Phe Ala Asp Asn Asn
1               5                   10                  15

Asp Ile Thr Asn Thr Asn Leu Ser Arg Gly Arg Gly Arg Asn Pro Lys
            20                  25                  30

Pro Arg Ala Ala Pro Asn Asn Thr Val Ser Trp Tyr Thr Gly Leu Thr
        35                  40                  45

Gln His Gly Lys Val Pro Leu Thr Phe Pro Pro Gly Gln Gly Val Pro
    50                  55                  60

Leu Asn Ala Asn Ser Thr Pro Ala Gln Asn Ala Gly Tyr Trp Arg Arg
65                  70                  75                  80

Gln Asp Arg Lys Ile Asn Thr Gly Asn Gly Ile Lys Gln Leu Ala Pro
                85                  90                  95

Arg Trp Tyr Phe Tyr Tyr Thr Gly Thr Gly Pro Glu Ala Ala Leu Pro
            100                 105                 110

Phe Arg Ala Val Lys Asp Gly Ile Val Trp Val His Glu Asp Gly Ala
        115                 120                 125

Thr Asp Ala Pro Ser Thr Phe Gly Thr Arg Asn Pro Asn Asn Asp Ser
    130                 135                 140

Ala Ile Val Thr Gln Phe Ala Pro Gly Thr Lys Leu Pro Lys Asn Phe
145                 150                 155                 160

His Ile Glu Gly Thr Gly Gly Asn Ser Gln Ser Ser Ser Arg Ala Ser
                165                 170                 175

Ser Val Ser Arg Asn Ser Ser Arg Ser Ser Ser Gln Gly Ser Arg Ser
            180                 185                 190

Gly Asn Ser Thr Arg Gly Thr Ser Pro Gly Pro Ser Gly Ile Gly Ala
        195                 200                 205

Val Gly Gly Asp Leu Leu Tyr Leu Asp Leu Leu Asn Arg Leu Gln Ala
    210                 215                 220

Leu Glu Ser Gly Lys Val Lys Gln Ser Gln Pro Lys Val Ile Thr Lys
225                 230                 235                 240

Lys Asp Ala Ala Ala Lys Asn Lys Met Arg His Lys Arg Thr Ser
                245                 250                 255

Thr Lys Ser Phe Asn Met Val Gln Ala Phe Gly Leu Arg Gly Pro Gly
                260                 265                 270

Asp Leu Gln Gly Asn Phe Gly Asp Leu Gln Leu Asn Lys Leu Gly Thr
            275                 280                 285

Glu Asp Pro Arg Trp Pro Gln Ile Ala Glu Leu Ala Pro Thr Ala Ser
        290                 295                 300

Ala Phe Met Gly Met Ser Gln Phe Lys Leu Thr His Gln Asn Asn Asp
305                 310                 315                 320
```

```
Asp His Gly Asn Pro Val Tyr Phe Leu Arg Tyr Ser Gly Ala Ile Lys
            325                 330                 335

Leu Asp Pro Lys Asn Pro Asn Tyr Asn Lys Trp Leu Glu Leu Leu Glu
        340                 345                 350

Gln Asn Ile Asp Ala Tyr Lys Thr Phe Pro Lys Lys Glu Lys Lys Gln
        355                 360                 365

Lys Ala Pro Lys Glu Glu Ser Thr Asp Gln Met Ser Glu Pro Pro Lys
370                 375                 380

Glu Gln Arg Val Gln Gly Ser Ile Thr Gln Arg Thr Arg Thr Arg Pro
385                 390                 395                 400

Ser Val Gln Pro Gly Pro Met Ile Asp Val Asn Thr Asp
                405                 410

<210> SEQ ID NO 11
<211> LENGTH: 441
<212> TYPE: PRT
<213> ORGANISM: HKU1 virus

<400> SEQUENCE: 11

Met Ser Tyr Thr Pro Gly His Tyr Ala Gly Ser Arg Ser Ser Ser Gly
1               5                   10                  15

Asn Arg Ser Gly Ile Leu Lys Lys Thr Ser Trp Ala Asp Gln Ser Glu
            20                  25                  30

Arg Asn Tyr Gln Thr Phe Asn Arg Gly Arg Lys Thr Gln Pro Lys Phe
        35                  40                  45

Thr Val Ser Thr Gln Pro Gln Gly Asn Thr Ile Pro His Tyr Ser Trp
    50                  55                  60

Phe Ser Gly Ile Thr Gln Phe Gln Lys Gly Arg Asp Phe Lys Phe Ser
65                  70                  75                  80

Asp Gly Gln Gly Val Pro Ile Ala Phe Gly Val Pro Pro Ser Glu Ala
                85                  90                  95

Lys Gly Tyr Trp Tyr Arg His Ser Arg Arg Ser Phe Lys Thr Ala Asp
            100                 105                 110

Gly Gln Gln Lys Gln Leu Leu Pro Arg Trp Tyr Phe Tyr Tyr Leu Gly
        115                 120                 125

Thr Gly Pro Tyr Ala Asn Ala Ser Tyr Gly Glu Ser Leu Glu Gly Val
    130                 135                 140

Phe Trp Val Ala Asn His Gln Ala Asp Thr Ser Thr Pro Ser Asp Val
145                 150                 155                 160

Ser Ser Arg Asp Pro Thr Thr Gln Glu Ala Ile Pro Thr Arg Phe Pro
                165                 170                 175

Pro Gly Thr Ile Leu Pro Gln Gly Tyr Tyr Val Glu Gly Ser Gly Arg
            180                 185                 190

Ser Ala Ser Asn Ser Arg Pro Gly Ser Arg Ser Gln Ser Arg Gly Pro
        195                 200                 205

Asn Asn Arg Ser Leu Ser Arg Ser Asn Ser Asn Phe Arg His Ser Asp
    210                 215                 220

Ser Ile Val Lys Pro Asp Met Ala Asp Glu Ile Ala Asn Leu Val Leu
225                 230                 235                 240

Ala Lys Leu Gly Lys Asp Ser Lys Pro Gln Gln Val Thr Lys Gln Asn
                245                 250                 255

Ala Lys Glu Ile Arg His Lys Ile Leu Thr Lys Pro Arg Gln Lys Arg
            260                 265                 270

Thr Pro Asn Lys His Cys Asn Val Gln Gln Cys Phe Gly Lys Arg Gly
```

```
            275                 280                 285
Pro Ser Gln Asn Phe Gly Asn Ala Glu Met Leu Lys Leu Gly Thr Asn
290                 295                 300

Asp Pro Gln Phe Pro Ile Leu Ala Glu Leu Ala Pro Thr Pro Gly Ala
305                 310                 315                 320

Phe Phe Phe Gly Ser Lys Leu Asp Leu Val Lys Arg Asp Ser Glu Ala
                    325                 330                 335

Asp Ser Pro Val Lys Asp Val Phe Glu Leu His Tyr Ser Gly Ser Ile
                340                 345                 350

Arg Phe Asp Ser Thr Leu Pro Gly Phe Glu Thr Ile Met Lys Val Leu
            355                 360                 365

Glu Glu Asn Leu Asn Ala Tyr Val Asn Ser Asn Gln Asn Thr Asp Ser
370                 375                 380

Asp Ser Leu Ser Ser Lys Pro Gln Arg Lys Arg Gly Val Lys Gln Leu
385                 390                 395                 400

Pro Glu Gln Phe Asp Ser Leu Asn Leu Ser Ala Gly Thr Gln His Ile
                405                 410                 415

Ser Asn Asp Phe Thr Pro Glu Asp His Ser Leu Leu Ala Thr Leu Asp
                420                 425                 430

Asp Pro Tyr Val Glu Asp Ser Val Ala
            435                 440

<210> SEQ ID NO 12
<211> LENGTH: 377
<212> TYPE: PRT
<213> ORGANISM: NL63 virus

<400> SEQUENCE: 12

Met Ala Ser Val Asn Trp Ala Asp Asp Arg Ala Ala Arg Lys Lys Phe
1               5                   10                  15

Pro Pro Pro Ser Phe Tyr Met Pro Leu Leu Val Ser Ser Asp Lys Ala
                20                  25                  30

Pro Tyr Arg Val Ile Pro Arg Asn Leu Val Pro Ile Gly Lys Gly Asn
            35                  40                  45

Lys Asp Glu Gln Ile Gly Tyr Trp Asn Val Gln Glu Arg Trp Arg Met
50                  55                  60

Arg Arg Gly Gln Arg Val Asp Leu Pro Pro Lys Val His Phe Tyr Tyr
65                  70                  75                  80

Leu Gly Thr Gly Pro His Lys Asp Leu Lys Phe Arg Gln Arg Ser Asp
                85                  90                  95

Gly Val Val Trp Val Ala Lys Glu Gly Ala Lys Thr Val Asn Thr Ser
                100                 105                 110

Leu Gly Asn Arg Lys Arg Asn Gln Lys Pro Leu Glu Pro Lys Phe Ser
            115                 120                 125

Ile Ala Leu Pro Pro Glu Leu Ser Val Val Glu Phe Glu Asp Arg Ser
130                 135                 140

Asn Asn Ser Ser Arg Ala Ser Ser Arg Ser Thr Arg Asn Asn Ser
145                 150                 155                 160

Arg Asp Ser Ser Arg Ser Thr Ser Arg Gln Gln Ser Arg Thr Arg Ser
                165                 170                 175

Asp Ser Asn Gln Ser Ser Asp Leu Val Ala Val Thr Leu Ala
            180                 185                 190

Leu Lys Asn Leu Gly Phe Asp Asn Gln Ser Lys Ser Pro Ser Ser Ser
            195                 200                 205
```

```
Gly Thr Ser Thr Pro Lys Lys Pro Asn Lys Pro Leu Ser Gln Pro Arg
210                 215                 220

Ala Asp Lys Pro Ser Gln Leu Lys Lys Pro Arg Trp Lys Arg Val Pro
225                 230                 235                 240

Thr Arg Glu Glu Asn Val Ile Gln Cys Phe Gly Pro Arg Asp Phe Asn
                245                 250                 255

His Asn Met Gly Asp Ser Asp Leu Val Gln Asn Gly Val Asp Ala Lys
            260                 265                 270

Gly Phe Pro Gln Leu Ala Glu Leu Ile Pro Asn Gln Ala Ala Leu Phe
        275                 280                 285

Phe Asp Ser Glu Val Ser Thr Asp Glu Val Gly Asp Asn Val Gln Ile
    290                 295                 300

Thr Tyr Thr Tyr Lys Met Leu Val Ala Lys Asp Asn Lys Asn Leu Pro
305                 310                 315                 320

Lys Phe Ile Glu Gln Ile Ser Ala Phe Thr Lys Pro Ser Ser Ile Lys
                325                 330                 335

Glu Met Gln Ser Gln Ser Ser His Val Ala Gln Asn Thr Val Leu Asn
            340                 345                 350

Ala Ser Ile Pro Glu Ser Lys Pro Leu Ala Asp Asp Asp Ser Ala Ile
        355                 360                 365

Ile Glu Ile Val Asn Glu Val Leu His
370                 375

<210> SEQ ID NO 13
<211> LENGTH: 448
<212> TYPE: PRT
<213> ORGANISM: OC43 virus

<400> SEQUENCE: 13

Met Ser Phe Thr Pro Gly Lys Gln Ser Ser Arg Ala Ser Ser Gly
1               5                   10                  15

Asn Arg Ser Gly Asn Gly Ile Leu Lys Trp Ala Asp Gln Ser Asp Gln
                20                  25                  30

Val Arg Asn Val Gln Thr Arg Gly Arg Arg Ala Gln Pro Lys Gln Thr
            35                  40                  45

Ala Thr Ser Gln Gln Pro Ser Gly Gly Asn Val Val Pro Tyr Tyr Ser
        50                  55                  60

Trp Phe Ser Gly Ile Thr Gln Phe Gln Lys Gly Lys Glu Phe Glu Phe
65                  70                  75                  80

Val Glu Gly Gln Gly Pro Pro Ile Ala Pro Gly Val Pro Ala Thr Glu
                85                  90                  95

Ala Lys Gly Tyr Trp Tyr Arg His Asn Arg Gly Ser Phe Lys Thr Ala
            100                 105                 110

Asp Gly Asn Gln Arg Gln Leu Leu Pro Arg Trp Tyr Phe Tyr Tyr Leu
        115                 120                 125

Gly Thr Gly Pro His Ala Lys Asp Gln Tyr Gly Thr Asp Ile Asp Gly
    130                 135                 140

Val Tyr Trp Val Ala Ser Asn Gln Ala Asp Val Asn Thr Pro Ala Asp
145                 150                 155                 160

Ile Val Asp Arg Asp Pro Ser Ser Asp Glu Ala Ile Pro Thr Arg Phe
                165                 170                 175

Pro Pro Gly Thr Val Leu Pro Gln Gly Tyr Tyr Ile Glu Gly Ser Gly
            180                 185                 190

Arg Ser Ala Pro Asn Ser Arg Ser Thr Ser Arg Thr Ser Ser Arg Ala
        195                 200                 205
```

Ser Ser Ala Gly Ser Arg Ser Arg Ala Asn Ser Gly Asn Arg Thr Pro
            210                 215                 220

Thr Ser Gly Val Thr Pro Asp Met Ala Asp Gln Ile Ala Ser Leu Val
225                 230                 235                 240

Leu Ala Lys Leu Gly Lys Asp Ala Thr Lys Pro Gln Gln Val Thr Lys
            245                 250                 255

His Thr Ala Lys Glu Val Arg Gln Lys Ile Leu Asn Lys Pro Arg Gln
            260                 265                 270

Lys Arg Ser Pro Asn Lys Gln Cys Thr Val Gln Gln Cys Phe Gly Lys
            275                 280                 285

Arg Gly Pro Asn Gln Asn Phe Gly Gly Glu Met Leu Lys Leu Gly
290                 295                 300

Thr Ser Asp Pro Gln Phe Pro Ile Leu Ala Glu Leu Ala Pro Thr Ala
305                 310                 315                 320

Gly Ala Phe Phe Phe Gly Ser Arg Leu Glu Leu Ala Lys Val Gln Asn
            325                 330                 335

Leu Ser Gly Asn Pro Asp Glu Pro Gln Lys Asp Val Tyr Glu Leu Arg
            340                 345                 350

Tyr Asn Gly Ala Ile Arg Phe Asp Ser Thr Leu Ser Gly Phe Glu Thr
            355                 360                 365

Ile Met Lys Val Leu Asn Glu Asn Leu Asn Ala Tyr Gln Gln Gln Asp
370                 375                 380

Gly Met Met Asn Met Ser Pro Lys Pro Gln Arg Gln Arg Gly His Lys
385                 390                 395                 400

Asn Gly Gln Gly Glu Asn Asp Asn Ile Ser Val Ala Val Pro Lys Ser
            405                 410                 415

Arg Val Gln Gln Asn Lys Ser Arg Glu Leu Thr Ala Glu Asp Ile Ser
            420                 425                 430

Leu Leu Lys Lys Met Asp Glu Pro Tyr Thr Glu Asp Thr Ser Glu Ile
            435                 440                 445

<210> SEQ ID NO 14
<211> LENGTH: 389
<212> TYPE: PRT
<213> ORGANISM: 229E virus

<400> SEQUENCE: 14

Met Ala Thr Val Lys Trp Ala Asp Ala Ser Glu Pro Gln Arg Gly Arg
1               5                   10                  15

Gln Gly Arg Ile Pro Tyr Ser Leu Tyr Ser Pro Leu Leu Val Asp Ser
            20                  25                  30

Glu Gln Pro Trp Lys Val Ile Pro Arg Asn Leu Val Pro Ile Asn Lys
            35                  40                  45

Lys Asp Lys Asn Lys Leu Ile Gly Tyr Trp Asn Val Gln Lys Arg Phe
50                  55                  60

Arg Thr Arg Lys Gly Lys Arg Val Asp Leu Ser Pro Lys Leu His Phe
65                  70                  75                  80

Tyr Tyr Leu Gly Thr Gly Pro His Lys Asp Ala Lys Phe Arg Glu Arg
            85                  90                  95

Val Glu Gly Val Val Trp Val Ala Val Asp Gly Ala Lys Thr Glu Pro
            100                 105                 110

Thr Gly Tyr Gly Val Arg Arg Lys Asn Ser Glu Pro Glu Ile Pro His
            115                 120                 125

Phe Asn Gln Lys Leu Pro Asn Gly Val Thr Val Val Glu Glu Pro Asp

```
                130             135             140
Ser Arg Ala Pro Ser Arg Ser Gln Ser Arg Ser Gln Ser Arg Gly Arg
145                 150                 155                 160

Gly Glu Ser Lys Pro Gln Ser Arg Asn Pro Ser Ser Asp Arg Asn His
                165                 170                 175

Asn Ser Gln Asp Asp Ile Met Lys Ala Val Ala Ala Leu Lys Ser
            180                 185                 190

Leu Gly Phe Asp Lys Pro Gln Glu Lys Asp Lys Lys Ser Ala Lys Thr
            195                 200                 205

Gly Thr Pro Lys Pro Ser Arg Asn Gln Ser Pro Ala Ser Ser Gln Thr
210                 215                 220

Ser Ala Lys Ser Leu Ala Arg Ser Gln Ser Ser Glu Thr Lys Glu Gln
225                 230                 235                 240

Lys His Glu Met Gln Lys Pro Arg Trp Lys Arg Gln Pro Asn Asp Asp
                245                 250                 255

Val Thr Ser Asn Val Thr Gln Cys Phe Gly Pro Arg Asp Leu Asp His
            260                 265                 270

Asn Phe Gly Ser Ala Gly Val Val Ala Asn Gly Val Lys Ala Lys Gly
            275                 280                 285

Tyr Pro Gln Phe Ala Glu Leu Val Pro Ser Thr Ala Ala Met Leu Phe
            290                 295                 300

Asp Ser His Ile Val Ser Lys Glu Ser Gly Asn Thr Val Val Leu Thr
305                 310                 315                 320

Phe Thr Thr Arg Val Thr Val Pro Lys Asp His Pro His Leu Gly Lys
                325                 330                 335

Phe Leu Glu Glu Leu Asn Ala Phe Thr Arg Glu Met Gln Gln His Pro
            340                 345                 350

Leu Leu Asn Pro Ser Ala Leu Glu Phe Asn Pro Ser Gln Thr Ser Pro
            355                 360                 365

Ala Thr Ala Glu Pro Val Arg Asp Glu Val Ser Ile Glu Thr Asp Ile
            370                 375                 380

Ile Asp Glu Val Asn
385

<210> SEQ ID NO 15
<211> LENGTH: 805
<212> TYPE: PRT
<213> ORGANISM: Homo sapiens

<400> SEQUENCE: 15

Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
    50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110
```

-continued

```
Ser Lys Arg Leu Asn Thr Ile Leu Asn Thr Met Ser Thr Ile Tyr Ser
            115                 120                 125

Thr Gly Lys Val Cys Asn Pro Asp Asn Pro Gln Glu Cys Leu Leu Leu
        130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
        290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Lys Gly Asp Phe Arg Ile Leu Met Cys Thr Lys Val Thr Met Asp Asp
        355                 360                 365

Phe Leu Thr Ala His His Glu Met Gly His Ile Gln Tyr Asp Met Ala
370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
        435                 440                 445

Thr Leu Pro Phe Thr Tyr Met Leu Glu Lys Trp Arg Trp Met Val Phe
450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Phe Gln Phe Gln Glu Ala
        515                 520                 525

Leu Cys Gln Ala Ala Lys His Glu Gly Pro Leu His Lys Cys Asp Ile
```

```
                530             535             540
Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
                580                 585                 590

Thr Trp Leu Lys Asp Gln Asn Lys Asn Ser Phe Val Gly Trp Ser Thr
                595                 600                 605

Asp Trp Ser Pro Tyr Ala Asp Gln Ser Ile Lys Val Arg Ile Ser Leu
                610                 615                 620

Lys Ser Ala Leu Gly Asp Lys Ala Tyr Glu Trp Asn Asp Asn Glu Met
625                 630                 635                 640

Tyr Leu Phe Arg Ser Ser Val Ala Tyr Ala Met Arg Gln Tyr Phe Leu
                645                 650                 655

Lys Val Lys Asn Gln Met Ile Leu Phe Gly Glu Glu Asp Val Arg Val
                660                 665                 670

Ala Asn Leu Lys Pro Arg Ile Ser Phe Asn Phe Phe Val Thr Ala Pro
                675                 680                 685

Lys Asn Val Ser Asp Ile Ile Pro Arg Thr Glu Val Glu Lys Ala Ile
                690                 695                 700

Arg Met Ser Arg Ser Arg Ile Asn Asp Ala Phe Arg Leu Asn Asp Asn
705                 710                 715                 720

Ser Leu Glu Phe Leu Gly Ile Gln Pro Thr Leu Gly Pro Pro Asn Gln
                725                 730                 735

Pro Pro Val Ser Ile Trp Leu Ile Val Phe Gly Val Val Met Gly Val
                740                 745                 750

Ile Val Val Gly Ile Val Leu Ile Phe Thr Gly Ile Arg Asp Arg
                755                 760                 765

Lys Lys Lys Asn Lys Ala Arg Ser Gly Glu Asn Pro Tyr Ala Ser Ile
770                 775                 780

Asp Ile Ser Lys Gly Glu Asn Asn Pro Gly Phe Gln Asn Thr Asp Asp
785                 790                 795                 800

Val Gln Thr Ser Phe
                805

<210> SEQ ID NO 16
<211> LENGTH: 304
<212> TYPE: PRT
<213> ORGANISM: SARSCoV2 virus

<400> SEQUENCE: 16

Val Phe Asn Ala Thr Arg Phe Ala Ser Val Tyr Ala Trp Asn Arg Lys
1               5                   10                  15

Arg Ile Ser Asn Cys Val Ala Asp Tyr Ser Val Leu Tyr Asn Ser Ala
                20                  25                  30

Ser Phe Ser Thr Phe Lys Cys Tyr Gly Val Ser Pro Thr Lys Leu Asn
                35                  40                  45

Asp Leu Cys Phe Thr Asn Val Tyr Ala Asp Ser Phe Val Ile Arg Gly
                50                  55                  60

Asp Glu Val Arg Gln Ile Ala Pro Gly Gln Thr Gly Lys Ile Ala Asp
65                  70                  75                  80

Tyr Asn Tyr Lys Leu Pro Asp Asp Phe Thr Gly Cys Val Ile Ala Trp
                85                  90                  95
```

```
Asn Ser Asn Asn Leu Asp Ser Lys Val Gly Gly Asn Tyr Asn Tyr Leu
            100                 105                 110

Tyr Arg Leu Phe Arg Lys Ser Asn Leu Lys Pro Phe Glu Arg Asp Ile
        115                 120                 125

Ser Thr Glu Ile Tyr Gln Ala Gly Ser Thr Pro Cys Asn Gly Val Glu
    130                 135                 140

Gly Phe Asn Cys Tyr Phe Pro Leu Gln Ser Tyr Gly Phe Gln Pro Thr
145                 150                 155                 160

Asn Gly Val Gly Tyr Gln Pro Tyr Arg Val Val Val Leu Ser Phe Glu
                165                 170                 175

Leu Leu His Ala Pro Ala Thr Val Cys Gly Pro Lys Lys Ser Thr Asn
            180                 185                 190

Leu Val Lys Asn Lys Cys Val Asn Phe Asn Phe Asn Gly Leu Thr Gly
        195                 200                 205

Thr Gly Val Leu Thr Glu Ser Asn Lys Lys Phe Leu Pro Phe Gln Gln
    210                 215                 220

Phe Gly Arg Asp Ile Ala Asp Thr Thr Asp Ala Val Arg Asp Pro Gln
225                 230                 235                 240

Thr Leu Glu Ile Leu Asp Ile Thr Pro Cys Ser Phe Gly Gly Val Ser
                245                 250                 255

Val Ile Thr Pro Gly Thr Asn Thr Ser Asn Gln Val Ala Val Leu Tyr
            260                 265                 270

Gln Asp Val Asn Cys Thr Glu Val Pro Val Ala Ile His Ala Asp Gln
        275                 280                 285

Leu Thr Pro Thr Trp Arg Val Tyr Ser Thr Gly Ser Asn Val Phe Gln
    290                 295                 300

<210> SEQ ID NO 17
<211> LENGTH: 11
<212> TYPE: PRT
<213> ORGANISM: Artificial Sequence
<220> FEATURE:
<223> OTHER INFORMATION: linker

<400> SEQUENCE: 17

Gly Gly Ser Gly Gly Gly Ser Gly Gly Gly Ser
1               5                   10

<210> SEQ ID NO 18
<211> LENGTH: 6
<212> TYPE: PRT
<213> ORGANISM: Artificial Sequence
<220> FEATURE:
<223> OTHER INFORMATION: Histidine tag

<400> SEQUENCE: 18

His His His His His His
1               5

<210> SEQ ID NO 19
<211> LENGTH: 321
<212> TYPE: PRT
<213> ORGANISM: Artificial Sequence
<220> FEATURE:
<223> OTHER INFORMATION: SARSCoV2 S protein RBD with linker and
      histidine tag

<400> SEQUENCE: 19

Val Phe Asn Ala Thr Arg Phe Ala Ser Val Tyr Ala Trp Asn Arg Lys
1               5                   10                  15
```

-continued

```
Arg Ile Ser Asn Cys Val Ala Asp Tyr Ser Val Leu Tyr Asn Ser Ala
            20                  25                  30

Ser Phe Ser Thr Phe Lys Cys Tyr Gly Val Ser Pro Thr Lys Leu Asn
        35                  40                  45

Asp Leu Cys Phe Thr Asn Val Tyr Ala Asp Ser Phe Val Ile Arg Gly
    50                  55                  60

Asp Glu Val Arg Gln Ile Ala Pro Gly Gln Thr Gly Lys Ile Ala Asp
65                  70                  75                  80

Tyr Asn Tyr Lys Leu Pro Asp Asp Phe Thr Gly Cys Val Ile Ala Trp
                85                  90                  95

Asn Ser Asn Asn Leu Asp Ser Lys Val Gly Gly Asn Tyr Asn Tyr Leu
            100                 105                 110

Tyr Arg Leu Phe Arg Lys Ser Asn Leu Lys Pro Phe Glu Arg Asp Ile
        115                 120                 125

Ser Thr Glu Ile Tyr Gln Ala Gly Ser Thr Pro Cys Asn Gly Val Glu
    130                 135                 140

Gly Phe Asn Cys Tyr Phe Pro Leu Gln Ser Tyr Gly Phe Gln Pro Thr
145                 150                 155                 160

Asn Gly Val Gly Tyr Gln Pro Tyr Arg Val Val Val Leu Ser Phe Glu
                165                 170                 175

Leu Leu His Ala Pro Ala Thr Val Cys Gly Pro Lys Lys Ser Thr Asn
            180                 185                 190

Leu Val Lys Asn Lys Cys Val Asn Phe Asn Phe Asn Gly Leu Thr Gly
        195                 200                 205

Thr Gly Val Leu Thr Glu Ser Asn Lys Lys Phe Leu Pro Phe Gln Gln
    210                 215                 220

Phe Gly Arg Asp Ile Ala Asp Thr Thr Asp Ala Val Arg Asp Pro Gln
225                 230                 235                 240

Thr Leu Glu Ile Leu Asp Ile Thr Pro Cys Ser Phe Gly Gly Val Ser
                245                 250                 255

Val Ile Thr Pro Gly Thr Asn Thr Ser Asn Gln Val Ala Val Leu Tyr
            260                 265                 270

Gln Asp Val Asn Cys Thr Glu Val Pro Val Ala Ile His Ala Asp Gln
        275                 280                 285

Leu Thr Pro Thr Trp Arg Val Tyr Ser Thr Gly Ser Asn Val Phe Gln
    290                 295                 300

Gly Gly Ser Gly Gly Gly Ser Gly Gly Gly Ser His His His His His
305                 310                 315                 320

His
```

|---|---|

HYPERIMMUNIZED EGG PRODUCT FOR TREATMENT OR PREVENTION OF CORONAVIRUS INFECTION

RELATED APPLICATIONS

This application claims priority to U.S. Provisional Patent Application No. 63/160,155 filed on Mar. 12, 2021, the contents of each of which are incorporated herein in their entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 15809533_000003_US01_Sequence_Listing.txt. The size of the text file is 112 bytes, and the text file was created on Mar. 10, 2022.

BACKGROUND

Severe Acute Respiratory Syndrome coronavirus 2 (SARS-CoV-2) is the seventh member of the Coronaviridae family known to infect humans. Three of these viruses, SARS-CoV-1, MERS, and SARS-CoV-2, can cause severe disease. The remaining four, HCoV-HKU1, HCoV-NL63, HCoV-OC43 and HCoV-229E, are associated with mild respiratory symptoms. Genomic comparison of both alpha- and betacoronaviruses identifies two important features of the SARS-CoV-2 genome that distinguishes it from other members of the Coronaviridae family. First, based on structural modelling and early biochemical experiments, SARS-CoV-2 appears to be optimized for binding to the human angiotensin converting enzyme 2 (ACE2) receptor. Second, the highly variable spike (S) protein of SARS-CoV-2 has a polybasic (furin) cleavage site at the S1 and S2 boundary via the insertion of twelve nucleotides. Cleavage of coronavirus S proteins has been shown to enable cell entry. A need exists for improved methods of treating and preventing coronavirus infection in general, and SARS-CoV-2 infection in particular.

SUMMARY OF THE INVENTION

In certain aspects, the disclosure relates to a method for preventing or treating a coronavirus infection in a subject in need thereof, comprising administering to the subject a therapeutically effective amount of a hyperimmunized egg product obtained from an egg-producing animal, thereby preventing or treating coronavirus infection in the subject, wherein the hyperimmunized egg product comprises a therapeutically effective amount of one or more antibodies to the coronavirus. In certain embodiments, the coronavirus is a human coronavirus selected from the group consisting of Severe Acute Respiratory Syndrome coronavirus (SARS-CoV), Middle East Respiratory Syndrome coronavirus (MERS-CoV), Severe Acute Respiratory Syndrome coronavirus 2 (SARS-CoV-2), human coronavirus HKU1 (HCoV-HKU1), human coronavirus NL63 (HCoV-NL63), human coronavirus OC43 (HCoV-OC43) and human coronavirus 229E (HCoV-229E).

In certain embodiments, the subject is infected with Severe Acute Respiratory Syndrome coronavirus (SARS-CoV), Middle East Respiratory Syndrome coronavirus (MERS-CoV), Severe Acute Respiratory Syndrome coronavirus 2 (SARS-CoV-2), human coronavirus HKU1 (HCoV-HKU1), human coronavirus NL63 (HCoV-NL63), human coronavirus OC43 (HCoV-OC43) or human coronavirus 229E (HCoV-229E. In certain embodiments, the subject has Severe Acute Respiratory Syndrome (SARS), Middle East Respiratory Syndrome (MERS) or Coronavirus Disease-2019 (COVID-19). In certain embodiments, the coronavirus is SARS-CoV-2. In certain embodiments, the subject is infected with SARS-CoV-2. In certain embodiments, the subject has Coronavirus Disease-2019 (COVID-19).

In certain embodiments, the methods disclosed herein further comprise hyperimmunizing the egg-producing animal with a composition comprising an antigen selected from the group consisting of: i) a human coronavirus spike (S) protein, a human coronavirus S1 subunit protein, a human coronavirus S2 subunit protein, and an immunogenic fragment thereof; ii) a human coronavirus nucleocapsid (N) protein, and an immunogenic fragment thereof; iii) a human ACE2 receptor protein, and an immunogenic fragment thereof; and iv) a human coronavirus selected from the group consisting of SARS CoV-1, MERS, SARS-CoV-2, HCoV-HKU1, HCoV-NL63, HCoV-OC43 and HCoV-229E.

In certain embodiments, the composition further comprises an adjuvant. In certain embodiments, the adjuvant is selected from the group consisting of Freunds complete adjuvant, Freunds incomplete adjuvant and QS21. In certain embodiments, the composition is administered to the egg-producing animal by subcutaneous injection or intramuscular injection. In certain embodiments, the composition is administered to the egg-producing animal at least twice and at an interval from once every 2 weeks to once every 3 months. In certain embodiments, the one or more antibodies to the human coronavirus in the hyperimmunized egg product have a titer of at least 200,000 as measured by optical density. In certain embodiments, the titer of at least 200,000 is maintained in hyperimmunized egg products produced by the egg-producing animal for at least two weeks. In certain embodiments, the hyperimmunized egg product is administered to the subject as an oral rinse, by inhalation, by nasal drops, or by eye drops. In certain embodiments, the hyperimmunized egg product is a whole egg, an egg yolk, or purified or partially purified IgY. In certain embodiments, the hyperimmunized egg product is a liquid, a freeze-dried powder, or formulated to be administered as a spray. In certain embodiments, the hyperimmunized egg product is formulated to contain GRAS components and excipients to improve solubility, stability and dissolution.

In certain embodiments, the methods disclosed herein further comprise collecting a hyperimmunized egg from the egg-producing animal that has been hyperimmunized, and preparing a hyperimmunized egg product from the hyperimmunized egg. In certain embodiments, the hyperimmunized egg product comprises at least 20% more by weight of an IgY antibody specific to the coronavirus relative to a control egg product obtained from an egg-producing animal that is not hyperimmunized. In certain embodiments, the subject is a human. In certain embodiments, the coronavirus is a coronavirus that infects humans.

In certain aspects, the disclosure relates to a hyperimmunized egg produced by an animal that has been hyperimmunized with an antigen selected from the group consisting of: i) a human coronavirus spike (S) protein, a human coronavirus S1 subunit protein, a human coronavirus S2 subunit protein, and an immunogenic fragment thereof; ii) a human coronavirus nucleocapsid (N) protein, and an immunogenic fragment thereof; iii) a human angiotensin converting enzyme 2 (ACE2) receptor protein, and an immunogenic fragment thereof; and iv) a human coronavirus selected from the group consisting of SARS CoV-1, MERS, SARS-CoV-2, HCoV-HKU1, HCoV-NL63, HCoV-OC43 and HCoV-229E, wherein the level of antibodies to the antigen in the hyperimmunized egg is increased relative to an egg from an animal that has not been hyperimmunized. In certain embodiments, the antibodies in the hyperimmunized egg have a titer of at least one million as measured by optical density. In certain aspects, the disclosure relates to a hyperimmunized egg product obtained from a hyperimmunized egg described herein. In certain embodiments, the hyperimmunized egg product is whole egg, egg yolk, or purified or partially purified IgY antibody to the coronavirus.

In certain aspects, the disclosure relates to a pharmaceutical composition comprising a hyperimmunized egg product as disclosed herein and a pharmaceutically acceptable carrier. In certain embodiments, the pharmaceutical composition is formulated for oral, nasal or ocular administration. In certain embodiments, the pharmaceutical composition is formulated for administration to the subject as an oral rinse, by inhalation, by nasal drops or by eye drops. In certain embodiments, the pharmaceutical composition is a liquid, a freeze-dried powder, or formulated to be administered as a spray. In certain embodiments, the pharmaceutically acceptable carrier comprises a compound that is generally recognized as safe (GRAS) and an excipient that improves solubility, stability and/or dissolution. In certain embodiments, the hyperimmunized egg product is formulated in nanoparticles or in an emulsion.

In certain aspects, the disclosure relates to a method of preparing a hyperimmunized egg product comprising: a) hyperimmunizing an egg-producing animal with a composition comprising an antigen selected from the group consisting of: i) a human coronavirus spike (S) protein, a human coronavirus S1 subunit protein, a human coronavirus S2 subunit protein, and an immunogenic fragment thereof; ii) a human coronavirus nucleocapsid (N) protein, and an immunogenic fragment thereof; iii) a human Angiotensin converting enzyme 2 (ACE2) receptor protein, and an immunogenic fragment thereof; and iv) a human coronavirus selected from the group consisting of Severe Acute Respiratory Syndrome coronavirus (SARS-CoV), Middle East Respiratory Syndrome coronavirus (MERS-CoV), Severe Acute Respiratory Syndrome coronavirus 2 (SARS-CoV-2), human coronavirus HKU1 (HCoV-HKU1), human coronavirus NL63 (HCoV-NL63), human coronavirus OC43 (HCoV-OC43) and human coronavirus 229E (HCoV-229E); and b) preparing a hyperimmunized egg product from one or more eggs produced by the animal.

In certain embodiments, the composition further comprises an adjuvant. In certain embodiments, the adjuvant is selected from the group consisting of Freunds complete adjuvant, Freunds incomplete adjuvant and QS21. In certain embodiments, the composition is administered to the egg-producing animal by subcutaneous injection or intramuscular injection. In certain embodiments, the composition is administered to the egg-producing animal at least twice and at an interval from once every 2 weeks to once every 3 months. In certain embodiments, the egg-producing animal is a chicken. In certain embodiments, the human coronavirus is SARS-CoV-2.

Provided is a method for preventing or treating a coronavirus infection in a subject in need thereof, comprising administering to the subject a therapeutically effective amount of a hyperimmunized egg product obtained from an egg-producing animal, thereby preventing or treating coronavirus infection in the subject, wherein the hyperimmunized egg product comprises a therapeutically effective amount of one or more antibodies to the coronavirus. The coronavirus can be a human coronavirus selected from the group consisting of Severe Acute Respiratory Syndrome coronavirus (SARS-CoV), Middle East Respiratory Syndrome coronavirus (MERS-CoV), Severe Acute Respiratory Syndrome coronavirus 2 (SARS-CoV-2), human coronavirus HKU1 (HCoV-HKU1), human coronavirus NL63 (HCoV-NL63), human coronavirus OC43 (HCoV-OC43) and human coronavirus 229E (HCoV-229E).

The method can minimize risk of infection in a subject. The method can treat a subject that is infected with Severe Acute Respiratory Syndrome coronavirus (SARS-CoV), Middle East Respiratory Syndrome coronavirus (MERS-CoV), Severe Acute Respiratory Syndrome coronavirus 2 (SARS-CoV-2), human coronavirus HKU1 (HCoV-HKU1), human coronavirus NL63 (HCoV-NL63), human coronavirus OC43 (HCoV-OC43) or human coronavirus 229E (HCoV-229E. The method can treat a subject that has Severe Acute Respiratory Syndrome (SARS), Middle East Respiratory Syndrome (MERS) or Coronavirus Disease-2019 (COVID-19).

In some applications, the method can prevent or treat a subject where the coronavirus is SARS-CoV-2. The method can treat a subject infected with SARS-CoV-2. The method can treat a subject that has Coronavirus Disease-2019 (COVID-19).

The method can include hyperimmunizing the egg-producing animal with a composition comprising an antigen. The composition can include one or a combination of antigens. The antigen can be selected from the group consisting of: i) a human coronavirus spike (S) protein, a human coronavirus S1 subunit protein, a human coronavirus S2 subunit protein, a human coronavirus receptor binding domain (RBD), and an immunogenic fragment thereof; ii) a human coronavirus nucleocapsid (N) protein, and an immunogenic fragment thereof; iii) a human ACE2 receptor protein, and an immunogenic fragment thereof; iv) a human coronavirus selected from the group consisting of SARS CoV-1, MERS, SARS-CoV-2, HCoV-HKU1, HCoV-NL63, HCoV-OC43 and HCoV-229E; v) a human coronavirus S protein, or an immunogenic fragment thereof; vi) an S protein of SARS-CoV-2, or an immunogenic fragment thereof; vii) a receptor binding domain (RBD) of a human coronavirus S protein, or an immunogenic fragment thereof; viii) a receptor binding domain (RBD) of SARS-CoV-2, or an immunogenic fragment thereof; ix) the amino acid sequence of SEQ ID NO: 16, or an immunogenic fragment thereof; and x) the amino acid sequence of SEQ ID NO: 19, or an immunogenic fragment thereof;

In the methods provided herein, the composition for hyperimmunizing the egg-producing animal can include an adjuvant. In some methods, the adjuvant is selected from the group consisting of Freund's complete adjuvant, Freund's incomplete adjuvant and QS21. In some methods, the adjuvant is selected from the group consisting of Freund's complete adjuvant, Freund's incomplete adjuvant, a saponin, a biodegradable polymer, aluminum hydroxide, mineral oil, a surfactant, and combinations thereof. The composition can be administered to the egg-producing animal by subcutaneous injection or intramuscular injection. The composition can be administered to the egg-producing animal at least twice and at an interval from once every 2 weeks to once every 3 months.

In the methods provided herein, the egg produced by the hyperimmunized animal can include one or more antibodies to the human coronavirus. A product produced from the egg (a hyperimmunized egg product) can be a whole egg, an egg yolk, or purified or partially purified IgY. The hyperimmunized egg product can have a titer of at least 80,000 as measured by optical density. The titer of at least 80,000 can be maintained in the hyperimmunized egg product produced by the egg-producing animal for at least two weeks.

In the methods provided herein, the hyperimmunized egg product can be administered to the subject via any delivery mechanism known in the art. The hyperimmunized egg product can be administered to the subject as an oral rinse, by inhalation, by nasal drops, or by eye drops. The hyperimmunized egg product can be a liquid, a freeze-dried powder, or formulated to be administered as a spray. The hyperimmunized egg product can be a beverage. The hyperimmunized egg product can be formulated to contain GRAS components, or excipients to improve solubility, stability and dissolution, or both.

The method provided herein cam further include collecting a hyperimmunized egg from the egg-producing animal that has been hyperimmunized, and preparing a hyperimmunized egg product from the hyperimmunized egg. The hyperimmunized egg product from one or more eggs produced by the animal can be prepared by dehydrating, spray drying, or freeze drying of whole egg, yolk, or a purified IgY fraction from the one or more eggs. The hyperimmunized egg product can be formulated or prepare as nanoparticles or an emulsion. The emulsion can be a microemulsion or a nanoemulsion. The hyperimmunized egg product can be microencapsulated. The hyperimmunized egg product can include at least 20% more by weight of an IgY antibody specific to the coronavirus relative to a control egg product obtained from an egg-producing animal that is not hyperimmunized.

In the methods provided herein, the subject can be a human. In such methods, the coronavirus is a coronavirus that infects humans.

In the methods, administration of the hyperimmunized egg product to the subject can reduce binding of the coronavirus to an angiotensin converting enzyme 2 (ACE2) receptor protein in the subject. Administration of the hyperimmunized egg product to the subject can reduce entry of the coronavirus into a cell of the subject.

Administration of the hyperimmunized egg product to the subject can reduce binding of the coronavirus to an angiotensin converting enzyme 2 (ACE2) receptor protein in the subject and reduce entry of the coronavirus into a cell of the subject.

Also provided is one or more than one hyperimmunized egg produced by an animal that has been hyperimmunized with an antigen selected from the group consisting of i) a human coronavirus spike (S) protein, a human coronavirus S1 subunit protein, a human coronavirus S2 subunit protein, a human coronavirus receptor binding domain (RBD), and an immunogenic fragment thereof; ii) a human coronavirus nucleocapsid (N) protein, and an immunogenic fragment thereof; iii) a human angiotensin converting enzyme 2 (ACE2) receptor protein, and an immunogenic fragment thereof; iv) a human coronavirus selected from the group consisting of SARS CoV-1, MERS, SARS-CoV-2, HCoV-HKU1, HCoV-NL63, HCoV-OC43 and HCoV-229E; v) a human coronavirus S protein, or an immunogenic fragment thereof; vi) an S protein of SARS-CoV-2, or an immunogenic fragment thereof; vii) a receptor binding domain (RBD) of a human coronavirus S protein, or an immunogenic fragment thereof; viii) a receptor binding domain (RBD) of SARS-CoV-2, or an immunogenic fragment thereof; ix) the amino acid sequence of SEQ ID NO: 16, or an immunogenic fragment thereof; and x) the amino acid sequence of SEQ ID NO: 19, or an immunogenic fragment thereof. The level of antibodies to the antigen in the hyperimmunized egg is increased relative to an egg from an animal that has not been hyperimmunized. The antibodies in the hyperimmunized egg have a titer of at least 80,000 as measured by optical density.

Also provided is a hyperimmunized egg product obtained from the hyperimmunized egg produced by the methods provided herein. The hyperimmunized egg product can be whole egg, egg yolk, or purified or partially purified IgY antibody to the coronavirus. The hyperimmunized egg product can be dehydrated, spray dried or freeze dried. The hyperimmunized egg product can be formulated in nanoparticles or in an emulsion.

Also provided is a pharmaceutical composition comprising the hyperimmunized egg product provided herein and a pharmaceutically acceptable carrier. The pharmaceutically acceptable carrier can include a compound that is generally recognized as safe (GRAS), or can include an excipient that improves solubility, stability and/or dissolution, or can include both a compound that is generally recognized as safe (GRAS), or can include an excipient that improves solubility, stability and/or dissolution. The pharmaceutical composition can be formulated for oral, nasal or ocular administration. The pharmaceutical composition can be formulated for administration to the subject as an oral rinse, by inhalation, by nasal drops or by eye drops. The pharmaceutical composition can be a liquid, a freeze-dried powder, or formulated to be administered as a spray.

Also provided are methods of preparing a hyperimmunized egg product. The methods include a) hyperimmunizing an egg-producing animal with a composition comprising an antigen of a coronavirus; and b) preparing a hyperimmunized egg product from one or more eggs produced by the animal by dehydrating, spray drying, or freeze drying of whole egg, yolk or a purified IgY fraction from the one or more eggs. The antigen can include a human coronavirus spike (S) protein, a human coronavirus S1 subunit protein, a human coronavirus S2 subunit protein, a human coronavirus receptor binding domain (RBD), and an immunogenic fragment thereof. The antigen can include a human coronavirus nucleocapsid (N) protein, and an immunogenic fragment thereof. The antigen can include a human Angiotensin converting enzyme 2 (ACE2) receptor protein, and an immunogenic fragment thereof. The antigen can include a human coronavirus selected from the group consisting of Severe Acute Respiratory Syndrome coronavirus (SARS-CoV), Middle East Respiratory Syndrome coronavirus (MERS-CoV), Severe Acute Respiratory Syndrome coronavirus 2 (SARS-CoV-2), human coronavirus HKU1 (HCoV-HKU1), human coronavirus NL63 (HCoV-NL63), human coronavirus OC43 (HCoV-OC43) and human coronavirus 229E (HCoV-229E). The antigen can include a human coronavirus S protein, or an immunogenic fragment thereof. The antigen can include an S protein of SARS-CoV-2, or an immunogenic fragment thereof. The antigen can include a receptor binding domain (RBD) of a human coronavirus S protein, or an immunogenic fragment thereof. The antigen can include a receptor binding domain (RBD) of SARS-CoV-2, or an immunogenic fragment thereof. The antigen can include the amino acid sequence of SEQ ID NO: 16, or an immunogenic fragment thereof. The antigen can include the amino acid sequence of SEQ ID NO: 19, or an immunogenic fragment thereof. The antigen can be the amino acid sequence of SEQ ID NO: 19, or an immunogenic fragment thereof. The composition for hyperimmunizing the egg-producing animal can include two or more of the antigens mentioned in this paragraph.

BRIEF DESCRIPTION OF THE DRAWINGS

FIG. 1 shows SDS-PAGE analysis of CHO cell expressed recombinant RBD peptide. Lane 1: Molecular Weight Ladder, Lane 2: RBD.

FIG. 2 shows anti-RBD IgY binding titer values obtained in an ELISA assay using a purified IgY fraction from egg yolk against native RBD.

FIG. 3 shows inhibition of ACE2 binding to native RBD by IgY at various concentrations using ELISA and dot blot assays.

FIG. 4 shows binding of various concentrations of anti-RBD IgY to either native or delta RBD coated on the ELISA plate at 2 μg/ml. The bound IgY was detected using an anti-IgY HRP conjugated antibody and the binding is shown as OD at 405 nm.

FIG. 5 shows binding of biotinylated ACE to native or Delta variant RBD in a dot blot assay in the presence or absence of anti-RBD IgY. Data is shown as percent of biotinylated ACE2 binding (100%).

FIG. 6 shows the neutralizing activity of an oral rinse of an anti-RBD IgY antibody containing drink in an unvaccinated volunteer.

FIG. 7 shows the neutralizing activity of an oral rinse of an anti-RBD IgY antibody containing drink in a volunteer that received a single shot of a SARS-CoV2 vaccine.

FIG. 8 shows the neutralizing activity of an oral rinse of an anti-RBD IgY antibody containing drink in a volunteer that received two shots of a SARS-CoV2 vaccine.

FIG. 9 shows the neutralization of the native (Wuhan) strain of the SARS-CoV2 virus by anti-RBD IgY antibody.

FIG. 10 shows the neutralization of the Delta strain of the SARS-CoV2 virus by anti-RBD IgY antibody.

DETAILED DESCRIPTION AND PREFERRED EMBODIMENTS

The term "hyperimmunization" means repeated exposure to one or more antigens such that an immune response is elevated and maintained above the natural unexposed state.

A "hyperimmune state" refers to an elevated immune response in an egg producing animal that has been hyperimmunized.

The term "egg" as used herein refers to a whole egg (table, hyperimmunized or otherwise). The term "egg product" as used herein refers to a whole egg or any product or fraction obtained from a whole egg. In a particular embodiment, the egg product is an egg yolk, for example, an egg yolk powder. In another embodiment, the egg product is an egg white, for example, an egg white powder. In another embodiment, the egg product is obtained from a whole egg, for example, a whole egg powder (e.g. a spray-dried whole egg powder).

The term "control egg" refers to an egg obtained from an egg-producing animal that is not maintained in a hyperimmunized state, i.e. an animal that has not been hyperimmunized. The term "control egg product" refers to a control egg or an egg product obtained from a control egg.

The term "hyperimmunized egg" refers to a whole egg obtained from an egg-producing animal maintained in a hyperimmune state, i.e. an egg-producing animal that has been hyperimmunized. The term "hyperimmunized egg product" refers to a hyperimmunized egg or any product obtained from a hyperimmunized egg.

In certain embodiments, the hyperimmunized egg product is a concentrate. As used herein the term "concentrate" refers to a hyperimmunized egg product that is at least partially purified, such that the concentration of antibodies in the concentrate is greater than the concentration of antibodies in a hyperimmunized egg.

The term "egg powder" refers to a whole egg that has been dried. In some embodiments, the egg powder is spray-dried.

The term "egg-producing animal" means any oviparous animal, and includes any animal that lays an egg, such as avians, fish and reptiles.

The term "avian" refers to an animal that is a member of the class Aves. Avians include, but are not limited to, chickens, turkeys, geese, ducks, pheasants, quail, pigeons and ostriches.

The term "supranormal levels" means levels in excess of those found in eggs of egg-producing animals that are not hyperimmunized. For example, supranormal levels of an antibody to a particular antigen are levels of the antibody in excess of those found in eggs of egg-producing animals that are not hyperimmunized with the particular antigen.

The term "administer" means any method of providing a subject with a substance, including orally, intranasally, parenterally (intravenously, intramuscularly, or subcutaneously), rectally, topically or intraocularly.

The term "antigen" refers to a substance that is able to induce a humoral antibody and/or cell-mediated immune response rather than immunological tolerance. The term signifies the ability to stimulate an immune response as well as react with the products of it, e.g., an antibody.

As used herein, an "antibody" is a protein that includes at least one complementarity determining region that binds to a specific target antigen, e.g. antigen A, B, C, D, Co1, Co2, H, or ET-50 disclosed herein. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. In a particular embodiment, the antibody is a polyclonal antibody. The term "polyclonal antibody", as used herein, refers to a population of antibody molecules that that are capable of immunoreacting with different epitopes on a particular antigen. In a particular embodiment, the antibody is an IgY antibody.

As used herein, the term "effective amount" refers to the amount of hyperimmunized egg product which when administered to a subject is sufficient to prevent or treat coronavirus (e.g. SARS-CoV-2) infection. The effective amount can vary depending, for example, on the age, weight, and/or health of the subject to be treated.

Coronaviruses

Coronaviruses are positive-sense single-stranded RNA viruses belonging to the family Coronaviridae. These viruses mostly infect animals, including birds and mammals. In humans, they generally cause mild respiratory infections, such as those observed in the common cold. Prior to 2002, coronaviruses were not considered to be significant human pathogens. For example, human coronaviruses such as HCoV-229E and HCoV-OC43 resulted in only mild respiratory infections in healthy adults. In 2002, however, severe acute respiratory syndrome coronavirus (SARS-CoV) emerged in Guangdong Province, China. This virus rapidly spread to 29 different countries, resulting in 8,273 confirmed cases and 775 (9%) deaths. See U.S. Pat. No. 10,434,116.

Middle East respiratory syndrome coronavirus (MERS-CoV) is a more recently emerging virus. In 2012, Middle East respiratory syndrome coronavirus (MERS-CoV), was detected in a patient with severe respiratory disease in Saudi Arabia. The clinical features of MERS-CoV infection in humans range from asymptomatic to very severe pneumonia with the potential development of acute respiratory distress syndrome, septic shock, and multiorgan failure resulting in death. Dipeptidyl peptidase 4 (also known as CD26) has been identified as the functional cellular receptor for MERS-CoV. Ecological studies have suggested that the virus is of animal origin and is most closely related to coronaviruses found in a number of species of bats, with MERS-CoV viral sequences now found in camels in Saudi Arabia. See U.S. Pat. No. 10,434,116.

Severe Acute Respiratory Syndrome coronavirus 2 (SARS-CoV-2) has mostly recently emerged in 2019 as a significant human pathogen. After causing an initial cluster of Pneumonia in Wuhan City, Hubei Province, SARS-CoV-2 quickly spread through South East Asia and within a few weeks to Europe, Africa, and America. Initial estimates suggested a mortality rate of 2% and that ~18% of the cases show severe symptoms, although such estimates are still subject to changes. See Lucchese, 2020, Epitopes for a 2019-nCoV vaccine, Nature, doi.org/10.1038/s41423-020-0377-z.

Figure 1:
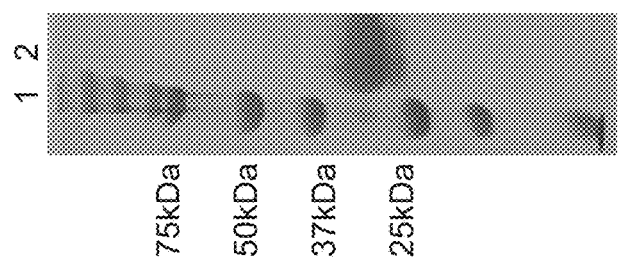

Two notable features of the SARS-CoV-2 genome have been identified. First, based on structural modelling and early biochemical experiments, SARS-CoV-2 appears to be optimized for binding to the human ACE2 receptor. Second, the highly variable spike (S) protein of SARS-CoV-2 has a polybasic (furin) cleavage site at the S1 and S2 boundary via the insertion of twelve nucleotides. Additionally, this event led to the acquisition of three predicted O-linked glycans around the polybasic cleavage site. See Andersen et al., 2020, The Proximal Origin of SARS-CoV-2, Virological.org.

The receptor binding domain (RBD) in the spike protein of SARS-CoV and SARS-related coronaviruses is the most variable part of the virus genome. Six residues in the RBD appear to be critical for binding to the human ACE2 receptor and determining host range. See Wan et al., 2020, Receptor recognition by novel coronavirus from Wuhan: An analysis based on decade-long structural studies of SARS. J. Virol. (2020) doi:10.1128/JVI.00127-20. Using coordinates based on the Urbani strain of SARS-CoV, they are Y442, L472, N479, D480, T487, and Y491I. The corresponding residues in SARS-CoV-2 are L455, F486, Q493, S494, N501, and Y505. Based on modeling and biochemical experiments, SARS-CoV-2 seems to have an RBD that can bind with high affinity to ACE2 from human, non-human primate, ferret, pig, and cat, as well as other species with high receptor homology. In contrast, SARS-CoV-2 can bind less efficiently to ACE2 in other species associated with SARS-like viruses, including rodents and civets. See Wan et al., cited above.

The phenylalanine (F) at residue 486 in the SARS-CoV-2 S protein corresponds to L472 in the SARS-CoV Urbani strain. Notably, in SARS-CoV cell culture experiments the L472 mutates to phenylalanine (L472F), which is predicted to be optimal for binding of the SARS-CoV RBD to the human ACE2 receptor. While these analyses suggest that SARS-CoV-2 may be capable of binding the human ACE2 receptor with high affinity, the interaction is not predicted to be optimal. Additionally, several of the key residues in the RBD of SARS-CoV-2 are different to those previously described as optimal for human ACE2 receptor binding. In contrast to these computational predictions, recent binding studies indicate that SARS-CoV-2 binds with high affinity to human ACE2. See Wrapp et al., 2020, Cryo-EM Structure of the 2019-nCoV Spike in the Prefusion Conformation. bioRxiv 2020.02.11.944462 doi:10.1101/2020.02.11.944462. Thus the SARS-CoV-2 spike appears to be the result of selection on human or human-like ACE2 permitting another optimal binding solution to arise.

The second notable feature of SARS-CoV-2 is a predicted polybasic cleavage site (RRAR) in the spike protein at the junction of S1 and S2, the two subunits of the spike protein. See Gallaher, 2020, Analysis of Wuhan coronavirus: deja vu. Virological.org 63. In addition to two basic arginines and an alanine at the cleavage site, a leading proline is also inserted; thus, the fully inserted sequence is PRRA. The strong turn created by the proline insertion is predicted to result in the addition of O-linked glycans to S673, T678, and S686 that flank the polybasic cleavage site. A polybasic cleavage site has not previously been observed in related lineage B betacoronaviruses and is a unique feature of SARS-CoV-2. Some human betacoronaviruses, including HCoV-HKU1 (lineage A), have polybasic cleavage sites, as well as predicted O-linked glycans near the S1/S2 cleavage site.

While the functional consequence of the polybasic cleavage site in SARS-CoV-2 is unknown, experiments with SARS-CoV have shown that engineering such a site at the S1/S2 junction enhances cell—cell fusion but does not affect virus entry. Polybasic cleavage sites allow effective cleavage by furin and other proteases, and can be acquired at the junction of the two subunits of the haemagglutinin (HA) protein of avian influenza viruses in conditions that select for rapid virus replication and transmission (e.g. highly dense chicken populations). HA serves a similar function in cell-cell fusion and viral entry as the coronavirus S protein. Acquisition of a polybasic cleavage site in HA, by either insertion or recombination, converts low pathogenicity avian influenza viruses into highly pathogenic forms. See Longping et al., 2014, J. Virol. 88: 1673-1683.

The Delta strain of SARS-CoV-2 virus previously emerged as a dominant strain. The Delta variant RBD is mutated with three amino acid changes from the native RBD. These mutations make this variant more transmissible and infective relative to the native strain.

Hyperimmunized Egg Product

In certain aspects, the present disclosure relates to a method of preparing a hyperimmunized egg product comprising: a) hyperimmunizing an egg-producing animal with a composition comprising an antigen selected from the group consisting of: i) a human coronavirus spike (S) protein, a human coronavirus S1 subunit protein, a human coronavirus S2 subunit protein, a human coronavirus receptor binding domain (RBD), and an immunogenic fragment thereof; ii) a human coronavirus nucleocapsid (N) protein, and an immunogenic fragment thereof; iii) a human ACE2 receptor protein, and an immunogenic fragment thereof; and iv) a human coronavirus selected from the group consisting of Severe Acute Respiratory Syndrome coronavirus (SARS-CoV), Middle East Respiratory Syndrome coronavirus (MERS-CoV), Severe Acute Respiratory Syndrome coronavirus 2 (SARS-CoV-2), human coronavirus HKU1 (HCoV-HKU1), human coronavirus NL63 (HCoV-NL63), human coronavirus OC43 (HCoV-OC43) and human coronavirus 229E (HCoV-229E); and b) preparing a hyperimmunized egg product from one or more eggs produced by the animal. In some embodiments, the antigen comprises or consists of a human coronavirus RBD, e.g., a SARS-CoV-2 RBD.

In certain aspects, the present disclosure relates to a hyperimmunized egg produced by an animal that has been hyperimmunized with an antigen selected from the group consisting of:_i) a human coronavirus spike (S) protein, a human coronavirus S1 subunit protein, a human coronavirus S2 subunit protein, a human coronavirus receptor binding domain (RBD), and an immunogenic fragment thereof;_ii) a human coronavirus nucleocapsid (N) protein, and an immunogenic fragment thereof;_iii) a human ACE2 receptor protein, and an immunogenic fragment thereof; and_iv) a human coronavirus selected from the group consisting of SARS CoV-1, MERS, SARS-CoV-2, HCoV-HKU1, HCoV-NL63, HCoV-OC43 and HCoV-229E, wherein the level of antibodies to the antigen in the hyperimmunized egg is increased relative to an egg from an animal that has not been hyperimmunized. In some embodiments, the antigen comprises or consists of a human coronavirus RBD, e.g., a SARS-CoV-2 RBD, or an immunogenic fragment thereof.

Egg-producing animals produce antibodies in blood and eggs that are specific to particular immunogens. For example, various genera of the class Aves, such as chickens (*Gallus domesticus*), turkeys, and ducks produce antibodies against antigens associated with avian diseases. LeBacq-Verheyden et al. (Immunology 27:683 (1974)) and Leslie, G. A., et al. (J. Med. 130:1337 (1969)), have quantitatively analyzed immunoglobulins of the chicken. Polson, A., et al. (Immunological Communications 9:495-514 (1980)) immunized hens against several proteins and natural mixtures of proteins, and detected IgY antibodies in the yolks of the eggs. Fertel, R., et al. (Biochemical and Biophysical Research Communications 102:1028-1033 (1981)) immunized hens against prostaglandins and detected antibodies in the egg yolk. Jensenius et al. (Journal of Immunological Methods 46:63-68 (1981)) provide a method of isolating egg yolk IgG for use in immunodiagnostics. Polson et al. (Immunological Communications 9:475-493 (1980)) describe antibodies isolated from the yolk of hens that were immunized with a variety of plant viruses.

U.S. Pat. No. 4,748,018 discloses a method of passive immunization of a mammal that comprises parenterally administering purified antibody obtained from the eggs of an avian that has been immunized against the corresponding antigen, and wherein the mammal has acquired immunity to the eggs.

U.S. Pat. No. 5,772,999, assigned to DCV-Biologics, discloses a method of preventing, countering or reducing chronic gastrointestinal disorders or Non-Steroidal Anti-Inflammatory Drug-induced (NSAID-induced) gastrointestinal damage in a subject by administering hyperimmunized egg and/or milk or fractions thereof to the subject.

An immunized egg is an egg which comes from an avian which has been immunized with, for example, a specific antigen or mixture of antigens. A hyperimmunized egg is an egg which comes from an avian which has been brought to a specific state of immunization by means of, for example, periodic booster administrations of antigens. Hyperimmunized eggs, no matter the type of antigen their avian maker has been administered, have been found to have various beneficial factors, including, as mentioned above, the treatment of chronic gastrointestinal disorders, NSAID-induced gastrointestinal damage (see U.S. Pat. No. 5,772,999) and anti-inflammatory effects due to the presence of an anti-inflammatory composition (see U.S. Application Publication No. US 2004/0156857).

One of the advantages of the hyperimmunized egg product is that it would have a higher and more consistent level of antibodies (e.g. IgY antibodies) to one or more of the antigens described herein compared to a control egg product or an egg product from a chicken that has been immunized with the antigen using standard immunization techniques. Typically standard immunization consists of an initial immunization followed by one or two booster immunization at 30 day intervals. In some embodiments, hyperimmunization comprises at least 4, 5, 6, 7, 8, 9 or 10 immunizations with an antigen described herein. In some embodiments, hyperimmunization comprises immunizing an egg producing animal with an antigen described herein at intervals of less than 30 days, less than 25 days, less than 20 days, less than 15 days, less than 10 days, or less than 5 days. In some embodiments, hyperimmunization comprises immunizing an egg producing animal with an antigen described herein at an interval of 1 week, 2 weeks, 3 weeks, 4 weeks, 1 month, 2 months or 3 months. Any of these values can be used to define a range for the interval at which the egg producing animal is immunized. For example, in some embodiments, the egg producing animal is hyperimmunized at an interval ranging from once every 2 weeks to once every 3 months, once per week to once every 3 months, or once every 2 weeks to once per month.

The hyperimmunized egg product can be produced by any egg-producing animal. It is preferred that the animal be a member of the class Aves or, in other words, an avian. Within the class Aves, domesticated fowl are preferred, but other members of this class, such as turkeys, ducks, and geese, are a suitable source of hyperimmune egg product. In a particular embodiment, the egg-producing animal is a chicken.

This special state of hyperimmunization is preferably achieved by administering an initial immunization, followed by periodic boosters with sufficiently high doses of specific antigens or mixtures of antigens. The dosage of the booster can be 10%, 20%, 30%, 40%, 50%, 60%, 70%, 80%, 90% or 100% of the dosage necessary to produce primary immunization of the egg-producing animal. Any of these percentages can be used to define a range for the dosage of the booster immunization. For example, in some embodiments, the dosage of the booster is 20%-80%, 30%-70%, or 50%-100% of the dosage necessary to produce primary immunization of the egg-producing animal. In a particular embodiment, the dosage of the booster immunization is 50% of the dosage of the primary immunization.

Having knowledge of the requirement for developing and maintaining a hyperimmune state, it is within the skill of the art to vary the amount of antigen administered, depending on the egg-producing animal genera and strain employed, in order to maintain the animal in the hyperimmune state.

The hyperimmune state can be produced by a single antigen or a combination of antigens. Hyperimmunization can be achieved by multiple exposures to multiple antigens, or multiple exposures to a single antigen.

Antigens for Hyperimmunization

In some embodiments, the antigens for hyperimmunization comprise one or more of:

i) a human coronavirus spike (S) protein, a human coronavirus S1 subunit protein, a human coronavirus S2 subunit protein, a human coronavirus receptor binding domain (RBD), and an immunogenic fragment thereof;

ii) a human coronavirus nucleocapsid (N) protein, and an immunogenic fragment thereof;

iii) a human ACE2 receptor protein, and an immunogenic fragment thereof; and iv) a human coronavirus selected from the group consisting of SARS CoV-1, MERS, SARS-CoV-2, HCoV-HKU1, HCoV-NL63, HCoV-OC43 and HCoV-229E.

In some embodiments, the antigens for hyperimmunization are selected from a SARS-CoV-2 spike protein, a SARS-CoV-2 S1 subunit protein, a SARS-CoV-2 S2 subunit protein, SARS-CoV-2, and immunogenic fragments thereof.

In some embodiments, the antigen comprises or consists of a human coronavirus RBD, e.g., a SARS-CoV-2 RBD, or an immunogenic fragment thereof.

In some embodiments, an immunogenic fragment as described herein comprises at least 10, 20, 30, 40, 50, 60, 70, 80, 90, 100, 200, 300, 400 or 500 amino acid residues.

The entire amino acid sequence of SARS-CoV-2 has been published as GenBank Accession No. MN908947.3, which is incorporated by reference herein in its entirety.

Coronavirus S Proteins

The membrane of coronaviruses harbors a trimeric transmembrane spike (S) glycoprotein which is essential for entry of virus particles into the cell. The S protein contains two functional domains: a receptor binding domain, and a second domain which contains sequences that mediate fusion of the viral and cell membranes. The S glycoprotein must be cleaved by cell proteases to enable exposure of the fusion sequences and hence is needed for cell entry.

The SARS-CoV-2 spike (S) protein is a viral surface glycoprotein that mediates binding to the human ACE2 receptor and cellular entry. The spike protein is a large type I transmembrane protein containing two subunits, an N-terminal S1 subunit and a C-terminal S2 subunit. S1 mainly contains a receptor binding domain (RBD), which is responsible for recognizing the cell surface receptor. S2 contains basic elements needed for the fusion of the virus to the cell membrane. The S protein plays key parts in the induction of neutralizing-antibody and T-cell responses, as well as protective immunity. See Gralinski, et al., 2020, Viruses 12.2, 135. A key feature of coronavirus S proteins is that the proteolytic cleavage events that lead to membrane fusion can occur both at the interface of the receptor binding (S1) and fusion (S2) domains (S1/S2), as well as in a novel position adjacent to a fusion peptide within S2 (S2'). See Millet et al., 2014, PNAS 111 (42): 15214-15219.

The amino acid sequence of the SARS-CoV-2 spike (S) protein is provided below (SEQ ID NO: 1). The S1/S2 cleavage site occurs between amino acid residues R685 and S686. Accordingly, the S1 domain of SARS-CoV-2 S protein is amino acid residues 1-685 of SEQ ID NO: 1, and the S2 domain of SARS-CoV-2 S protein is amino acid residues 686-1273 of SEQ ID NO: 1. The S2' cleavage site occurs between amino acid residues R815 and S816. See Hoffmann et al., 2020, Cell 181: 1-10, which is incorporated by reference herein in its entirety. The cleavage sites are shown in bold and underlined. In some embodiments, the antigen for hyperimmunization comprises or consists of the amino acid sequence of SEQ ID NO: 1, or an amino acid sequence having at least 80%, 85%, 90%, 95%, 96%, 97%, 98% or 99% sequence identity to SEQ ID NO: 1.

(SEQ ID NO: 1)
MFVFLVLLPLVSSQCVNLTTRTQLPPAYTNSFTRGVYYPDKVFRSSVLHS

TQDLFLPFFSNVTWFHAIHVSGTNGTKRFDNPVLPFNDGVYFASTEKSNI

IRGWIFGTTLDSKTQSLLIVNNATNVVIKVCEFQFCNDPFLGVYYHKNNK

SWMESEFRVYSSANNCTFEYVSQPFLMDLEGKQGNFKNLREFVFKNIDGY

FKIYSKHTPINLVRDLPQGFSALEPLVDLPIGINITRFQTLLALHRSYLT

PGDSSSGWTAGAAAYYVGYLQPRTFLLKYNENGTITDAVDCALDPLSETK

CTLKSFTVEKGIYQTSNFRVQPTESIVRFPNITNLCPFGEVFNATRFASV

YAWNRKRISNCVADYSVLYNSASFSTFKCYGVSPTKLNDLCFTNVYADSF

-continued
VIRGDEVRQIAPGQTGKIADYNYKLPDDFTGCVIAWNSNNLDSKVGGNYN

YLYRLFRKSNLKPFERDISTEIYQAGSTPCNGVEGFNCYFPLQSYGFQPT

NGVGYQPYRVVVLSFELLHAPATVCGPKKSTNLVKNKCVNFNFNGLTGTG

VLTESNKKFLPFQQFGRDIADTTDAVRDPQTLEILDITPCSFGGVSVITP

GTNTSNQVAVLYQDVNCTEVPVAIHADQLTPTWRVYSTGSNVFQTRAGCL

IGAEHVNNSYECDIPIGAGICASYQTQTNSPRRARSVASQSIIAYTMSLG

AENSVAYSNNSIAIPTNFTISVTTEILPVSMTKTSVDCTMYICGDSTECS

NLLLQYGSFCTQLNRALTGIAVEQDKNTQEVFAQVKQIYKTPPIKDFGGF

NFSQILPDPSKPSKRSFIEDLLFNKVTLADAGFIKQYGDCLGDIAARDLI

CAQKFNGLTVLPPLLTDEMIAQYTSALLAGTITSGWTFGAGAALQIPFAM

QMAYRFNGIGVTQNVLYENQKLIANQFNSAIGKIQDSLSSTASALGKLQD

VVNQNAQALNTLVKQLSSNFGAISSVLNDILSRLDKVEAEVQIDRLITGR

LQSLQTYVTQQLIRAAEIRASANLAATKMSECVLGQSKRVDFCGKGYHLM

SFPQSAPHGVVFLHVTYVPAQEKNFTTAPAICHDGKAHFPREGVFVSNGT

HWFVTQRNFYEPQIITTDNTFVSGNCDVVIGIVNNTVYDPLQPELDSFKE

ELDKYFKNHTSPDVDLGDISGINASVVNIQKEIDRLNEVAKNLNESLIDL

QELGKYEQYIKWPWYIWLGFIAGLIAIVMVTIMLCCMTSCCSCLKGCCSC

GSCCKFDEDDSEPVLKGVKLHYT

The SARS-CoV-2 spike protein contains a receptor binding domain (RBD) that directly binds to angiotensin receptor 2 (ACE2) present in human cells such as lung epithelium cells. The amino acid sequence of the SARS-CoV-2 RBD is underlined in the spike protein sequence above, and is provided herein as SEQ ID NO: 16. In some embodiments, the antigen for hyperimmunization comprises or consists of the amino acid sequence of SEQ ID NO: 16, or an amino acid sequence having at least 80%, 85%, 90%, 95%, 96%, 97%, 98% or 99% sequence identity to SEQ ID NO: 16.

The amino acid sequence of the SARS-CoV S protein is provided herein as SEQ ID NO: 2. The S1/S2 cleavage site occurs between amino acid residues R667 and S668. Accordingly, the S1 domain of SARS-CoV S protein is amino acid residues 1-667 of SEQ ID NO: 2, and the S2 domain of SARS-CoV S protein is amino acid residues 668-1255 of SEQ ID NO: 2. The S2' cleavage site occurs between amino acid residues R797 and S798. See Hoffmann et al., 2020, Cell 181: 1-10. In some embodiments, the antigen for hyperimmunization comprises or consists of the amino acid sequence of SEQ ID NO: 2, or an amino acid sequence having at least 80%, 85%, 90%, 95%, 96%, 97%, 98% or 99% sequence identity to SEQ ID NO: 2.

The amino acid sequence of the MERS S protein is provided herein as SEQ ID NO: 3. The S1/S2 cleavage site occurs between amino acid residues R748 and S749. Accordingly, the S1 domain of MERS S protein is amino acid residues 1-748 of SEQ ID NO: 3, and the S2 domain of SARS-CoV-2 S protein is amino acid residues 749-1353 of SEQ ID NO: 3. The S2' cleavage site occurs between amino acid residues R884 and S885. See Matsuyama et al., 2018, Journal of Virology 92(19): 1-12. In some embodiments, the antigen for hyperimmunization comprises or consists of the amino acid sequence of SEQ ID NO: 3, or an amino acid sequence having at least 80%, 85%, 90%, 95%, 96%, 97%, 98% or 99% sequence identity to SEQ ID NO: 3.

The amino acid sequence of the HKU1 S protein is provided herein as SEQ ID NO: 4. The S1/S2 cleavage site occurs between amino acid residues R756 and G757. Accordingly, the S1 domain of HKU1 S protein is amino acid residues 1-756 of SEQ ID NO: 4, and the S2 domain of HKU1 S protein is amino acid residues 757-1351 of SEQ ID NO: 4. The S2' cleavage site occurs between amino acid residues R900 and S901. See Matsuyama et al., 2018, Journal of Virology 92(19): 1-12. In some embodiments, the antigen for hyperimmunization comprises or consists of the amino acid sequence of SEQ ID NO: 4, or an amino acid sequence having at least 80%, 85%, 90%, 95%, 96%, 97%, 98% or 99% sequence identity to SEQ ID NO: 4.

The amino acid sequence of the NL63 S protein is provided herein as SEQ ID NO: 5. The S1/S2 junction occurs between amino acid residues V717 and S718. Accordingly, the S1 domain of NL63 S protein is amino acid residues 1-717 of SEQ ID NO: 5, and the S2 domain of NL63 S protein is amino acid residues 718-1356 of SEQ ID NO: 5. See Lin et al., 2008, Journal of General Virology 89: 1015-1024. In some embodiments, the antigen for hyperimmunization comprises or consists of the amino acid sequence of SEQ ID NO: 5, or an amino acid sequence having at least 80%, 85%, 90%, 95%, 96%, 97%, 98% or 99% sequence identity to SEQ ID NO: 5.

The amino acid sequence of the OC43 S protein is provided herein as SEQ ID NO: 6. The S1/S2 junction occurs between amino acid residues R757 and G758. Accordingly, the S1 domain of OC43 S protein is amino acid residues 1-757 of SEQ ID NO: 6, and the S2 domain of SARS-OC43 S protein is amino acid residues 758-1353 of SEQ ID NO: 6. See de Haan et al., 2008, Journal of Virology 82(12): 6078-6083. In some embodiments, the antigen for hyperimmunization comprises or consists of the amino acid sequence of SEQ ID NO: 6, or an amino acid sequence having at least 80%, 85%, 90%, 95%, 96%, 97%, 98% or 99% sequence identity to SEQ ID NO: 6.

The amino acid sequence of the 229E S protein is provided herein as SEQ ID NO: 7. The S1/S2 junction occurs between amino acid residues R567 and N568. Accordingly, the S1 domain of 229E S protein is amino acid residues 1-567 of SEQ ID NO: 7, and the S2 domain of 229E S protein is amino acid residues 568-1173 of SEQ ID NO: 7. See Bonnin et al., 2018, Journal of General Virology 99: 908-912. In some embodiments, the antigen for hyperimmunization comprises or consists of the amino acid sequence of SEQ ID NO: 7, or an amino acid sequence having at least 80%, 85%, 90%, 95%, 96%, 97%, 98% or 99% sequence identity to SEQ ID NO: 7.

Coronavirus N Protein

The coronavirus nucleocapsid (N) protein packages the positive strand viral genome RNA into a helical ribonucleocapsid (RNP) and plays a fundamental role during virion assembly through its interactions with the viral genome and membrane protein M. It also plays an important role in enhancing the efficiency of subgenomic viral RNA transcription as well as viral replication.

The amino acid sequence of the SARS-CoV-2 nucleocapsid (N) protein is provided herein as SEQ ID NO: 8. In some embodiments, the antigen for hyperimmunization comprises or consists of the amino acid sequence of SEQ ID NO: 9, or an amino acid sequence having at least 80%, 85%, 90%, 95%, 96%, 97%, 98% or 99% sequence identity to SEQ ID NO: 9.

The amino acid sequence of the SARS-CoV nucleocapsid (N) protein is provided herein as SEQ ID NO: 9. In some embodiments, the antigen for hyperimmunization comprises or consists of the amino acid sequence of SEQ ID NO: 9, or an amino acid sequence having at least 80%, 85%, 90%, 95%, 96%, 97%, 98% or 99% sequence identity to SEQ ID NO: 9.

The amino acid sequence of the MERS nucleocapsid (N) protein is provided herein as SEQ ID NO: 10. In some embodiments, the antigen for hyperimmunization comprises or consists of the amino acid sequence of SEQ ID NO: 10, or an amino acid sequence having at least 80%, 85%, 90%, 95%, 96%, 97%, 98% or 99% sequence identity to SEQ ID NO: 10.

The amino acid sequence of the HKU1 nucleocapsid (N) protein is provided herein as SEQ ID NO: 11. In some embodiments, the antigen for hyperimmunization comprises or consists of the amino acid sequence of SEQ ID NO: 11, or an amino acid sequence having at least 80%, 85%, 90%, 95%, 96%, 97%, 98% or 99% sequence identity to SEQ ID NO: 11.

The amino acid sequence of the NL63 nucleocapsid (N) protein is provided herein as SEQ ID NO: 12. In some embodiments, the antigen for hyperimmunization comprises or consists of the amino acid sequence of SEQ ID NO: 12, or an amino acid sequence having at least 80%, 85%, 90%, 95%, 96%, 97%, 98% or 99% sequence identity to SEQ ID NO: 12.

The amino acid sequence of the OC43 nucleocapsid (N) protein is provided herein as SEQ ID NO: 13. In some embodiments, the antigen for hyperimmunization comprises or consists of the amino acid sequence of SEQ ID NO: 13, or an amino acid sequence having at least 80%, 85%, 90%, 95%, 96%, 97%, 98% or 99% sequence identity to SEQ ID NO: 13.

The amino acid sequence of the 229E nucleocapsid (N) protein is provided herein as SEQ ID NO: 14. In some embodiments, the antigen for hyperimmunization comprises or consists of the amino acid sequence of SEQ ID NO: 14, or an amino acid sequence having at least 80%, 85%, 90%, 95%, 96%, 97%, 98% or 99% sequence identity to SEQ ID NO: 14.

Angiotensin converting enzyme 2 (ACE2) is the human receptor for SARS-CoV-2, SARS-CoV and the related human respiratory coronavirus NL63. ACE2 is a membrane-associated aminopeptidase expressed in vascular endothelia, renal and cardiovascular tissue, and epithelia of the small intestine and testes. A region of the extracellular portion of ACE2 that includes the first α-helix and lysine 353 and proximal residues of the N terminus of β-sheet 5 interacts with high affinity to the receptor binding domain of the SARS-CoV S glycoprotein. See Jia et al., 2005, J Virol. 79(23): 14614-14621; and Gralinski, et al., cited above. Because ACE2 is involved in cellular entry for some human coronaviruses, administering antibodies to ACE2 to a subject can help to block entry of the virus into the host cell, preventing or reducing replication of the virus in the subject. The amino acid sequence of human ACE2 is provided herein as SEQ ID NO: 15. In some embodiments, the antigen for hyperimmunization comprises or consists of the amino acid sequence of SEQ ID NO: 15, or an amino acid sequence having at least 80%, 85%, 90%, 95%, 96%, 97%, 98% or 99% sequence identity to SEQ ID NO: 15.

In addition to coronavirus peptide sequences, the antigen used for hyperimmunization can further comprise a linker sequence (e.g., SEQ ID NO: 17) and a histidine tag (e.g., SEQ ID NO: 18) to aid in purification of the antigen. In some embodiments, the antigen is a SARS-CoV-2 S protein RBD further comprising a linker sequence and a histidine tag. In a particular embodiment, the antigen comprises or consists of the amino acid sequence of SEQ ID NO: 19, or an amino acid sequence having at least 80%, 85%, 90%, 95%, 96%, 97%, 98% or 99% sequence identity to SEQ ID NO: 19.

Hyperimmunization Procedure

The following list of steps is an example of a preferred procedure used to bring an egg-producing animal to a heightened state of immunity from which the resultant hyperimmune egg or egg product can be administered to an avian:

1. Selecting one or more antigens.
2. Eliciting an immune response in the egg-producing animal by primary immunization.
3. Administering booster vaccines of one or more antigens of appropriate dosage to induce and maintain the hyperimmune state.

Step 1: The critical point in this step is that the antigen(s) must be capable of inducing immune and hyperimmune states in the egg-producing animal. In some embodiments, the egg-producing animal is immunized with an antigen selected from:

i) a human coronavirus spike (S) protein, a human coronavirus S1 subunit protein, a human coronavirus S2 subunit protein, a human coronavirus receptor binding domain (RBD), and an immunogenic fragment thereof;
ii) a human coronavirus nucleocapsid (N) protein, and an immunogenic fragment thereof;
iii) a human ACE2 receptor protein, and an immunogenic fragment thereof; and
iv) a human coronavirus selected from the group consisting of SARS CoV-1, MERS, SARS-CoV-2, HCoV-HKU1, HCoV-NL63, HCoV-OC43 and HCoV-229E.

In some embodiments, the antigen comprises or consists of a human coronavirus RBD, e.g., a SARS-CoV-2 RBD, or an immunogenic fragment thereof.

Step 2: For SARS CoV-1, MERS, SARS-CoV-2, HCoV-HKU1, HCoV-NL63, HCoV-OC43 and HCoV-229E, the vaccine can be either a killed or live-attenuated virus. The vaccine can be administered by any method that elicits an immune response. It is preferred that immunization be accomplished by administering the vaccine through intramuscular or subcutaneous injection. The preferred muscle for injection in an avian is the breast muscle. Dosage is preferably 0.05-5 milligrams of the immunogenic vaccine. Other methods of administration that can be used include intravenous injection, intraperitoneal injection, intradermal, rectal suppository, aerosol or oral administration.

It can be determined whether the vaccine has elicited an immune response in the egg-producing animal through a number of methods known to those having skill in the art of immunology. Examples of these include enzyme-linked immunosorbent assays (ELISA), tests for the presence of antibodies to the stimulating antigens, and tests designed to evaluate the ability of immune cells from the host to respond to the antigen. The minimum dosage of antigen necessary to induce an immune response depends on the vaccination procedure used, including the type of adjuvants and formulation of antigen(s) used as well as the type of egg-producing animal used as the host.

Step 3: The hyperimmune state is preferably induced and maintained in the target animal by repeated booster administrations of an appropriate dosage at fixed time intervals. The time intervals are preferably one week to three month intervals over a period of 6-12 months. However, it is essential that the booster administrations do not lead to immune tolerance. Such processes are well known in the art. Methods of preparing the hyperimmunized egg product are described, for example, in U.S. Pat. No. 6,803,035, which is incorporated by reference herein in its entirety.

In some embodiments, an antigen as described herein is formulated with an adjuvant. The adjuvant can selected from among Freund's complete adjuvant, Freund's incomplete adjuvant, a saponin, a biodegradable polymer, aluminum hydroxide, mineral oil, a surfactant, and combinations thereof. Exemplary saponins include QS-21 and Quil A. Exemplary biodegradable polymers include chitosan, zymosan, a poly(ethylene glycol)-block-poly(propylene glycol)-block-poly(ethylene glycol), such as Pluronic® L121 block copolymer, poly(lactic acid), poly(glycolic acid), poly(lactic-co-glycolic acid), polycaprolactone, and combinations thereof. Exemplary surfactants include polysorbate 80 and sorbitan trioleate.

In a particular embodiment, an antigen as described herein is formulated into a Freund's vaccine. In some embodiments, an antigen as described herein is formulated with an adjuvant selected from the group consisting of Freunds complete adjuvant, Freunds incomplete adjuvant and QS21. In the first vaccination, the egg-producing animal receives two 0.5 ml doses of each antigen. Two weeks later, one 0.5 ml dose of each antigen is administered to the egg-producing animal as a booster vaccination. An additional booster vaccination is performed 4 weeks after the first vaccination. The vaccines can be administered to breast tissue.

It is possible to use other hyperimmunization maintenance procedures or combination of procedures, such as, for example, intramuscular injection for primary immunization and intravenous injection for booster injections. Further procedures include simultaneously administering microencapsulated and liquid antigen, or intramuscular injection for primary immunization, and booster dosages by oral administration or parenteral administration by microencapsulation means. Several combinations of primary and hyperimmunization are known to those skilled in the art.

In certain embodiments, the hyperimmunized egg product comprises antibodies to an antigen selected from:

i) a human coronavirus spike (S) protein, a human coronavirus S1 subunit protein, a human coronavirus S2 subunit protein, a human coronavirus receptor binding domain (RBD), and an immunogenic fragment thereof;
ii) a human coronavirus nucleocapsid (N) protein, and an immunogenic fragment thereof;
iii) a human ACE2 receptor protein, and an immunogenic fragment thereof; and
iv) a human coronavirus selected from the group consisting of SARS CoV-1, MERS, SARS-CoV-2, HCoV-HKU1, HCoV-NL63, HCoV-OC43 and HCoV-229E.

In some embodiments, the hyperimmunized egg product comprises antibodies to a human coronavirus receptor binding domain (RBD), e.g., a SARS-CoV-2 RBD, or an immunogenic fragment thereof.

The antibody can be an IgA, IgM or IgY antibody. In a particular embodiment, the antibody is an IgY antibody.

The hyperimmunized egg or hyperimmunized egg product can contain an increased level of an antibody (e.g., an IgY antibody) specific to a particular antigen disclosed herein relative to a control egg or control egg product obtained from an egg-producing animal that is not hyperimmunized with the particular antigen. For example, in some embodiments the hyperimmunized egg or hyperimmunized egg product contains an increased level of an antibody that is specific to an antigen selected from:

i) a human coronavirus spike (S) protein, a human coronavirus S1 subunit protein, a human coronavirus S2 subunit protein, a human coronavirus receptor binding domain (RBD), and an immunogenic fragment thereof;

ii) a human coronavirus nucleocapsid (N) protein, and an immunogenic fragment thereof;

iii) a human ACE2 receptor protein, and an immunogenic fragment thereof; and iv) a human coronavirus selected from the group consisting of SARS CoV-1, MERS, SARS-CoV-2, HCoV-HKU1, HCoV-NL63, HCoV-OC43 and HCoV-229E, relative to a control egg or egg product obtained from an egg-producing animal that is not hyperimmunized. In some embodiments, the hyperimmunized egg or hyperimmunized egg product contains an increased level of an antibody that is specific to a human coronavirus receptor binding domain (RBD), e.g., a SARS-CoV-2 RBD, or an immunogenic fragment thereof.

In some embodiments, the hyperimmunized egg or egg product comprises at least 10%, 20%, 30%, 40%, 50%, 100%, 200%, 300%, 400% or 500% more antibody (e.g. IgY antibody) specific to a particular antigen disclosed herein by weight relative to a control egg or control egg product obtained from an egg-producing animal that is not hyperimmunized with the particular antigen.

The hyperimmunized egg or hyperimmunized egg product can contain increased levels of antibodies to two or more of the antigens disclosed herein, relative to a control egg or control egg product obtained from an egg-producing animal that is not hyperimmunized.

Comparisons of antibody titers in hyperimmunized egg products and control egg products can be determined by methods known in the art. For example, in one embodiment, eggs are collected and the antibody titers are monitored by ELISA at regular intervals. To determine antibody titers, total IgY is extracted from eggs using Pierce™ Chicken IgY Purification Kit (Thermo Fisher Scientific, Waltham, Mass.). Briefly, 2 mL of egg is mixed with five volumes of delipidation reagent and IgY is purified following the manufacturer's instructions. Spray dried egg powder samples are reconstituted in sterile PBS at 1 mg/mL, and filtered through a 0.22 μm membrane filter. Specific antibody titers in the isolated IgY or egg powder samples are measured by ELISA. Flat bottom, 96-well microtiter plates (Corning® Costar®, Corning, N.Y.) are coated with purified recombinant proteins (e.g. Antigens B, C, Co1, or Co2) at 10 μg/mL (100 μL/well) and incubated overnight at 4° C. The plates are washed twice with PBS containing 0.05% Tween 20 (Sigma-Aldrich, St. Louis, Mo.) and blocked with 100 μL/well of PBS containing 1% Bovine Serum Albumin (BSA) and incubated for 1 h at RT. Serially diluted (in PBS with 0.1% BSA) IgY samples from egg powder samples are added to the plates in triplicate wells (100 μL/well) and incubated for 2 h at RT with constant shaking. The plates are then washed with PBS-T and treated with peroxidase-conjugated rabbit anti-chicken IgY (IgG) antibody (1:500; Sigma), incubated for 30 min, followed by color development for 10 minutes with 0.01% tetramethylbenzidine substrate (Sigma) in 0.05 M Phosphate-Citrate buffer, pH 5.0. Bound antibodies are detected by measuring optical density at 450 nm ($OD_{450}$) using a microplate reader (Bio-Rad, Hercules, Calif.).

Antibody titers can be expressed by the highest fold dilution of egg product that still contains detectable antibodies as measured by optical density as described above. For example, an antibody titer of 1000 would indicate that a 1000-fold dilution of the egg product contains detectable antibody, but higher dilutions do not contain detectable antibody. In some embodiments, the antibody titer in the hyperimmunized egg product is at least 50,000, at least 80,000, at least 100,000, at least 160,000, at least 250,000, at least 320,000 at least 500,000, at least 640,00, or at least 1 million, 2 million, 3 million, 4 million, 5 million, 6 million, 7 million, 8 million, 9 million, 10 million, 11 million, 12 million, 13 million, 14 million, 15 million, 16 million, 17 million, 18 million, 19 million, or 20 million. In a particular embodiment, the antibody titer in the hyperimmunized egg product is at least 80,000.

In some embodiments, the hyperimmunized egg or egg product comprises at least 0.0001%, 0.0005%, 0.001%, 0.005%, 0.01%, 0.05%, or 0.1% by weight of an IgY antibody to a specific antigen disclosed herein. Typically, a whole chicken egg weighs approximately 60 grams without the shell, with the egg yolk weighing approximately 20 grams and the egg white weighing approximately 40 grams. In some embodiments, 3 grams of egg yolk contains approximately 20 grams of total IgY, such that a whole egg contains about 150-200 mg total IgY. In some embodiments, at least 1%, 2%, 3%, 4%, 5%, 6%, 7%, 8%, 9%, 10%, 11%, 12%, 13%, 14%, 15%, 16%, 17%, 18%, 19%, 20%, 25% or 30% of the total IgY in the hyperimmunized egg or egg product is specific to one of the antigens used for hyperimmunization.

Hyperimmunized eggs or egg products can contain an increased level of two or more antibodies (e.g. IgY antibodies), each of which is specific to a different antigen disclosed herein, relative to a control egg or egg product obtained from an egg-producing animal that is not hyperimmunized. The level of increase of each antibody (e.g. IgY antibody) in the hyperimmunized egg or egg product can be at least 10%, 20%, 30%, 40%, 50%, 100%, 200%, 300%, 400%, 500% or more by weight, relative to a control egg or egg product.

Compositions and Administration

In certain aspects, the present disclosure relates to a method for preventing or treating a coronavirus infection in a subject in need thereof, comprising administering to the subject a therapeutically effective amount of a hyperimmunized egg product obtained from an egg-producing animal, thereby preventing or treating coronavirus infection in the subject, wherein the hyperimmunized egg product comprises a therapeutically effective amount of one or more antibodies to the coronavirus.

Once the egg-producing animals have been sufficiently hyperimmunized, it is preferred that the eggs from these animals are collected and processed to produce a hyperimmunized egg product in administrable form. The hyperimmunized egg product can be prepared by dehydration, spray drying, or freeze drying of whole egg, yolk or purified IgY fraction. The dried hyperimmunized egg product can be mixed with an agent such as silicon or silicon derivatives that improves flow properties. The dried hyperimmunized egg product can comprise a desiccant. The hyperimmunized egg product can be stored at ambient temperature or refrigerated, for example, at 4° C.

In some embodiments the hyperimmunized egg product is encapsulated. Methods of encapsulating antibodies and other proteins are known in the art and are described, for example, in U.S. Pat. No. 7,105,158. Materials that are biodegradable and nonantigenic can be used as the encapsulating material. Encapsulating materials include, but are not limited to albumin, PLGA, globulin, natural and synthetic polymers, and thermoplastic polymers. Any polymer that is biocompatible and bioerodible can be used for encapsulation. A number of available crosslinking agents such as glutaraldehyde can be used to crosslink the encapsulating material. Additionally, the pharmaceutically delivered material can contain microspheres of encapsulated drug whereby the microspheres have different concentrations of crosslinking agent used, thereby creating a prolonged continuous release of the drug.

In some embodiments, the hyperimmunized egg product is in the form of a microparticle or nanoparticle, for example, an encapsulated microparticle or encapsulated nanoparticle. The microparticles and nanoparticles can have any shape. Typically the microparticles and nanoparticles are spherical. Other suitable shapes include, but are not limited to, flakes, triangles, ovals, rods, polygons, needles, tubes, cubes and cuboid structures. In certain embodiments, the microparticles have a diameter of less than 10, 9, 8, 7, 6, 5, 4, 3, 2, 1, 0.9, 0.8, 0.7, 0.6, 0.5, 0.4, 0.3, 0.2 or 0.1 micron(s). Any of these values can be used to define a range for the diameter of the microparticle. For example the diameter of the microparticle can be from about 0.1 to about 10 microns, from about 0.1 to about 1 micron, or from about 0.1 to about 2 microns. In other embodiments, larger microparticles or particles can be used. For example the microparticles can have a diameter ranging from 10 microns to 1000 microns. In certain embodiments, the nanoparticles have a diameter of less than 1000, 900, 800, 700, 600, 500, 400, 300, 200, 100, or 10 nm. Any of these values can be used to define a range for the diameter of the nanoparticle. For example the diameter of the nanoparticle can be from about 10 to about 1000 nm, from about 100 to about 1000 nm, or from about 10 to about 100 nm.

There are several processes whereby microparticles or nanoparticles can be encapsulated, including, for example, multi-walled microencapsulation, hot melt encapsulation, phase separation encapsulation, spontaneous emulsion, solvent evaporation microencapsulation, solvent removal microencapsulation, and coacervation. These methods are known in the art. Detailed descriptions of the methods are discussed in Mathiowitz et al., "Microencapsulation", in Encyclopedia of Controlled Drug Delivery, vol. 2, pp. 495-546, 1999, John Wiley & Sons, Inc. New York, N.Y., which is incorporated by reference herein in its entirety.

In some embodiments, the IgY antibody specific for an antigen disclosed herein is administered to the subject in a concentrated form. For example, in some embodiments, the IgY antibody is purified or partially purified and concentrated before administration to the subject. Methods of purifying and concentrating IgY antibodies from egg products are known in the art and are described, for example, in U.S. Pat. No. 5,367,054, which is incorporated by reference herein in its entirety.

In some embodiments, the hyperimmunized egg products described herein are used to treat coronavirus infection in a subject that has been infected with the coronavirus. In some embodiments, the subject has symptoms of coronavirus infection, e.g. fever, cough, shortness of breath, headache, and/or diarrhea. In some embodiments, the subject has Severe Acute Respiratory Syndrome (SARS), Middle East Respiratory Syndrome (MERS) or Coronavirus Disease-2019 (COVID-19) at the time of administration of the hyperimmunized egg product.

In some embodiments, the hyperimmunized egg products described herein are used to prevent coronavirus infection in a subject. For example, in some embodiments, the subject is not infected with coronavirus at the time of administration of the hyperimmunized egg product. In some embodiments, the hyperimmunized egg products described herein are used to prevent or reduce the development of symptoms resulting from coronavirus infection. For example, in some embodiments, the subject is infected with coronavirus, but is not yet exhibiting symptoms of coronavirus infection at the time of administration of the hyperimmunized egg product.

In a particular embodiment, the subject to which the hyperimmunized egg product is administered is a human. In a particular embodiment, the coronavirus is a coronavirus that infects humans.

The hyperimmunized egg product of the present invention is administered to a subject (e.g. a human) by any means that treats or prevents coronavirus infection in the subject. In certain embodiments, administration occurs by oral administration or by inhalation. In certain embodiments, the hyperimmunized egg product is administered to the subject as an oral rinse, by inhalation, or by nasal drops or eye drops. In a particular embodiment, the hyperimmunized egg product is administered as an oral rinse. Egg and egg yolk are natural food ingredients and are non-toxic and safe. In other embodiments, the hyperimmunized egg product can be administered by injection, for example, intravenous, subcutaneous, or intramuscular injection. In a particular embodiment, the hyperimmunized egg product is purified or partially purified IgY that is administered by intravenous injection. Any of several known pharmaceutically acceptable carriers can be used in the preparation of an injectable or otherwise administrable preparation, including phosphate buffered saline, saline, ethanol, propylene glycol and the like.

In some embodiments, the pharmaceutically acceptable carrier comprises a compound that is generally recognized as safe (GRAS) by the FDA. In some embodiments, the GRAS compound is selected from acetic acid, aconitic acid, adipic acid, alginic acid, α-amylase enzyme preparation from *Bacillus stearothermophilus*, benzoic acid, bromelain, caprylic acid, mixed carbohydrase and protease enzyme product, citric acid, catalase (bovine liver), lactic acid, enzyme-modified lecithin, linoleic acid, malic acid, potassium acid tartrate, propionic acid, stearic acid, succinic acid, sulfuric acid, tannic acid, tartaric acid, diacetyl tartaric acid esters of mono- and diglycerides, agar-agar, brown algae, red algae, ammonium alginate, ammonium bicarbonate, ammonium carbonate, ammonium chloride, ammonium hydroxide, ammonium citrate, dibasic, ammonium phosphate (monobasic), ammonium phosphate (dibasic), ammonium sulfate, bacterially-derived carbohydrase enzyme preparation, bacterially-derived protease enzyme preparation, bentonite, benzoyl peroxide, n-butane and iso-butane, calcium acetate, calcium alginate, calcium carbonate, calcium chloride, calcium citrate, calcium gluconate, calcium glycerophosphate, calcium hydroxide, calcium iodate, calcium lactate, calcium oxide, calcium pantothenate, calcium propionate, calcium stearate, calcium sulfate, carbon dioxide, beta-carotene, cellulase enzyme preparation derived from *Trichoderma longibrachiatum*, clove and its derivatives, cocoa butter substitute, copper gluconate, copper sulfate, corn silk and corn silk extract, cuprous iodide, L-cysteine, L-cysteine monohydrochloride, dextrin, diacetyl, dill and its derivatives, enzyme-modified fat, ethyl alcohol, ethyl formate, ferric ammonium citrate, ferric chloride, ferric citrate, ferric phosphate, ferric pyrophosphate, ferric sulfate, ferrous ascorbate, ferrous carbonate, ferrous citrate, ferrous fumarate, ferrous gluconate, ferrous lactate, ferrous sulfate, ficin, garlic and its derivatives, glucono delta-lactone, corn gluten, wheat gluten, glyceryl monooleate, glyceryl monostearate, glyceryl behenate, glyceryl palmitostearate, acacia (gum arabic), gum ghatti, guar gum, locust (carob) bean gum, karaya gum (sterculia gum), gum tragacanth, helium, hydrogen peroxide, inositol, insoluble glucose isomerase enzyme preparations, iron, elemental, isopropyl citrate, lactase enzyme preparation from *Candida pseudotropicalis*, lactase enzyme preparation from *Kluyveromyces lactis*, lecithin, licorice and licorice derivatives, ground limestone, animal lipase, lipase enzyme preparation derived from *Rhizopus niveus*, magnesium carbonate, magnesium chloride, magnesium hydroxide, magnesium oxide, magnesium phosphate, magnesium stearate, magnesium sulfate, malt, maltodextrin, malt syrup (malt extract), manganese chloride, manganese citrate, manganese gluconate, manganese sulfate, menhaden oil, methylparaben, microparticulated protein product, monk fruit sweetener, mono- and diglycerides, monosodium phosphate derivatives of mono- and diglycerides, niacin, niacinamide, nickel, nisin preparation, nitrogen, nitrous oxide, peptones, rapeseed oil, ox bile extract, ozone, pancreatin, papain, pectins, pepsin, potassium alginate, potassium bicarbonate, potassium carbonate, potassium chloride, potassium citrate, potassium hydroxide, potassium iodide, potassium iodate, potassium lactate, potassium sulfate, propane, propyl gallate, propylene glycol, propylparaben, pyridoxine hydrochloride, rennet (animal-derived) and chymosin preparation (fermentation-derived), riboflavin, riboflavin-5-phosphate (sodium), rue, Oil of rue, shea nut oil, sodium acetate, sodium alginate, sodium benzoate, sodium bicarbonate, sodium carbonate, sodium citrate, sodium diacetate, sodium hydroxide, sodium hypophosphite, sodium lactate, sodium metasilicate, sodium propionate, sodium sesquicarbonate, sodium tartrate, sodium potassium tartrate, sodium thiosulfate, sorbitol, stannous chloride (anhydrous and dihydrated), starter distillate, stearyl citrate, *stevia*, sucralose, sucrose, sorn sugar, invert sugar, corn syrup, high fructose corn syrup, thiamine hydrochloride, thiamine mononitrate, α-tocopherols, triacetin, tributyrin, triethyl citrate, trypsin, urea, urease enzyme preparation from *Lactobacillus fermentum*, vitamin A, vitamin B12, vitamin D, beeswax (yellow and white), candelilla wax, carnauba wax, whey, reduced lactose whey, reduced minerals whey, whey protein concentrate, whey protein isolate, Baker's yeast extract, zein, and aminopeptidase enzyme preparation derived from *Lactococcus lactis*.

In some embodiments, the hyperimmunized egg product is administered through drinking water. In some embodiments, the hyperimmunized egg product is administered as a beverage, e.g., a beverage comprising one or more flavoring agents, coloring agents and/or sweeteners. In certain embodiments, the hyperimmunized egg product is administered as a composition comprising one or more additional compounds, e.g. a nutrient or probiotic. For example, in one embodiment, the hyperimmunized egg product of the invention is integrated into a dietary supplement. One method for preparing the egg of the invention to be incorporated into a dietary supplement involves drying the egg into an egg powder. Although various methods are known for drying eggs, spray drying is a preferred method. The process of spray drying eggs is well known in the art. In some embodiments, the composition is an aqueous solution comprising the hyperimmunized egg product. In some embodiments, the hyperimmunized egg product is a liquid, a freeze-dried powder, or formulated to be administered as a spray.

In certain embodiments, whole eggs are divided into separate fractions such as egg yolks and egg whites. For example, it is generally known in the art that IgY antibody is found in egg yolks. Accordingly, those having ordinary skill in the art would clearly recognize that separation of egg yolks could provide more potent fractions or elimination of undesirable components, and would allow for other modes of administration such as administering hyperimmunized egg product parenterally, subcutaneously, intravenously, intramuscularly, intraperitoneally, intranasally, intraocularly, orally or topically. Such further separation will provide for the ability to make encapsulated products and compositions comprising said egg or fraction thereof.

The hyperimmune egg product is preferably administered to the subject in an amount that is immunologically effective in treating or preventing coronavirus infection. Dosage and duration of the administration will depend upon the particular condition of the subject. In some embodiments, the hyperimmunized egg product is administered to the subject for at least 5, 6, 7, 8, 9, 10, 11, 12, 13, 14, 15, 20, 25, 30, 60, 90, 180 or 365 days. The hyperimmunized egg product can be administered to the subject 1, 2, 3, 4, 5, 6, 7, 8, 9, 10 or more times per day. Any of these values can be used to define a range for the number of times the hyperimmunized egg product can be administered to the subject per day. For example, in some embodiments the hyperimmunized egg product is administered to the subject 1-2 times per day, 1-3 times per day, or 1-4 times per day. In some embodiments, the hyperimmunized egg product is administered to the subject at least twice per day. In some embodiments, the hyperimmunized egg product is administered to subject at least once per day. In some embodiments, the hyperimmunized egg product is administered to the subject daily. In some embodiments, the hyperimmunized egg product is administered to the subject once every two days. In some embodiments, the hyperimmunized egg product is administered to the subject once every three days. In some embodiments, the hyperimmunized egg product is administered to the subject once per week. In a particular embodiment, the hyperimmunized egg product is administered to the subject once per day for more than 10 consecutive days.

In some embodiments, daily amounts ranging from less than one to several whole, hyperimmune eggs (or hyperimmune egg products containing the equivalent of less than one to several whole, hyperimmune eggs) can be administered to the subject depending on the particular circumstance of the condition. More potent fractions can be separated and concentrated by methods well-known in the art, from several hundred eggs.

In certain embodiments, the effective amount of the hyperimmunized egg product administered to a subject (e.g. a human) is 0.1, 0.2, 0.3, 0.4, 0.5, 0.6, 0.7, 0.8, 0.9, 1, 2, 3, 4, 5, 6, 7, 8, 9, 10, 20, 30, 40 or 50 grams per day. For example, in some embodiments, 0.1, 0.2, 0.3, 0.4, 0.5, 0.6, 0.7, 0.8, 0.9, 1, 2, 3, 4, 5, 6, 7, 8, 9, 10, 20, 30, 40 or 50 grams per day of whole egg are administered to the subject. In some embodiments, 0.1, 0.2, 0.3, 0.4, 0.5, 0.6, 0.7, 0.8, 0.9, 1, 2, 3, 4, 5, 6, 7, 8, 9, 10, 20, 30, 40 or 50 grams per day of egg yolk are administered to the subject. In some embodiments, 0.1, 0.2, 0.3, 0.4, 0.5, 0.6, 0.7, 0.8, 0.9, 1, 2, 3, 4, 5, 6, 7, 8, 9 or 10 grams per day of dried egg yolk or dried whole egg are administered to the subject. Any of these values can be used to define a range for the effective amount of the hyperimmunized egg product administered to the mammal. For example, in some embodiments the effect amount of the hyperimmunized egg product is between 0.1 and 10 grams, between 0.5 to 6 grams, or between 1 and 5 grams per day. In a particular embodiment, 3 grams of egg yolk are administered to the subject (e.g. a human) per day.

In certain embodiments, the composition comprises at least 0.01%, 0.05%, 0.1%, 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98% or 99% w/w of the hyperimmunized egg product. Any of these values can be used to define a range for the concentration of the hyperimmunized egg product in the composition. For example, in some embodiments, the composition comprises between 0.01% and 50%, between 0.1% and 50%, or between 1% and 50% w/w of the hyperimmunized egg product.

In some embodiments, the hyperimmunized egg product is administered to a subject in combination with one or more additional therapeutic agents. In some embodiments, the one or more additional therapeutic agents comprise one or more antibodies (e.g., one or more monoclonal antibodies) that specifically bind to SARS-CoV-2. In some embodiments, the one or more monoclonal antibodies bind the RBD of the S protein of SARS-CoV-2. In some embodiments, the additional therapeutic agent is a compound (e.g., a small molecule or peptide) that interferes with entry of the coronavirus (e.g., SARS-CoV-2) into a human cell. In some embodiments, the additional therapeutic agent is a compound (e.g., a small molecule or peptide) that interferes with replication of the coronavirus (e.g., SARS-CoV-2) in a human cell. In some embodiments, the additional therapeutic agent is an antiviral agent, an anti-inflammatory agent, a steroid, or an anti-thrombotic agent. In some embodiments, the antiviral agent is selected from the group consisting of remdesivir, lopinavir and flapinavir.

Description of Sequences

| SEQ ID NO: | Description |
|---|---|
| 1 | Amino acid sequence of the SARS-CoV-2 spike (S) protein |
| 2 | Amino acid sequence of the SARS-CoV S protein |
| 3 | Amino acid sequence of the MERS S protein |
| 4 | Amino acid sequence of the HKU1 S protein |
| 5 | Amino acid sequence of the NL63 S protein |
| 6 | Amino acid sequence of the OC43 S protein |
| 7 | Amino acid sequence of the 229E S protein |
| 8 | Amino acid sequence of the SARS-CoV-2 nucleocapsid (N) protein |
| 9 | Amino acid sequence of the SARS-CoV nucleocapsid (N) protein |
| 10 | Amino acid sequence of the MERS nucleocapsid (N) protein |
| 11 | Amino acid sequence of the HKU1 nucleocapsid (N) protein |
| 12 | Amino acid sequence of the NL63 nucleocapsid (N) protein |
| 13 | Amino acid sequence of the OC43 nucleocapsid (N) protein |
| 14 | Amino acid sequence of the 229E nucleocapsid (N) protein |
| 15 | Amino acid sequence of human ACE2 |
| 16 | Amino acid sequence of the RBD domain within the spike protein 1 of the native strain of SARS-CoV-2 |
| 17 | Linker in the RBD recombinant peptide used for hyperimmunization |
| 18 | Histidine tag in the RBD recombinant protein used for hyperimmunization |
| 19 | RBD recombinant peptide used for hyperimmunization, contains the linker and histidine tag |

EXAMPLES

Example 1. Preparation and Evaluation of Anti-RBD IgY Antibodies

1. SARS-CoV-2 Spike Protein 1 RBD Domain Used to Create a Peptide Antigen for Chicken Immunization The amino acid sequence of the RBD domain (SEQ ID NO: 16) within the spike protein 1 of the native strain of SARS-CoV-2 was used to create an RBD peptide for chicken immunization to raise IgY antibodies. A linker (GGSGGGSGGGS, SEQ ID NO: 17) and histidine tag (HHHHHH: SEQ ID NO: 18) were added to the C-terminus of the RBD domain, as shown below.

```
                                              (SEQ ID NO: 19)
VFNATRFASV YAWNRKRISN CVADYSVLYN SASFSTFKCY

GVSPTKLNDL CFTNVYADSF VIRGDEVRQI APGQTGKIAD

YNYKLPDDFT GCVIAWNSNN LDSKVGGNYN YLYRLFRKSN

LKPFERDIST EIYQAGSTPC NGVEGFNCYF PLQSYGFQPT

NGVGYQPYRV VVLSFELLHA PATVCGPKKS TNLVKNKCVN

FNFNGLTGTG VLTESNKKFL PFQQFGRDIA DTTDAVRDPQ

TLEILDITPC SFGGVSVITP GTNTSNQVAV LYQDVNCTEV

PVAIHADQLT PTWRVYSTGS NVFQ GGSGGGSGGGSHHHHHH
```

2. SDS PAGE Analysis of CHO Cell Expressed Recombinant RBD Peptide

A CHO expression system was used to express and purify the recombinant His tagged RBD domain which was then used for hyperimmunization. FIG. 1 shows the purity of the RBD peptide obtained (>90% purity) as determined by a Coomassie-stained 12% Reducing Tris-Glycine SDS-PAGE.

3. Immunization of Chickens with Recombinant RBD and Harvesting of Anti-RBD IgY from Egg Yolk The RBD domain peptide described above was used to vaccinate chickens. The chickens received several booster shots of the peptide to achieve high titers of anti-RBD IgY in the eggs laid by the chickens using a protocol similar to one described previously (see Yang et al., African Journal of Biotechnology Vol. 10(41), pp. 8146-8150). Before processing of the egg yolk or whole egg, the *Salmonella* and yeast contaminants in the solution were sterilized by heat treatment. The sterilization temperature was 61° C. and the sterilization time was 3 to 5 minutes.

IgY titer was determined by ELISA using partially (>85%) purified total IgYs from egg yolk.

Figure 2:
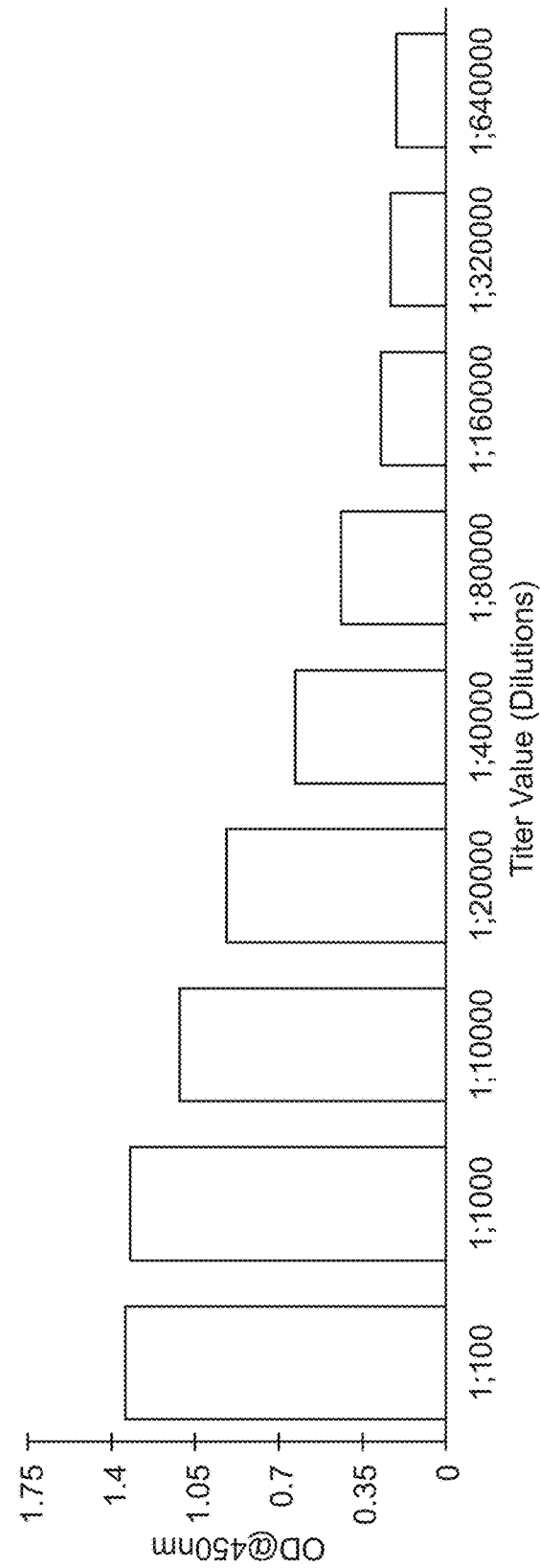

ELISA was carried out by the standard protocol. Briefly, RBD peptide (1 µg) was coated on the plate, and anti-RBD IgY preparation from egg yolk was diluted as shown and applied to the plate to bind RBD peptide. The plate was blocked and washed following each addition as per standard ELISA protocol. The color was developed by complexing HRP-conjugated anti-IgY antibody and HRP standard as per standard ELISA protocols. The results demonstrate that high titers of IgY antibodies (>80,000 dilution also shows signal twice above background OD) were obtained against RBD immunized chicken egg yolk (see Table 1 below and FIG. 2). These results indicate that the IgYs have strong cross reactivity towards RBD. The >85% purified IgY fraction from egg yolk was then used for all experiments shown below.

TABLE 1

| Titer values obtained in I-ELISA assay | | | | | | | | | | | |
|---|---|---|---|---|---|---|---|---|---|---|---|
| 1;100 | 1;1000 | 1;10000 | 1;20000 | 1;40000 | 1;80000 | 1;160000 | 1;320000 | 1;640000 | PC | CPC | NC |
| 1 | 2 | 3 | 4 | 5 | 6 | 7 | 8 | 9 | 10 | 11 | 12 |
| A 1.341 | 1.295 | 1.093 | 0.893 | 0.635 | 0.452 | 0.277 | 0.237 | 0.188 | 1.329 | 0.192 | 0.168 |
| B 1.359 | 1.357 | 1.136 | 0.956 | 0.627 | 0.434 | 0.268 | 0.243 | 0.233 | 1.426 | 0.197 | 0.183 |

PC = positive control where a known antigen X was coated on the plate and anti-X-IgY was applied to bind to antigen X.
CPC = Only anti-RBD or anti-X antibodies were applied. No antigen.
NC = Antigen X was coated on the plate and anti-RBD IgY antibodies were applied to check for any cross reactivity.

Example 2. Measurement of Neutralizing Activity of Anti-RBD IgY Antibodies by ELISA and Dot Blot Assays Two separate methods were used to characterize the neutralizing activity of the anti-RBD IgY: 1) a commercially available competition ELISA assay from Genscript, USA, and
2) a dot blot assay in which the nitrocellulose membrane was coated with ACE2 and biotinylated RBD was used to monitor the binding (Saxena, et al., bioRxiv. doi: 10.1101/2021.05.02.442384. 2021).

SARS-CoV2 enters human host cells using the receptor binding domain (RBD) on its surface spike protein. RBD directly binds to angiotensin receptor 2 (ACE2) present on human cells such as lung epithelium cells. SARS-CoV2 vaccines work by eliciting neutralizing antibodies which interfere with this binding, with the end result that the virus cannot enter the human cells.

We have designed a cell free dot blot competition assay to measure the binding of biotinylated RBD (B-RBD) to human ACE2 using a simple and rapid nitrocellulose membrane assay. Briefly, ACE2 was deposited on the membrane and B-RBD was added to it, and bound B-RBD was detected by adding streptavidin-HRP followed by HRP detection substrate. When the assay is performed in the presence of RBD neutralizing antibody, the amount of B-RBD bound to ACE-2 is reduced in proportion to the presence of neutralizing antibodies. Persons who are infected and those who are vaccinated against SARS-CoV2 produce an immune responses to the viral proteins, including the RBD of the S1 protein. Antibodies that bind RBD and block RBD's ability to bind ACE2 are neutralizing antibodies, and these are believed to be responsible for preventing viral infection and reducing the onset and severity of the disease.

Using this assay, anti-COVID-19 neutralizing antibodies can be tested in multiple body fluids such as blood, saliva and others. Laboratory-based tests using serum isolated from blood of subjects have received EUA (Emergency Use Authorization) from various regulatory bodies to screen for the presence of neutralizing antibodies, the levels of which are indicative of protection from COVID-19. We used this assay to evaluate the effectiveness of the anti-RBD IgY in neutralizing RBD-ACE2 binding following administration to subjects. The test is able to qualitatively and semi-quantitatively measure RBD binding to ACE2, and IgY's ability to neutralize the binding, which is indicative of performance. The dot blot is a competitive assay wherein higher neutralizing activity results in lower blot color formation. The dot blot stain color intensity was captured and quantitated using ImageJ software analysis.

Results

As shown in FIG. 3, a comparison of the two methods shows similar neutralizing activity by the two assays. Using a concentration curve, we were able to determine that the anti-RBD IgY inhibited the binding of RBD to ACE2 similarly with $IC_{50}$ of inhibition being 0.2 mg/ml in the ELISA assay and 0.1 mg/ml in the dot blot assay.

The Delta strain of SARS-CoV-2 virus previously emerged as a dominant strain. The Delta variant RBD is mutated with three amino acid changes from the native RBD. These mutations make this variant more transmissible and infective relative to the native strain. We tested whether the IgY antibody raised as above will a) bind to delta RBD and b) neutralize the binding of Delta RBD to ACE2 using ELISA and dot blot assays respectively.

Figure 4:
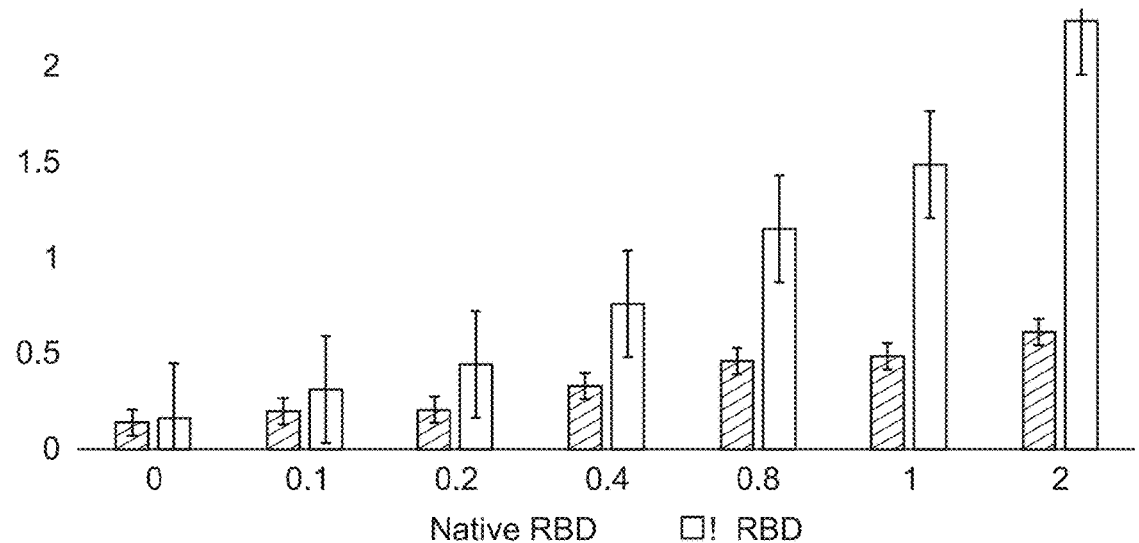

FIG. 4 shows a head to head comparison of direct binding of the anti-RBD IgY to either native or Delta RBD (obtained commercially from Pentavalent Biosciences Private Limited, India) coated on an ELISA plate. Bound IgY was detected using and biotinylated anti-IgY antibody. As shown in FIG. 4, the IgY bound directly to both native and Delta RBD effectively at various concentrations, with binding to Delta RBD being almost 4-fold higher, suggesting that the IgY strongly recognizes Delta variant RBD.

Figure 5:
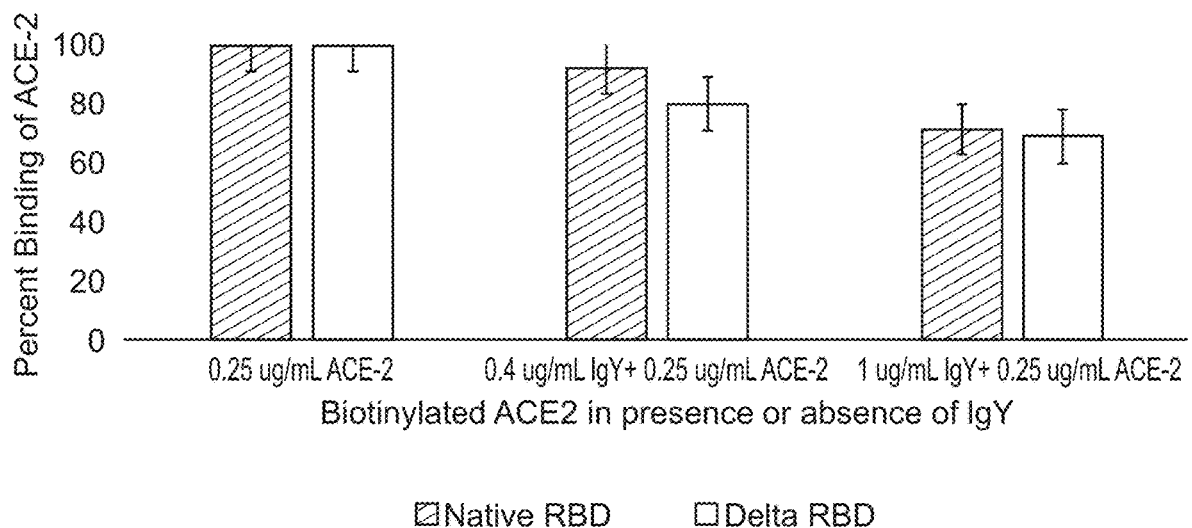

Using the dot blot assay, we also determined if the IgY antibody of the invention can inhibit the binding of ACE2 to delta RBD. As shown in FIG. 5, at the concentrations of IgY used (1 µg/ml and 0.4 µg/ml) we found that IgY antibody inhibited biotinylated ACE2 interaction with both native RBD (91% and 75% ACE2 binding at 0.4 and 1 µg/ml IgY) and Delta RBD (75% and 69% ACE 2 binding at 0.4 and 1 ug/ml IgY), suggesting its utility in neutralizing Delta RBD binding to ACE2.

Example 3. Evaluation of Anti-RBD IgY in a Plaque Reduction Neutralization Test (PRNT)

The effect of the anti-RBD IgY described in Example 1 against SARS-CoV-2 was also examined in Vero cells (a monkey kidney cell line) in a plaque reduction neutralization test (PRNT). Since the anti-RBD IgY neutralize the binding of RBD to ACE2, we determined whether anti-RBD IgY reduces viral entry into the cells.

Viral Neutralization Assay

The primary aim of this study was to determine if the semi-purified anti-RBD IgY described in Example 1 was able to neutralize SARS-CoV2 and prevent the virus from entering Vero cells and subsequently reduce plaque formation.

The protocol was followed according to WHO guidelines. Briefly, the antibody samples were diluted sequentially 2-fold, up to 6 dilutions, and then incubated with equal volumes SARS-CoV2 (Wuhan strain) in a 1:1 ratio, and this mixture was allowed to incubate for 1 hr at 37° C. and then added onto the Vero cell monolayer and further incubated for 24 hrs at 37° C. Virus without any antibody served as a positive control for plaque formation. The number of plaques (pfu) formed with the control was compared with the plaque numbers obtained by pre-incubation of virus with various concentrations of antibody. Plaques were counted manually and % neutralization was calculated. Data was reported as $PRNT_{50}$, which represent the value of antibody concentration that is able to reduce the number of observed viral plaques by 50%, i.e., to neutralize 50% of the SARS CoV-2 virus utilized in the assay.

TABLE 2

Samples Used for the Viral Neutralization assay

| | |
|---|---|
| Sample 1 | Phosphate buffered saline ONLY |
| Sample 2 | 5 mg of semi purified anti-RBD IgY in 100 mL Phosphate buffered saline |
| Sample 3 | 1 mg of semi purified anti-RBD IgY in 100 mL Phosphate buffered saline |

Results:

Table 3 below shows that at the two concentrations tested, IgY was able to reduce plaque formation effectively, suggesting its effectiveness in reducing virus binding and entry into Vero cells. Specifically, Sample 1 (control) was not able to neutralize SARS-CoV2 virus, whereas samples 2 and 3 (anti-RBD IgY) were able to neutralize SARS-CoV2 virus with $PRNT_{50}$ values of 4.61 and 1.28 IU/ml respectively. Thus, the viral neutralization assays clearly showed that the semi-purified anti-RBD IgY was able to neutralize SARS-CoV2 Wuhan strain in a dose dependent manner.

TABLE 3

Neutralization of SARS-CoV2 as determined by the plaque reduction neutralization test (PRNT)

| Sample No. | $PRNT_{50}$ (IU/ml) | Result (Positive or Negative) |
|---|---|---|
| 1 | NA | Negative |
| 2 | 4.61 | Positive |
| 3 | 1.28 | Positive |

Figure 7:
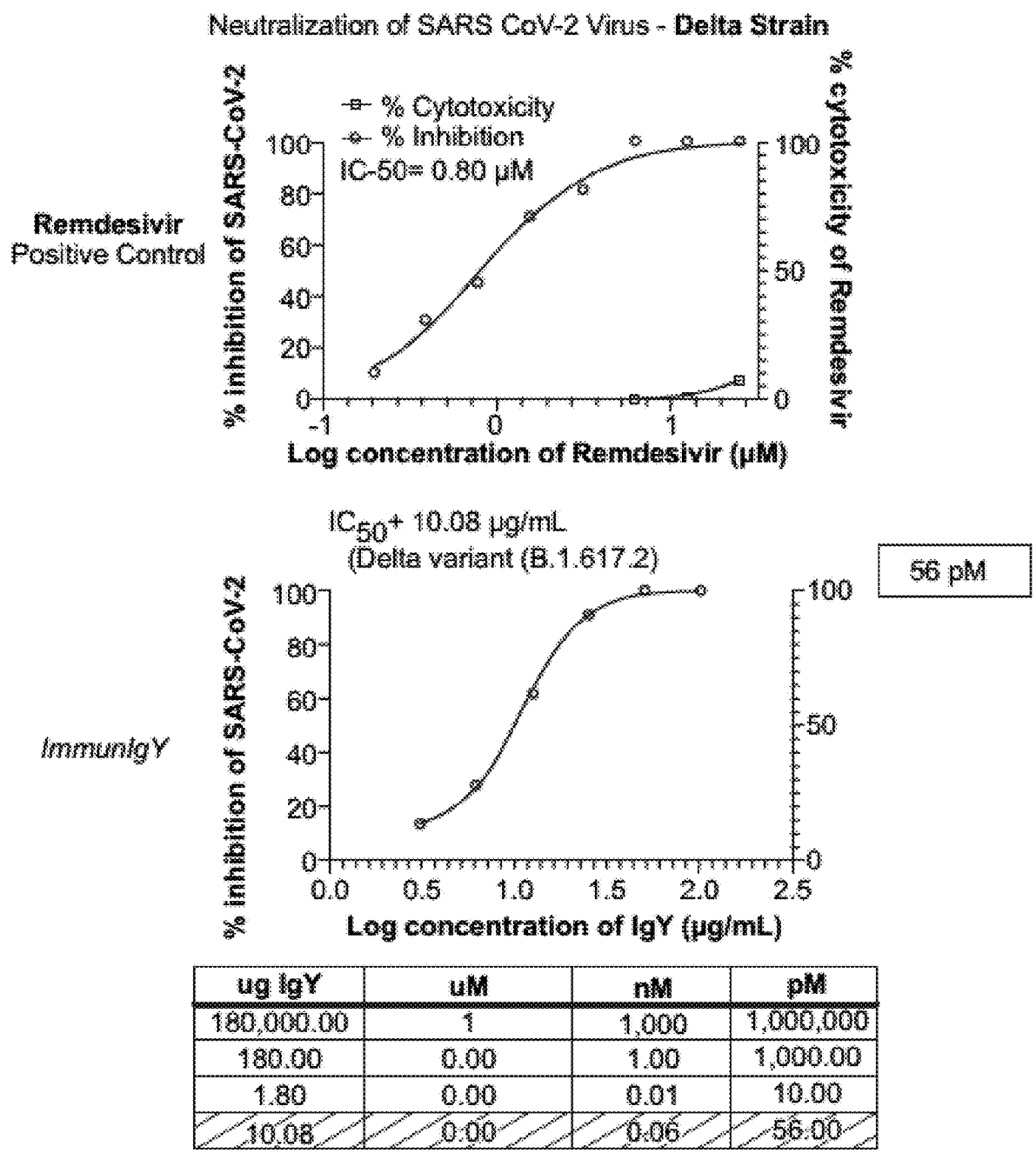
Figure 8:
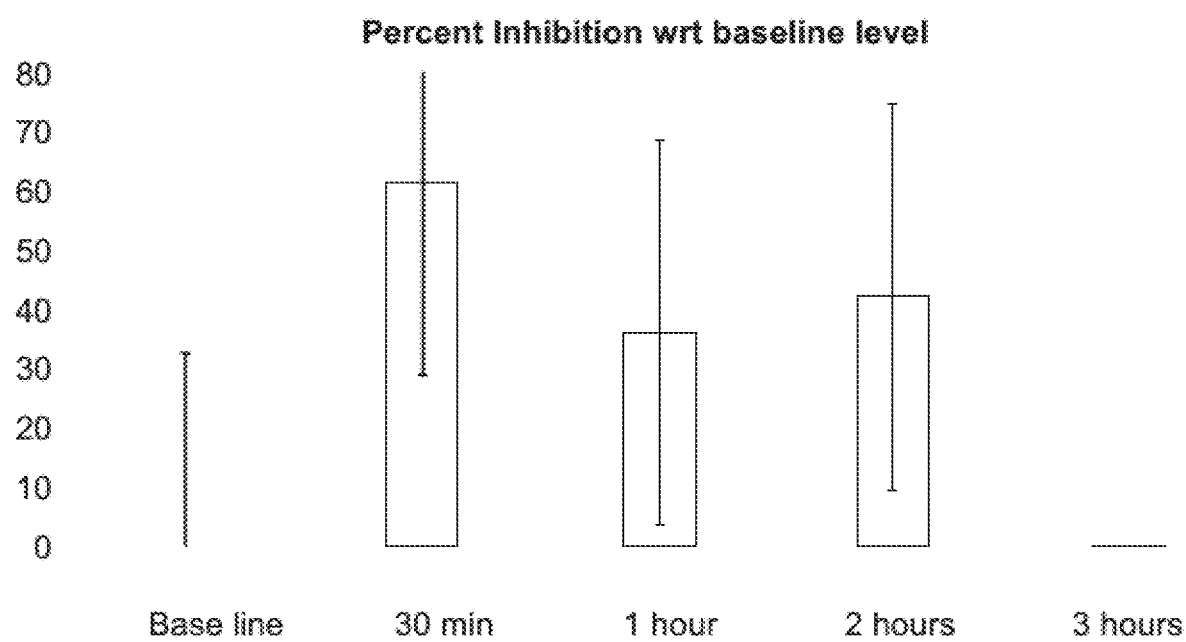
Figure 9:
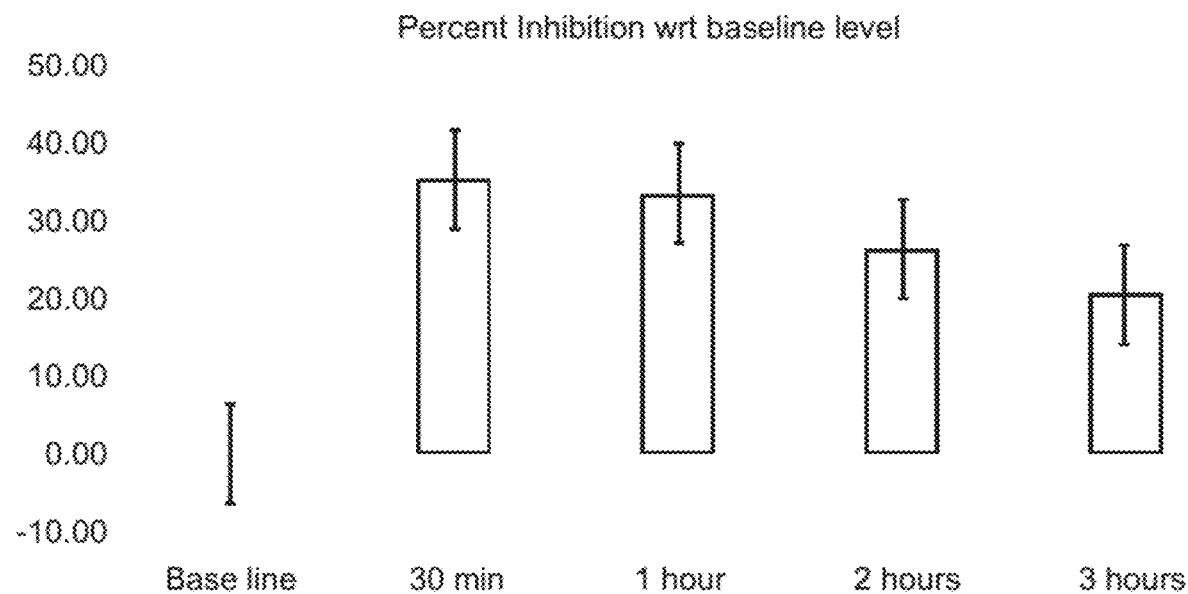
Figure 10:
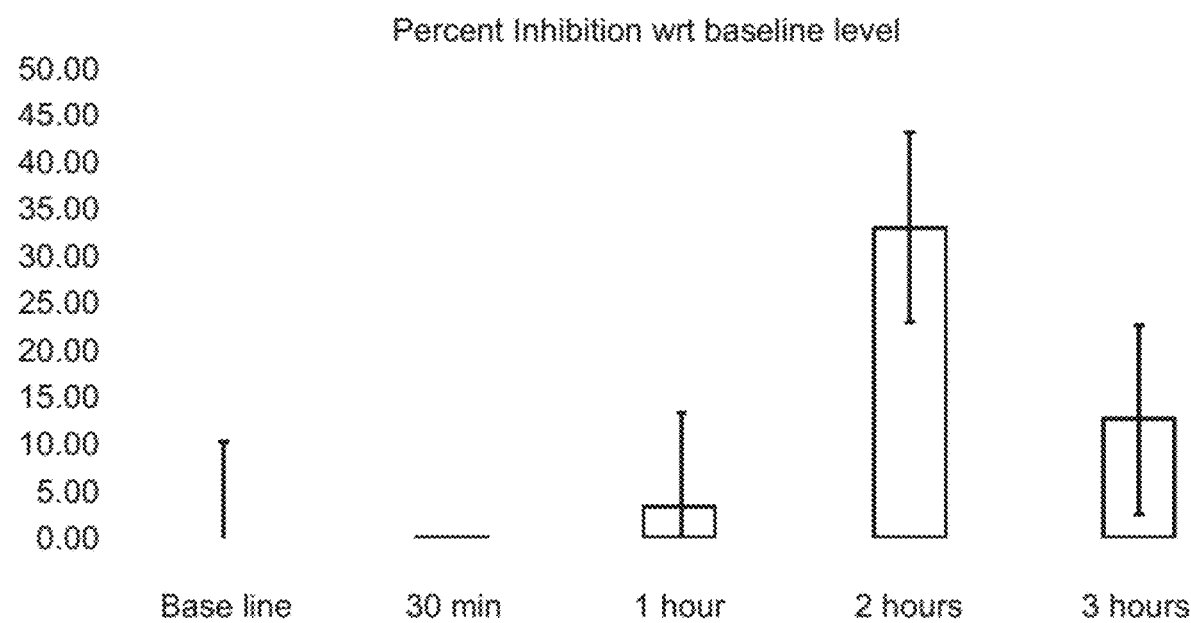

Additional studies were conducted to determine the effect of the anti-RBD IgY on neutralization of the Wuhan strain and Delta strain of SARS-CoV2 using the PRNT assay described above. Remdesivir was used as a positive control. The results for the Wuhan strain are shown in FIG. 6, and the results for the Delta strain are shown in FIG. 7. The results demonstrate that the anti-RBD IgY antibodies were able to neutralize the SARS CoV-2 variants to the same extent in a Viral PRNT assay. The results suggest that the polyclonal nature of the anti-RBD IgY antibodies allows the antibodies to be broad-spectrum antibodies with the ability to neutralize the native and delta variant RBD.

Example 4. Evaluation of Anti-RBD IgY in a Human Clinical Trial

The primary objective of the study was to evaluate the effectiveness of anti-RBD IgY (IMMUNIGY-Vistop) in neutralizing RBD-ACE2 following administration to subjects.

| | Study Protocol |
|---|---|
| Protocol Title | A Study to Evaluate the Effectiveness of IMMUNIGY-Vistop (a formulated oral IgY product containing Anti-RBD IgY) in neutralizing the binding of RBD of the viral protein S1 to ACE2 human cellular receptor in Human Saliva and at various times following administration of IMMUNIGY-VISTOP (IMMUNIGY) to subjects. |
| Sponsor | Lay Sciences, Inc., Jupiter FL. USA |
| Study Sites | Reagene Biosciences Laboratories, Hyderabad, India |
| Study Phase and Design | Development Phase<br>Prospective<br>Open label pilot study |
| Study Medication | IMMUNIGY is a powder formulated for oral dosing following dissolution in water (1 gm in 20 mL) |
| Comparator | Subjects' saliva prior to administration with IMMUNIGY |
| Safety Evaluation Points | Any reports of oral and GI discomfort over a 24-hour period |
| Objectives | Primary Endpoint:<br>Following are based on evaluable subjects. Evaluable subjects are naïve with no preexposure to the virus and have not been vaccinated. All subjects will be included in the ITT or mITT population.<br>1) Reduction in RBD binding by subject's saliva by at least 20% at 30 minutes post administration of IMMUNIGY relative to pre-administration control in the evaluable population.<br>Secondary Endpoints:<br>1) Reduction in RBD binding by subject's saliva by at least 15% at 60 minutes post administration of IMMUNIGY relative to pre-administration control in the evaluable population.<br>2) Reduction in RBD binding by subject's saliva by at least 10% at 120 minutes post administration of IMMUNIGY relative to pre-administration control in the evaluable population.<br>Tertiary Endpoints:<br>1) Reduction in RBD binding by subject's saliva by at least 5% >3 hours post administration of IMMUNIGY relative to pre-administration control in the evaluable and ITT/mITT population. |

| | Study Protocol |
|---|---|
| | 2) Reduction in RBD binding by subject's saliva by at least 20% at 30 minutes post administration of IMMUNIGY relative to pre-administration control in the ITT/mITT population.<br>3) Reduction in RBD binding by subject's saliva by at least 15% at 60 minutes post administration of IMMUNIGY relative to pre-administration control in the ITT/mITT population.<br>4) Reduction in RBD binding by subject's saliva by at least 10% at 120 minutes post administration of IMMUNIGY relative to pre-administration control in the mITT population. |
| Study Design | Subject will sign consent to collect saliva samples at pre-specified periodic times.<br>The saliva samples will be used only to test in the neutralizing assay developed by Lat Sciences.<br>The samples may be stored indefinitely for future analyses using the neutralizing assay (interference of RBD-ACE binding) developed by Lay Sciences.<br>Subject's saliva at pre-administration will serve as the untreated control.<br>Subjects will be administered with 20 mL of IMMUNIGY-Vistop (1 gm) and will be instructed to swish the product in the mouth for a period of 1 minute and then swallowed. 30 minutes prior to the administration of IMMUNIGY-Vistop, the subject will rinse their mouth thrice with plain water and abstain from eating or drinking anything till IMMUNIGY-Vistop is administered<br>Periodically, at 30 minutes, 1 hour and 2 hours samples of saliva will be collected<br>If possible, an additional saliva sample will be collected at 3+ hours.<br>Technical personnel from Reagene will oversee the sample collection and administration of IMMUNIGY-Vistop.<br>The analyses will be ongoing as the data accrues, without incurring alpha penalty.<br>Interim analyses following 10 subjects are enrolled in the study will be assessed for futility of the study to determine if the study will continue or end. |
| Selection Criteria (inclusion/exclusion) | Inclusion criteria:<br>This is an all-comer study, will include naïve, vaccinated and SARS CoV-2 infected subjects<br>Exclusion criteria:<br>Saliva samples with high mucoid content<br>Colored saliva, such as those from betel leaf chewing or excessive use of tobacco. |
| Monitoring And Data Collection For Each Subject | Technical personnel from Reagene will oversee the sample collection and administration of IMMUNIGY-Vistop.<br>Patient history will be recorded by Reagene Personnel<br>Reagene will record any other observations such as, subjects washing their mouth or drinking beverages post administration of IMMUNIGY-Vistop and prior to sample collection.<br>Reagene will record desirability of the product such as, flavor, texture, after taste (lingering taste), discomfort etc.<br>Saliva samples at 30, 60, 120 minutes will be collected for analyses<br>Additionally, saliva sample at 3+ hours will also be collected for analyses.<br>Saliva samples may be stored for additional testing in the future for neutralizing antibodies.<br>Data will be collected from the assay tests of the saliva samples and will be recorded.<br>The data recording of the subjects will be anonymous; meaning each subject will be assigned an enrollment number sequentially, such as Subject 001, Subject 002 etc.<br>Any samples collected and stored will be destroyed within one year following its collection and will be recorded by Reagene. |

-continued

| Study Protocol | |
|---|---|
| | The samples collected from subjects will not be used to assess for any other than as intended in this protocol, which is the determination of neutralizing antibodies against CoV-2 virus, which is a measure of RBD binding to ACE2. |
| Population | All comers<br>Ages 18+<br>May be amended to include 12+ ages as well |
| Planned Sample Size | Minimally 15 evaluable subjects<br>Maximally 100 ITT/mITT subjects |
| Data Analysis | For treatment differences chi-square or t tests will be used depending on the sample size for all of the following analyses.<br>1. Point analyses at specific times will be assessed<br>2. Magnitude changes relative to baseline will also be assessed<br>3. For continuous variables, area under the under the curve analyses will be used.<br>Primary, Secondary and Tertiary endpoints will include all of the above analyses.<br>Missing data will be imputed using a median of all evaluable assessments at each timepoint. |
| Safety | The formulation is based on nutraceutical guidance and the components are generally recognized as Safe (GRAS) |
| Efficacy/Benefit | Retention of neutralizing activity as specified in the endpoints above baseline is determined to be beneficial and considered to be an efficacious product. |

This clinical study was aborted after 4 persons were enrolled due to high COVID rates at the study sites and due to restrictions imposed by the local government. Preliminary results of the clinical study demonstrate that the antibodies are effective in oral mucosa following administration of the product. Although the study was aborted due to COVID restrictions, the initial results demonstrated that vaccinated, unvaccinated and infected persons who consumed IMMUNIGY-Vistop had elevated levels of neutralizing activity in their saliva for at least 3 hours after consumption of the product.

Applicants designed a study to test the ability of anti-RBD IgY formulated as a drink to boost RBD-ACE2 neutralizing activity in saliva after a single oral rinse with a lychee flavored drink containing the anti-RBD IgY. To determine the increase in saliva neutralizing activity, we designed a simple protocol. Healthy volunteers were provided with 10 ml of drink containing 16.6 ug/ml of purified anti-RBD IgY as an oral rinse. The volunteers rinsed their oral cavity for 3 minutes and then spit out the rinse. Saliva samples were collected at zero time (basal sample before oral rinse) and at 30, 1 hour, 2 hours and 3 hours after the rinse and stored at 4° C. till the dot blot assay was performed. Just prior to use, the saliva was gently centrifuged at 5000 RPM for 2 minutes to settle any debris and the supernatant (10 μl) was used in the dot blot. Data are reported as increase in neutralizing activity over the basal levels.

FIG. 8 shows the neutralizing activity in saliva samples from a volunteer who was not vaccinated for SARS CoV2, and was RTPCR negative for SARS CoV2. The data show that there was a time-dependent increase in neutralizing activity of up to a 60% increase over baseline in this subject, with persistence of some activity 2 hours after oral rinse. FIG. 9 shows neutralizing activity in a volunteer who was vaccinated for SARS CoV2 one month prior to the study and did not have COVID 19. As shown in FIG. 9, there was up to a 30% increase in neutralizing activity above baseline and there was demonstrable activity even at 3 hours after the oral rinse. These data suggest that even in an individual who had one shot of a SARS CoV2 vaccine there was still an increase in neutralizing activity over base line. FIG. 10 shows neutralizing activity in another volunteer who had received two shots of a SARS CoV2 vaccine, with the second shot administered one month before the study. Interestingly, in this case the increase in saliva neutralizing activity was not detectable at 30 minutes but was clearly present at 1, 2 and 3 hours with peak activity of 30% increase at 2 hours (FIG. 10). This result suggests that even in fully vaccinated individuals, there is still an increase in saliva neutralizing activity by oral rinse with the IgY beverage. Finally the impact of oral rinse on an individual who had recently recovered from COVID 19 and was RTPCR negative for the virus at the time of this study was examined. There was no increase in the neutralizing activity at any time point after the oral rinse. It is possible that the lack of increase in neutralizing activity was due to high levels of neutralizing activity in this individual with recent COVID 19 infection, but that remains to be tested.

The invention claimed is:

1. A method of preparing a hyperimmunized egg product comprising:

a) hyperimmunizing an egg-producing animal with a composition comprising an antigen having the amino acid sequence of SEQ ID NO: 19 and b) preparing a hyperimmunized egg product from one or more eggs produced by the animal by dehydrating, spray drying, or freeze drying of whole egg, yolk or a purified IgY fraction from the one or more eggs.

2. The method of claim 1, wherein the hyperimmunized egg product is in a form of nanoparticles having a diameter less than 1000 nm.

3. The method of claim 1, wherein the hyperimmunized egg product is in the form of microparticles having a diameter in a range of about 0.1 to 10 microns.

4. The method of claim 1, wherein the hyperimmunized egg product is in the form of nanoparticles having a diameter in a range of about 10 to 100 nm.

5. The method of claim 1, further comprising encapsulating the hyperimmunized egg product in an encapsulating material.

6. The method of claim 5, wherein the encapsulating is performed by a process selected from among multi-walled microencapsulation, hot melt encapsulation, phase separation encapsulation, spontaneous emulsion, solvent evaporation microencapsulation, solvent removal microencapsulation, and coacervation.

7. The method of claim 1, further comprising mixing the hyperimmunized egg product with an agent that improves flow properties.

* * * * *